US012735457B2

(12) United States Patent
Rondinone et al.

(10) Patent No.: US 12,735,457 B2
(45) **Date of Patent: *Sep. 15, 2026**

(54) COMPOSITIONS INCLUDING MULTI-AGONIST PEPTIDES AND METHODS OF MANUFACTURE AND USE

(71) Applicant: Pep2Tango Therapeutics Inc., Potomac, MD (US)

(72) Inventors: Cristina Martha Rondinone, Potomac, MD (US); Soumitra S. Ghosh, San Diego, CA (US); Waleed Danho, Del Mar, CA (US)

(73) Assignee: Pep2Tango Therapeutics Inc., Potomac, MD (US)

( * ) Notice: Subject to any disclaimer, the term of this patent is extended or adjusted under 35 U.S.C. 154(b) by 354 days.

This patent is subject to a terminal disclaimer.

(21) Appl. No.: 17/812,993

(22) Filed: Jul. 15, 2022

(65) Prior Publication Data

US 2023/0203100 A1 Jun. 29, 2023

Related U.S. Application Data

(60) Provisional application No. 63/222,747, filed on Jul. 16, 2021.

(51) Int. Cl.

| | |
|---|---|
| ***C07K 14/00*** | (2006.01) |
| ***A61K 9/00*** | (2006.01) |
| ***A61K 38/00*** | (2006.01) |
| ***A61K 47/65*** | (2017.01) |
| ***A61P 3/04*** | (2006.01) |
| ***A61P 3/10*** | (2006.01) |
| ***A61P 9/12*** | (2006.01) |

(52) U.S. Cl.

CPC ............ *C07K 14/00* (2013.01); *A61K 9/0019* (2013.01); *A61K 47/65* (2017.08); *A61P 3/04* (2018.01); *A61P 3/10* (2018.01); *A61P 9/12* (2018.01); *A61K 38/00* (2013.01)

(58) Field of Classification Search

CPC ...... C07K 14/00; C07K 14/605; A61K 47/65; A61P 3/10; A61P 3/00

See application file for complete search history.

(56) References Cited

U.S. PATENT DOCUMENTS

| | | | | |
|---|---|---|---|---|
| 2010/0048462 A1 | 2/2010 | Ryge et al. | | |
| 2010/0286365 A1 | 11/2010 | Ghosh et al. | | |
| 2013/0196913 A1 | 8/2013 | Levy et al. | | |
| 2015/0368310 A1* | 12/2015 | Dimarchi | A61P 3/04 | 530/308 |
| 2019/0135886 A1 | 5/2019 | Just et al. | | |
| 2022/0135638 A1* | 5/2022 | Imoto | A61P 1/08 | 514/9.7 |
| 2023/0143604 A1* | 5/2023 | Henninot | A61P 1/04 | 514/5.3 |
| 2024/0059753 A1 | 2/2024 | Rondinone | | |

FOREIGN PATENT DOCUMENTS

| | | | |
|---|---|---|---|
| WO | WO-2006086769 A2 * | 8/2006 | A61P 1/04 |
| WO | WO-2024015922 A1 | 1/2024 | |

OTHER PUBLICATIONS

Abushamat et al. 2024, Clinical Gastroenterology and Hepatology. vol. 22, issue 8, pp. 1565-1574. (Year: 2024).*

Kaltenbach. M., 2023. Liver Fellow Network, available at https://www.aasld.org/liver-fellow-network/core-series/why-series/why-are-glp-1-agonists-being-used-treat-patients#:~:text=GLP%2D1%20agonists%20have%20shown%20promise%20in%20treating,*%20Diarrhea%20*%20Increased%20risk%20of%20cholelithiasis (Year: 2023).*

Tornea et al., 2026, Pharmaceutics, 18(1): 86, pp. 1-26. (Year: 2026).*

International Search Report and Written Opinion for International Application No. PCT/US2022/073793 dated Nov. 25, 2022, 19 pages.

Invitation to Pay Fee for International Application No. PCT/US2022/073793 dated Sep. 28, 2022, 4 pages.

Invitation to Pay Additional Fees for International Application No. PCT/US2023/070152, dated Jan. 4, 2024, 3 pages.

International Preliminary Report on Patentability for International Application No. PCT/US2022/073793 dated Jan. 25, 2024, 9 pages.

International Search Report and Written Opinion for International Application No. PCT/US2023/070152 dated Mar. 11, 2024, 13 pages.

Extended European Search Report for European Application No. 22843079.9 mailed Apr. 16, 2025, 8 pages.

(Continued)

*Primary Examiner* — Thea D'Ambrosio
*Assistant Examiner* — Claudia Espinosa
(74) *Attorney, Agent, or Firm* — COOLEY LLP

(57) ABSTRACT

The present invention relates generally to novel multi-agonist peptides useful as agents for the treatment and prevention of metabolic diseases and disorders, for example those which can be alleviated by control of weight loss, plasma glucose and lipid levels, insulin levels, and/or insulin secretion, positive inotropic effects, reduction of catabolic effects, slowing of gastric emptying and preventing neuro-degeneration. Such conditions and disorders include, but are not limited to, control of food intake, weight loss, energy metabolism, plasma glucose levels, insulin levels, and/or insulin secretion, positive inotropic effects, reduction of catabolic effects, slowing of gastric emptying, obesity, diabetes and diabetes-related conditions, liver fat-associated inflammation and injury.

8 Claims, 2 Drawing Sheets

Specification includes a Sequence Listing.

(56) References Cited

OTHER PUBLICATIONS

Gabe et al., "Molecular interactions of full-length and truncated GIP peptides with the GIP receptor—A comprehensive review," Peptides, Mar. 2020; 125:170224; 8 pages.
Mahalakshmi et al., "Non-Protein Amino Acids in the Design of Secondary Structure Scaffolds", Methods Mol Biol; Feb. 2006; 340:71-94.
Musaimi et al., "2017 FDA Peptide Harvest," [Online]. Preprints.org (Apr. 10, 2018). [Retrieved from the Internet (retrieval date unknown) at URL:https://doi.org/10.20944/preprints201804.0126.v1]; 11 pages.
U.S. Appl. No. 18/352,077, Non-Final Office Action mailed Feb. 13, 2026; Inventor Rondinone, Cristina Martha et al.; 24 pages.

* cited by examiner

COMPOSITIONS INCLUDING MULTI-AGONIST PEPTIDES AND METHODS OF MANUFACTURE AND USE

CROSS-REFERENCE TO RELATED APPLICATIONS

This application claims the benefit of U.S. provisional application No. 63/222,747, which was filed on Jul. 16, 2021 and is incorporated herein by reference in its entirety.

STATEMENT REGARDING SEQUENCE LISTING

The Sequence Listing associated with this application is provided in ST.26 XML format and is hereby incorporated by reference into the specification. The name of the XML file containing the Sequence Listing is PEP2-001-01US_SubSeqList_ST26.xml. The text file is 72,417 bytes, was created on Mar. 18, 2024, and is being submitted electronically.

FIELD OF THE INVENTION

The present invention relates generally to novel multi-agonist peptides useful as agents for the treatment and prevention of metabolic diseases and disorders, for example those which can be alleviated by control of weight loss, plasma glucose and lipid levels, insulin levels, and/or insulin secretion, positive inotropic effects, reduction of catabolic effects, slowing of gastric emptying and preventing neuro-degeneration. Such conditions and disorders include, but are not limited to, control of food intake, weight loss, energy metabolism, plasma glucose levels, insulin levels, and/or insulin secretion, positive inotropic effects, reduction of catabolic effects, slowing of gastric emptying, obesity, diabetes and diabetes-related conditions, liver fat-associated inflammation and injury. Such conditions and disorders include, but are not limited to, hypertension, dyslipidemia, cardiovascular disease, eating disorders and rare genetic disorders of obesity such as Prader Willi Syndrome, critical care, insulin-resistance and disorders thereof such as polycystic ovary syndrome, obesity, diabetes mellitus of any kind, including type 1, type 2, and gestational diabetes, and CNS disorders such as preventing neurodegeneration, depression, alcohol addition, Alzheimer's disease and Parkinson's disease, and nonalcoholic steatohepatitis (NASH).

BACKGROUND OF THE INVENTION

Incretin peptides are hormones and peptide mimetics are gluco-regulatory agents that cause an increase in the amount of insulin released when glucose levels are normal or particularly when they are elevated. These incretin peptides have other actions beyond the initial incretin action defined by insulin secretion. For instance, they may also have actions to reduce glucagon production, increase satiety, delay gastric emptying, regulate white and brown adipose tissue and elicit weight loss. In addition, they may have actions to improve insulin sensitivity, and they may increase islet cell neogenesis—the formation of new islets.

The concept of the incretin effect developed from the observation that insulin responses to oral glucose exceeded those measured after intravenous administration of equivalent amounts of glucose. It was concluded that gut-derived factors, or incretins, influenced postprandial insulin release. Nutrient entry into the stomach and proximal gastrointestinal tract causes release of incretin hormones, which then stimulate insulin secretion. This insulinotropism, or ability to stimulate insulin secretion, can be quantified by comparing insulin or C-peptide responses to oral vs. intravenous glucose loads. In this way, it has been shown that the incretin effect is responsible for about 50% to 70% of the insulin response to oral glucose in healthy individuals.

Although many postprandial hormones have incretin-like activity, predominant incretin peptides include glucose-dependent insulinotropic polypeptide, also known as gastric inhibitory polypeptide (GIP), glucagon-like peptide-1 (GLP-1), and exendin peptides (which are non-endogenous incretin mimetics). GIP and GLP-1 both belong to the glucagon peptide superfamily and thus share amino acid sequence homology. GIP and GLP-1 are secreted by specialized cells in the gastrointestinal tract and have receptors located on islet cells as well as other tissues. As incretins, both are secreted from the intestine in response to ingestion of nutrients, which results in enhanced insulin secretion. The insulinotropic effect of GIP and GLP-1 is dependent on elevations in ambient glucose. Both are rapidly inactivated by the ubiquitous enzyme dipeptidyl peptidase IV (DPP-IV).

Native human GIP is a single 42-amino acid peptide synthesized in and secreted by specialized enteroendocrine K-cells. These cells are concentrated primarily in the duodenum and proximal jejunum, although they also can be found throughout the intestine. The main stimulant for GIP secretion is ingestion of carbohydrate- and lipid-rich meals. Following ingestion, circulating plasma GIP levels increase 10- to 20-fold. The half-life of intact GIP is estimated to be approximately 7.3 minutes in healthy subjects and 5.2 minutes in diabetic subjects.

The physiologic effects of GIP have been elucidated using GIP receptor antagonists, GIP peptide antagonists, and GIP receptor knockout mice, in addition to GIP infusion protocols. Blocking GIP binding to its receptor results in attenuated glucose-dependent insulin secretion following oral glucose load in rats and mice. Similarly, administration of GIP antagonists or GIP antisera markedly reduces the postprandial insulin release in rats. GIP receptor knockout mice demonstrate normal fasting glucose levels but mild glucose intolerance following oral glucose loads. Interestingly, they also exhibit resistance to diet-induced obesity following months of high-fat feeding. Additionally, in the leptin-deficient ob/ob mouse, the GIP receptor knockout genotype appears to decrease the extent of obesity that develops.

GIP has many non-incretin effects as well. GIP activation of the GIP receptor has an anti-emetic action. Unlike other insulin secretagogues, GIP stimulates beta-cell proliferation and cell survival in INS-1 islet cell-line studies. Furthermore, animal studies have suggested a role for GIP in lipid metabolism by stimulating lipoprotein lipase activity, inducing fatty acid incorporation into adipose tissue and stimulating fatty acid synthesis. GIP also appears to stimulate glucagon secretion from the isolated perfused rat pancreas, although human studies have not demonstrated any significant influence on glucagon secretion. Furthermore, unlike GLP-1, GIP appears to act by accelerating emptying of the stomach rather than by inhibiting gastrointestinal motility.

Despite potent glucoregulatory actions through glucose-dependent stimulation of insulin secretion, the insulinotropic effect of GIP is significantly reduced in diabetic subjects compared to normal individuals (16-18). Consequently, clinical use of GIP has not been significantly advanced. Further, there remains a need to develop additional diabetic treatment modalities as well as treatments for metabolic diseases, conditions, and disorders. Accordingly, the invention encompasses Peptides of the Invention and methods for their use to treat or prevent metabolic diseases, conditions, and disorders.

GLP-1 is a potent insulin secretagogue that is secreted from the intestinal mucosa in response to food intake. The profound incretin effect of GLP-1 is underscored by the fact that GLP-1R knockout mice are glucose-intolerant. The incretin response of intravenous infused GLP-1 is preserved in diabetic subjects, though the incretin response to oral glucose in these patients is compromised. GLP-1 administration by infusion or sc injections controls fasting glucose levels in diabetic patients, and maintains the glucose threshold for insulin secretion. GLP-1 has shown tremendous potential as a therapeutic agent capable of augmenting insulin secretion in a physiological manner, while avoiding hypoglycemia associated with sulfonylurea drugs. Other important effects of GLP-1 on glucose homeostasis are suppression of glucagon secretion and inhibition of gastric motility. GLP-1 inhibitory actions on pancreatic alpha cell secretion of glucagon leads to decreases in hepatic glucose production via reduction in gluconeogenesis and glycogenolysis. This anti-glucagon effect of GLP-1 is preserved in diabetic patients. The so-called ileal brake effect of GLP-1, in which gastric motility and gastric secretion are inhibited, is affected via vagal efferent receptors or by direct action on intestinal smooth muscle. Reduction of gastric acid secretion by GLP-1 contributes to a lag phase in nutrient availability, thus obviating the need for rapid insulin response. In summary, the gastrointestinal effects of GLP-1 contribute significantly to delayed glucose and fatty acid absorption and modulate insulin secretion and glucose homeostasis. GLP-1 has also been shown to induce beta cell specific genes, such as GLUT-1 transporter, insulin (via the interaction of PDX-1 with insulin gene promoter), and hexokinase-1. Thus GLP-1 could potentially reverse glucose intolerance normally associated with aging, as demonstrated by rodent experiments. In addition, GLP-1 may contribute to beta cell neogenesis and increase beta cell mass, in addition to restoring beta cell function during states of beta cell insufficiency. Central effects of GLP-1 include increases in satiety coupled with decreases in food intake, effected via the action of hypothalamic GLP-1 receptor. These anorectic effects were absent in GLP-1R knock out mice. In addition, GLP-1 receptor signaling has been implicated in the regulation of energy expenditure and brown adipose tissue thermogenesis. (Beiroa D, et al. Diabetes 63:3346-3358, 2014).

Another family of peptide hormones implicated in metabolic diseases and disorders is the amylin family of peptide hormones, including amylin, calcitonin, calcitonin gene related peptide, adrenomedullin, and intermedin (also known as "AFP-6"). Amylin is a 37-amino acid peptide hormone. It was isolated, purified and chemically characterized as the major component of amyloid deposits in the islets of pancreases of human Type 2 diabetics (Cooper et al., Proc. Natl. Acad. Sci., USA, 84:8628-8632 (1987)). The amylin molecule has two post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the CLAIMS-terminal position, a typical sequence for amidation by protein amidating enzyme, PAM (Cooper et al., Biochem. Biophys. Acta, 1014:247-258 (1989)).

Amylin is believed to regulate gastric emptying, and suppress glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intrahypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue, and for attenuation of alcohol-related behaviors.

Calcitonin was named for its secretion in response to induced hypercalcemia and its rapid hypocalcemic effect. It is produced in and secreted from neuroendocrine cells in the thyroid that have since been termed C cells. The best-studied action of calcitonin is its effect on the osteoclast. In vitro effects of calcitonin include the rapid loss of ruffled borders and decreased release of lysosomal enzymes. Ultimately, the inhibition of osteoclast functions by calcitonin results in a decrease in bone resorption. However, neither a chronic reduction of serum calcitonin in the case of thyroidectomy nor the increased serum calcitonin found in medullary thyroid cancer appears to be associated with changes in serum calcium or bone mass. It is thus most likely that a major function calcitonin is to combat acute hypercalcemia in emergency situations and/or protect the skeleton during periods of "calcium stress" such as growth, pregnancy, and lactation. Calcitonin has an effect on plasma calcium levels and inhibits osteoclast function and is widely used for the treatment of osteoporosis. Therapeutically, salmon calcitonin appears to increase bone density and decrease fracture rates with minimal adverse effects. Calcitonin has also been successfully used over the past 25 years as a therapy for Paget's disease of bone, which is a chronic skeletal disorder that may result in enlarged or deformed bones in one or more regions of the skeleton. Calcitonin is also widely used for its analgesic effect on bone pain experienced during osteoporosis, although the mechanism for this effect is not clearly understood. Salmon calcitonin has effects beyond those related to bone metabolism. In human studies, salmon calcitonin inhibits gastric emptying and gastrin release following a meal while evoking a dose-dependent relaxation of the gallbladder both in the postprandial and fasting state In mice and monkeys, salmon calcitonin acts anorectically and causes weight loss after a single administration. In chronic studies, oral preparations of salmon calcitonin also reduce food intake and body weight in rat models of obesity and diabetes.

Metabolic diseases and disorders take on many forms, including obesity, diabetes, dyslipidemia, insulin resistance, fatty liver, steatohepatitis, cellular apoptosis, etc. Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for diabetes, hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g. Kopelman, Nature 404:635-43 (2000)). It reduces life-span and carries a serious risk of co-morbidities above, as well disorders such as infections, varicose veins, acanthosis *nigricans*, eczema, exercise intolerance, insulin resistance, hypertension hypercholesterolemia, cholelithiasis, orthopedic injury, and thromboembolic disease (Rissanen et al., Br. Med. J. 301:835-7 (1990)). Obesity is also a risk factor for certain types of cancer and for the group of conditions called insulin resistance syndrome, or "Syndrome X." Recent estimate for the medical cost of obesity and associated disorders is $2 Trillion worldwide. The pathogenesis of obesity is believed to be multifactorial, but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

Diabetes is a disorder of carbohydrate metabolism characterized by hyperglycemia and glucosuria resulting from insufficient production or utilization of insulin. Diabetes severely affects the quality of life of large parts of the populations in developed countries. Insufficient production of insulin is characterized as type 1 diabetes and insufficient utilization of insulin is type 2 diabetes. However, it is now widely recognized that there are many distinct diabetes related diseases which have their onset long before patients are diagnosed as having overt diabetes. Also, the effects from the suboptimal control of glucose metabolism in diabetes gives rise to a wide spectrum of related lipid and cardiovascular disorders.

Dyslipidemia, or abnormal levels of lipoproteins in blood plasma, is a frequent occurrence among diabetics. Dyslipidemia is typically characterized by elevated plasma triglycerides, low HDL (High Density Lipoprotein) cholesterol, normal to elevated levels of LDL (Low Density Lipoprotein) cholesterol and increased levels of small dense, LDL (Low Density Lipoprotein) particles in the blood. Dyslipidemia is one of the main contributors to the increased incidence of coronary events and deaths among diabetic subjects. Epidemiological studies have confirmed this by showing a several-fold increase in coronary deaths among diabetic subjects when compared with non-diabetic subjects. Several lipoprotein abnormalities have been described among diabetic subjects.

Insulin resistance is the diminished ability of insulin to exert its biologically action across a broad range of concentrations. In insulin resistance, the body secretes abnormally high amounts of insulin to compensate for this defect and a state of impaired glucose tolerance develops. Failing to compensate for the defective insulin action, the plasma glucose concentration inevitable rises, resulting in the clinical state of diabetes. It is recognized that insulin resistance and relative hyperinsulinemia have a contributory role in obesity, hypertension, atherosclerosis and type 2 diabetes. The association of insulin resistance with obesity, hypertension and angina has been described as a syndrome, Syndrome X, having insulin resistance as the common pathogenic link.

Attempts to treat the multiple abnormalities associated with diabetes have prompted for the administration of several anti-diabetic medicaments in order to address these abnormalities in the different patients. Examples of anti-diabetic medicaments are proteins such as insulin and insulin analogues, GLP-1 analogues, and small molecules such as insulin sensitizers, insulin secretagogues, alpha-glucosidase inhibitors, sodium glucose cotransporter-2 (SGLT-2) inhibitors, DPP-IV inhibitors, and appetite regulating compounds.

Non-alcoholic fatty liver disease (NAFLD) is an umbrella term and encompasses the simple deposition of fat in the liver to more progressive steatosis with associated hepatitis, fibrosis, cirrhosis, and in some cases hepatocellular carcinoma. NAFLD is comprised of non-alcoholic fatty liver (NAFL) and non-alcoholic steatohepatitis (NASH). NAFL is characterized by steatosis of the liver, involving greater than 5% of parenchyma, with no evidence of hepatocyte injury [2]. Whereas, NASH is defined by histologic terms, that is a necroinflammatory process whereby the liver cells become injured in a background of steatosis. The natural history of NAFLD remains incompletely characterized. Studies indicate the incidence of NAFLD increasing in concert with the rising rates of metabolic syndrome. Patients with Type 2 diabetes display a very high risk of developing NASH as well as a two-to-four-fold increased risk of fatty liver associated complications. Currently, there are no approved treatments for NASH.

There remains a need to develop therapeutics useful in the above described metabolic diseases, conditions, and disorders. Accordingly, present invention provides novel multi-agonist peptides and methods for producing and using them. The peptides of the invention find use in the metabolic diseases, conditions, and disorders described above and herein.

SUMMARY OF THE INVENTION

The invention provides inter alia novel multi-agonist peptides and methods of treating and preventing obesity and related disorders including, metabolic and liver disorders.

The invention relates generally to novel peptides useful as agents for the treatment and prevention of metabolic diseases and disorders which can be alleviated by control of food intake, weight loss, energy metabolism, plasma glucose levels, insulin levels, and/or insulin secretion, positive inotropic effects, reduction of catabolic effects, slowing of gastric emptying, obesity, diabetes and diabetes-related conditions, liver fat-associated inflammation and injury. Such conditions and disorders include, but are not limited to, hypertension, dyslipidemia, cardiovascular disease, eating disorders and rare genetic disorders of obesity such as Prader Willi Syndrome, critical care, insulin-resistance and disorders thereof such as polycystic ovary syndrome, obesity, diabetes mellitus of any kind, including type 1, type 2, and gestational diabetes, alcohol addiction, and CNS disorders such as preventing neurodegeneration, depression, alcohol addition, Alzheimer's disease and Parkinson's disease, and nonalcoholic steatohepatitis (NASH).

The invention comprises "Peptides of the Invention," as defined herein, that include two or more component peptides independently selected from at least two peptides, including, for example, but not limited to, bio-active components including amylin, glucose-dependent insulinotropic polypeptide (GIP), glucagon-like peptide-1 (GLP-1), and calcitonin.

The invention encompasses peptides exhibiting at least one hormonal activity. The Peptides of the Invention comprise at least two bio-active peptides covalently linked together, optionally through a linker group, wherein at least one of the bio-active peptides exhibits at least one hormonal activity of a component peptide. The bio-active peptides are independently selected from: component peptides (e.g., GIP, amylin, GLP-1), fragments of component peptides that exhibit at least one hormonal activity of the component peptide, analogs and derivatives of component peptides that exhibit at least one hormonal activity of the component peptides, and fragments of analogs and derivatives of component peptides that exhibit at least one hormonal activity of the component peptides.

In one embodiment, a peptide exhibits at least one hormonal activity, the peptide containing at least a first peptide covalently linked to at least one additional peptide; wherein the peptides are independently selected from the group consisting of: component peptides (e.g., GIP, GLP-1, amylin); fragments of component peptides that exhibit at least one hormonal activity of the component peptides; analogs and derivatives of component peptides that exhibit at least one hormonal activity of the component peptides; and fragments of analogs and derivatives of component peptide that exhibit at least one hormonal activity of the component peptide hormones.

The invention encompasses Peptides of the Invention or a pharmaceutically acceptable salt or solvate thereof, wherein the Peptides of the Invention comprises or consists of an amino acid sequence of Formula (I):

$X^1$-$X^2$-E-G-T-F-$X^3$-S-D-Y-S-I-$X^4$-$X^3$-D-K-I-$X^6$-Q-$X^7$-$X^8$-F-V-$X^9$-W-L-$X^{10}$-$X^{11}$-$X^{12}$-$X^{13}$ $X^{14}$-$X^{15}$-$X^{16}$-C-N-T-A-T-C-$X^{17}$-$X^{18}$-$X^{19}$-$X^{20}$-L-$X^{21}$-$X^{22}$-$X^{23}$-L-$X^{24}$-$X^{25}$-$X^{26}$-$X^{27}$-$X^{28}$-$X^{29}$ $X^{30}$-$X^{31}$-$X^{32}$-$X^{33}$-$X^{34}$-P-$X^{35}$-T-N-$X^{36}$-G-$X^{37}$-N-T-Y-($NR^1R^2$) (SEQ ID NO: 23)

(I)

wherein $X^1$ is Tyr or (d) Tyr;

$X^2$ is Ala, (d) Ala, or Aib;

$X^3$ is Ile or Thr;

$X^4$ is Ala, Aib, or Gln;

$X^5$ is Met, Leu, or Val;

$X^6$ is Ala or His;

$X^7$ is Gln, Lys, or Lys-γ-Glu-γ-Glu-C=(($CH_2$)$_n$$R^3$;

$X^8$ is Ala or Asp;

$X^9$ is Asn or Gln;

$X^{10}$ is Leu, Val, or Ile;

$X^{11}$ is Ala or Val;

$X^{12}$ is Gly or Gln;

$X^{13}$ is Gly, Lys, Arg, Ser, or Lys-γ-Glu-γ-Glu-C=O($CH_2$)$_n$$R^3$;

$X^{14}$ is Pro, Gly, Lys, or Lys-γ-Glu-γ-Glu-C=O($CH_2$) $R^3$;

$X^{15}$ is Ser, Gly, Lys, or Lys-γ-Glu-γ-Glu-C=(($CH_2$)$_n$$R^3$;

$X^{16}$ is absent or is Gly or Ser;

$X^{17}$ is Ala, Met or Val;

$X^{18}$ is Thr or Leu;

$X^{19}$ is Gln or Gly;

$X^{20}$ is Arg, Lys, Gln, or Lys-γ-Glu-γ-Glu-C=O($CH_2$)$_n$$R^3$;

$X^{21}$ is Ala or Ser;

$X^{22}$ is Asn or Gln;

$X^{23}$ is Phe or Glu;

$X^{24}$ is His or Val;

$X^{25}$ is His or Arg;

$X^{26}$ is Ser or Leu;

$X^{27}$ is Ser or Gln;

$X^{28}$ is Asn or Thr;

$X^{29}$ is absent or is Asn or Gln;

$X^{30}$ is absent or is Phe;

$X^{31}$ is absent or is Gly;

$X^{32}$ is absent or is Pro;

$X^{33}$ is absent or is Ile, Lys, or Lys-γ-Glu-γ-Glu-C=O($CH_2$)$_n$$R^3$;

$X^{34}$ is Leu or Tyr;

$X^{35}$ is Pro, Lys, Arg, or Lys-γ-Glu-γ-Glu-C=O($CH_2$)$_n$$R^3$;

$X^{36}$ is Val or Thr; and $X^{37}$ is Ser, Lys, or Lys-γ-Glu-γ-Glu-C—O($CH_2$)$_n$$R^3$;

wherein $R^1$ and $R^2$ are each independently H or $C_{1-5}$ alkyl, $R^3$ is $—CO_2H$, $—CO_2CH_3$, $—CO_2NH_2$, $—CO_2NHCH_3$, $—CO_2N(CH_3)_2$, $—CH_3$, or $—NH_2$, n is an integer from 12-20.

In other embodiments, peptides components of the Peptides of the Invention can also include calcitonin (CT), calcitonin gene related peptide (CGRP), intermedin, oxyntomodulin (OXM), and exendin-4.

In certain embodiments, the Peptides of the Invention include structural motifs of component peptides that impart a desired chemical stability, conformational stability, metabolic stability, bioavailability, organ/tissue targeting, receptor interaction, protease inhibition, plasma protein binding, or other pharmacokinetic characteristic to the peptide, and structural motifs of analogs or derivatives of component peptides that impart a desired chemical stability, conformational stability, metabolic stability, bioavailability, organ/tissue targeting, receptor interaction, protease inhibition, plasma protein binding, or other pharmacokinetic characteristic to the Peptide of the Invention. In yet a further embodiment at least one of the peptides exhibits at least one hormonal activity of a component peptide.

In further embodiments, the at least one component peptide that exhibits at least one hormonal activity of a component peptide is GIP, a fragment of GIP that exhibits at least one hormonal activity, an analog or derivative of GIP that exhibits at least one hormonal activity, or a fragment of an analog or derivative of GIP that exhibits at least one hormonal activity, and the at least one other peptide.

In further embodiments, the at least one component peptide that exhibits at least one hormonal activity of a component peptide is GLP-1, a fragment of GLP-1 that exhibits at least one hormonal activity, an analog or derivative of GLP-1 that exhibits at least one hormonal activity, or a fragment of an analog or derivative of GLP-1 that exhibits at least one hormonal activity, and the at least one other peptide.

In further embodiments, the at least one component peptide that exhibits at least one hormonal activity of a component peptide is amylin, a fragment of amylin that exhibits at least one hormonal activity, an analog or derivative of amylin that exhibits at least one hormonal activity, or a fragment of an analog or derivative of amylin that exhibits at least one hormonal activity, and the at least one other peptide.

In a further alternative embodiments the at least one component peptide that exhibits at least one hormonal activity of a component peptide is calcitonin, a fragment of calcitonin that exhibits at least one hormonal activity, an analog or derivative of calcitonin that exhibits at least one hormonal activity, or a fragment of an analog or derivative of calcitonin that exhibits at least one hormonal activity, and the at least one other peptide.

In a further alternative embodiments the at least one component peptide that exhibits at least one hormonal activity of a component peptide is calcitonin gene related peptide, a fragment of calcitonin gene related peptide that exhibits at least one hormonal activity, an analog or derivative of calcitonin gene related peptide that exhibits at least one hormonal activity, or a fragment of an analog or derivative of calcitonin gene related peptide that exhibits at least one hormonal activity, and the at least one other peptide.

In a further alternative embodiments the at least one component peptide that exhibits at least one hormonal activity of a component peptide is intermedin, a fragment of intermedin that exhibits at least one hormonal activity, an analog or derivative of intermedin that exhibits at least one hormonal activity, or a fragment of an analog or derivative of intermedin that exhibits at least one hormonal activity, and the at least one other peptide.

In a further alternative embodiments the at least one component peptide that exhibits at least one hormonal activity of a component peptide is cholecystokinin, a fragment of cholecystokinin that exhibits at least one hormonal activity, an analog or derivative of cholecystokinin that exhibits at least one hormonal activity, or a fragment of an analog or derivative of cholecystokinin that exhibits at least one hormonal activity, and the at least one other peptide.

In a further alternative embodiments the at least one component peptide that exhibits at least one hormonal activity of a component peptide is glucagon-like peptide 2, a fragment of glucagon-like peptide 2 that exhibits at least one hormonal activity, an analog or derivative of glucagon-like peptide 2 that exhibits at least one hormonal activity, or a fragment of an analog or derivative of glucagon-like peptide 2 that exhibits at least one hormonal activity, and the at least one other peptide.

In a further alternative embodiments the at least one component peptide that exhibits at least one hormonal activity of a component peptide is oxyntomodulin, a fragment of oxyntomodulin that exhibits at least one hormonal activity, an analog or derivative of oxyntomodulin that exhibits at least one hormonal activity, or a fragment of an analog or derivative of oxyntomodulin that exhibits at least one hormonal activity, and the at least one other peptide.

In a further alternative embodiments the at least one component peptide that exhibits at least one hormonal activity of a component peptide is a natriuretic peptide, a fragment of a natriuretic peptide that exhibits at least one hormonal activity, an analog or derivative of a natriuretic peptide that exhibits at least one hormonal activity, or a fragment of an analog or derivative of a natriuretic peptide that exhibits at least one hormonal activity, and the at least one other peptide.

In a further alternative embodiments the at least one component peptide that exhibits at least one hormonal activity of a component peptide is exendin-4, a fragment of exendin-4 that exhibits at least one hormonal activity, an analog or derivative of exendin-4 that exhibits at least one hormonal activity, or a fragment of an analog or derivative of exendin-4 that exhibits at least one hormonal activity, and the at least one other peptide.

In certain embodiments, the GIP component portion of the Peptide of the Invention is combined with an amylin receptor ligand; or a Glucagon-like peptide 1 receptor ligand.

In other embodiments, the GIP portion of the Peptide of the Invention is combined with an EGF receptor ligand; a calcitonin receptor ligand; a CGRP receptor ligand, a gastrin/CCK receptor ligand; a keratinocyte growth factor (KGF) receptor 1 ligand; a dipeptidyl peptidase IV inhibitor; a REG protein receptor ligand; a Growth Hormone receptor ligand; a Prolactin (PRL) receptor ligand; an Insulin-like Growth Factor (IGF) receptor ligand; PTH-related protein (PTHrP) receptor ligand; hepatocyte growth factor (HGF) receptor ligand; an oxytocin receptor ligand, a fibroblast growth factor 19 (FGF19) receptor ligand; a fiboblast growth factor 21 (FGF21) receptor ligand; a bone morphogenetic protein (BMP) receptor ligand, a transforming growth factor (TGF receptor ligand; a laminin receptor ligand; a vasoactive intestinal peptide (VIP) receptor ligand; a fibroblast growth factor (FGF) receptor ligand; a nerve growth factor (NGF) receptor ligand; an islet neogenesis associated protein (INGAP) receptor ligand; an Activin-A receptor ligand; a vascular endothelial growth factor (VEGF) receptor ligand; an erythropoietin (EPO) receptor ligand; a pituitary adenylate cyclase activating polypeptide (PACAP) receptor ligand; a granulocyte colony stimulating factor (G-CSF) receptor ligand; a granulocyte-macrophage colony stimulating factor (GM-CSF); a platelet-derived growth factor (PDGF) receptor ligand, a cannabinoid CB1 receptor antagonist, and a secretin receptor ligand.

In another embodiment, the GIP peptide component included in the Peptides of the Invention includes an N-terminal GIP or novel GIP analog fragment in combination with a C-terminal peptide or fragment thereof having a glucose lowering activity (e.g., antidiabetics, amylin) or the ability to inhibit or reduce gastric emptying. Such GIP Peptides of the Invention include an N-terminal GIP fragment or novel GIP analog or derivative fragment in combination with amylin, gastrin, PYY, secretin, CCK, GRP, neuromedins, urocortin, a C-terminal, calcitonin or salmon calcitonin, a natriuretic peptide (e.g., ANP, BNP, CNP, urodilatin) or analog (e.g. amylin-sCT-amylin chimera), derivative or fragment thereof.

In other embodiments, the GIP peptide component included within the Peptides of the Invention include a C-terminal GIP or novel GIP analog fragment in combination with an N-terminal polypeptide or fragment thereof having a glucose lowering activity (e.g., antidiabetics, amylin) or the ability to inhibit or reduce gastric emptying. In such embodiments, the chimeric peptides can include a C-terminal GIP, a novel GIP analog, or fragment thereof, in combination with a N-terminal exendin, GLP-1, amylin, CCK, gastrin, PYY, secretin, GRP, neuromedins, urocortin, calcitonin, or salmon calcitonin, a natriuretic peptide or analog, derivative or fragment thereof.

In one embodiment, the Peptides of the Invention include a heterologous C-terminal tail or terminal extension to the GIP portion. As with the other GIP peptides described herein, in one embodiment of the Peptides of the Invention, the GIP portion can be native GIP, an active fragment thereof, or their analogs or derivatives. In another aspect the GIP component of the Peptides of the Invention comprises at least one modification, substitution, deletion or addition that provides one or more enhanced properties, e.g. increased resistance to proteolytic digestion (thus prolonging half-life), fatty acyl derivatization that reduces renal clearance. In one embodiment, the tail comprises a Trp-cage motif sequence. In another embodiment the GIP analog peptide portion includes unnatural amino acids, such as a D amino acid, e.g. that inhibits or reduces the rate of proteolysis by DPP-IV.

The invention also encompasses using the Peptides of the Invention for the treatment and prevention of metabolic and liver diseases and disorders, particularly those which can be alleviated by control of food intake, weight loss, energy metabolism, plasma glucose levels, insulin levels, and/or insulin secretion, positive inotropic effects, reduction of catabolic effects, slowing of gastric emptying, obesity, diabetes and diabetes-related conditions, liver fat-associated inflammation and injury. Such conditions and disorders include, but are not limited to, hypertension, dyslipidemia, cardiovascular disease, eating disorders and rare genetic disorders of obesity such as Prader Willi Syndrome, critical care, insulin-resistance and disorders thereof such as polycystic ovary syndrome, obesity, diabetes mellitus of any kind, including type 1, type 2, and gestational diabetes, and CNS disorders such as preventing neurodegeneration, Alzheimer's disease and Parkinson's disease, and nonalcoholic steatohepatitis (NASH), as well as complications from diabetes (e.g. neuropathy (treating with a Peptide of the Invention including a GIP peptide containing an exendin family component for example), neuropathic pain (treating with a Peptide of the Invention including a GIP peptide comprising an amylin family hormone module for example), retinopathy, nephropathy, conditions of insufficient pancreatic beta cell mass (based on, e.g., islet neogenesis actions of exendin-4 and GLP-1).

Accordingly, provided are methods for treating or preventing such conditions, wherein the method comprises administering a therapeutically or prophylactically effective amount of a Peptide of the Invention. In certain embodiments, the Peptides of the Invention include GIP or an analog or derivative thereof, including a novel GIP analog of the invention, or a GIP Peptide of the Invention including one or more additional peptides or peptide fragments to a subject in need thereof.

In one embodiment the Peptides of the Invention can be provided as monotherapy. In another embodiment for treating obesity, diabetes or conditions associated with increased body weight or elevated glucose levels, the Peptides of the Invention can be administered in adjunct therapy with food intake reduction or glucose lowering agents (e.g., antidiabetics) or agents or methods that inhibit or reduce gastric emptying. Examples of such agents are presented herein. For example, in one embodiment is provided an adjunct therapy method for reducing body weight or blood glucose levels of a subject, e.g., one having obesity, type 1, type 2 or gestational diabetes mellitus, comprising administering to the subject a therapeutically effective amount of a Peptide of the Invention, such as wherein said agonist is a peptide including adjunct therapy with a GIP or novel GIP analog of the invention, or an effective amount of a GIP-GLP-1-amylin.

Peptides of the Invention, alone or in combination with a glucose lowering agent (e.g., antidiabetics) or with agents or methods that inhibit or reduce gastric emptying, can also be useful for potentiating, inducing, enhancing or restoring glucose responsivity in pancreatic islets or cells. These actions may also be used to treat or prevent conditions associated with metabolic disorders such as those described above.

In another embodiment, methods for treating or preventing obesity are provided, wherein the method comprises administering a therapeutically or prophylactically effective amount of a Peptide of the Invention to a subject in need thereof. In certain embodiments, the Peptide of the Invention includes GIP or an analog or derivative thereof, including a novel GIP analog of the invention, or a GIP-hybrid of the invention, for example, a GIP-GLP-1-amylin hybrid.

In another embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method. Peptides of the Invention can also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, Am. Fam. Phys. 63:2185, 2001). Where conditions are associated with elevated glucose or hyperglycemia, the method comprises administering a therapeutically or prophylactically effective amount of a Peptide of the Invention, alone or in combination with a glucose lowering agent (e.g., antidiabetic) or agent or method that inhibits or reduces gastric emptying.

In yet another aspect, Peptides of the Invention, particularly GIP hybrids of the invention, can be used in methods of reducing food intake, reducing appetite, inducing satiety, reducing nutrient availability, reducing caloric efficiency, causing weight loss, affecting body composition, altering body energy content or energy expenditure, and improving lipid profile (including reducing LDL cholesterol and triglyceride levels and/or changing HDL cholesterol levels) wherein the methods comprise administering to a subject an effective amount of a Peptide of the Invention, for example, a GIP hybrid of a Peptide of the Invention. In one embodiment, the methods of the invention are used to treat or prevent conditions or disorders, which can be alleviated by reducing nutrient availability in a subject in need thereof, comprising administering to said subject a therapeutically or prophylactically effective amount of a Peptide of the Invention.

Conditions and disorders include, but are not limited to, control of food intake, weight loss, energy metabolism, plasma glucose levels, insulin levels, and/or insulin secretion, positive inotropic effects, reduction of catabolic effects, slowing of gastric emptying, obesity, diabetes and diabetes-related conditions, liver fat-associated inflammation and injury. Such conditions and disorders include, but are not limited to, hypertension, dyslipidemia, cardiovascular disease, eating disorders and rare genetic disorders of obesity such as Prader Willi Syndrome, critical care, insulin-resistance and disorders thereof such as polycystic ovary syndrome, obesity, diabetes mellitus of any kind, including type 1, type 2, and gestational diabetes, and CNS disorders such as preventing neurodegeneration, Alzheimer's disease and Parkinson's disease, and nonalcoholic steatohepatitis (NASH), diabetes complications (neuropathy (based on, e.g., neurotrophic actions of exendin-4), neuropathic pain (based on, e.g., amylin action), retinopathy, nephropathy, conditions of insufficient pancreatic beta cell mass (based on, e.g., islet neogenesis actions of exendin-4 and GLP-1). Where conditions are associated with elevated glucose or hyperglycemia, the method comprises administering a therapeutically or prophylactically effective amount of a Peptide of the Invention, alone or in combination with a glucose lowering agent (e.g., antidiabetic) or agent or method that inhibits or reduces gastric emptying.

In addition to the amelioration of hypertension in subjects in need thereof as a result of reduced food intake, weight loss, and/or treating obesity, Peptides of the Invention may be used to treat or prevent hypotension and conditions associated therewith.

The Peptides of the Invention, for example, GIP components, include extended half-life GIP hybrids (e.g. DPP-IV cleavage resistant such as a D-Tyrl, D-Ala2, N-Acetyl or N-pyroglutamyl analogs) optionally further comprising a peptide such as a heterologous C-terminal tail. The Peptides of the Invention comprise other hormone modules known to provide beneficial cardiovascular effects and are useful to treat cardiovascular disease and related conditions. As disclosed herein, the Peptides of the Invention increase cardiac contractility (dp/dt), decrease blood pressure (for example by acute vasodilatation), decrease systolic pressure, decrease diastolic pressure, and can provide a direct beneficial action on cardiac cells. The Peptides of the Invention also improve cardiac function via metabolic actions, e.g. body weight reduction glucose lowering, insulin secretion, beta cell proliferation. However, by also providing direct effects on cardiovascular system, the Peptides of the Invention are surprisingly even more beneficial.

Peptides of the Invention are also useful in the treatment or prevention of any number of gastrointestinal disorders that are associated with excess gastric secretion, excess intestinal electrolytes and water secretion as well as decreased absorption, e.g., infectious (e.g., viral or bacterial) diarrhea, inflammatory diarrhea, short bowel syndrome, or the diarrhea which typically occurs following surgical procedure, e.g., ileostomy (see e.g., Harrison's principles of Internal Medicine, McGraw Hill Inc., New York, 12th ed.). Examples of infectious diarrhea include, without limitation, acute viral diarrhea, acute bacterial diarrhea (e.g., *salmonella, campylobacter*, and *clostridium*) or diarrhea due to protozoal infections, or travelers' diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. GIP and GIP compounds of the invention can be used to treat or prevent an emergency or life-threatening situation involving a gastrointestinal disorder, e.g., after surgery or due to cholera. Furthermore, the compounds can be used to treat intestinal dysfunction in patients with Acquired Immune Deficiency Syndrome (AIDS), especially during cachexia.

The Peptides of the Invention are also useful for inhibiting small intestinal fluid and electrolyte secretion, and augmenting nutrient transport, as well as increasing cell proliferation in the gastrointestinal tract, regulating lipolysis in, e.g., adipose tissue and regulating blood flow in a mammal. The Peptides of the Invention are useful for treating or preventing the above conditions by their gastrointestinal protective activity (e.g., inhibition of gastric secretion). Accordingly, a Peptide of the Invention may be used to treat gastrointestinal or mucosal damage. Exemplary types of damage include, but are not limited to, inflammatory bowel disease, bowel atrophy, conditions characterized by loss of bowel mucosa or bowel mucosal function, and other conditions of the gastrointestinal tract, including those which may be brought about by exposure to cytotoxic agents, radiation, toxicity, infection and/or injury. Moreover, the Peptides of the Invention may be combined with analgesics, anti-inflammatory agents, growth hormone, heparin, or any other therapies that may be used to treat inflammatory bowel disease or other conditions listed above.

In another embodiment, the Peptides of the Invention are useful for treating or preventing gastritis, pancreatitis, Barrett's esophagus, Gastroesophageal Reflux Disease (GERD) and conditions associated therewith. Such conditions can include, but are not limited to, heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), and pulmonary aspiration. In certain embodiments, the Peptides of the Invention can have anti-secretory properties, such as inhibition of gastric acids, inhibition of bile acids, and inhibition of pancreatic enzymes. Moreover, the Peptides of the Invention can also have gastroprotective effects. Accordingly, the Peptides of the Invention may be particularly useful in the treatment or prevention of gastritis, pancreatitis, Barrett's esophagus, and/or GERD and related or associated conditions.

The invention also relates to pharmaceutical compositions comprising a therapeutically or prophylactically effective amount of at least one Peptide of the Invention, or a pharmaceutically acceptable salt thereof, together with pharmaceutically acceptable diluents, preservatives, solubilizers, emulsifiers, adjuvants and/or carriers useful in the delivery of the Peptides of the Invention.

These and other aspects of the invention will be more clearly understood with reference to the following embodiments and detailed description.

The invention encompasses Peptides of the Invention or a pharmaceutically acceptable salt or solvate thereof, wherein in certain embodiments, the Peptides of the Invention comprise, consist essentially of, or consist of an amino acid sequence of Formula (I):

$X^1$-$X^2$-E-G-T-F-$X^3$-S-D-Y-S-I-$X^4$-$X^5$-D-K-I-$X^6$-Q-$X^7$-$X^8$-F-V-$X^9$-W-L-$X^{10}$-$X^{11}$-$X^{12}$-$X^{13}$ $X^{14}$-$X^{15}$-$X^{16}$-C-N-T-A-T-C-$X^{17}$-$X^{18}$-$X^{19}$-$X^{20}$-L-$X^{21}$-$X^{22}$-$X^{23}$-L-$X^{24}$-$X^{25}$-$X^{26}$-$X^{27}$-$X^{28}$-$X^{29}$ $X^{30}$-$X^{31}$-$X^{32}$-$X^{33}$ $X^{34}$-P-$X^{35}$-T-N-$X^{36}$-G-$X^{37}$-N-T-Y-($NR^1R^2$) (SEQ ID NO: 23)

(I)

wherein $X^1$ is Tyr or (d) Tyr;
$X^2$ is Ala, (d) Ala, or Aib;
$X^3$ is Ile or Thr;
$X^4$ is Ala, Aib, or Gln;
$X^5$ is Met, Leu, or Val;
$X^6$ is Ala or His;
$X^7$ is Gln, Lys, or Lys-γ-Glu-γ-Glu-C═O$(CH_2)_nR^3$;
$X^8$ is Ala or Asp;
$X^9$ is Asn or Gln;
$X^{10}$ is Leu or Ile;
$X^{11}$ is Ala or Val;
$X^{12}$ is Gly or Gln;
$X^{13}$ is Gly, Lys, Arg, Ser, or Lys-γ-Glu-γ-Glu-C═O$(CH_2)_nR^3$;
$X^{14}$ is Pro, Gly, Lys, or Lys-γ-Glu-γ-Glu-C═O$(CH_2)_nR^3$;
$X^{15}$ is Ser, Gly, Lys, or Lys-γ-Glu-γ-Glu-C═O$(CH_2)_nR^3$;
$X^{16}$ is absent or is Gly or Ser;
$X^{17}$ is Ala, Met or Val;
$X^{18}$ is Thr or Leu;
$X^{19}$ is Gln or Gly;
$X^{20}$ is Arg, Lys, or Gln;
$X^{21}$ is Ala or Ser;
$X^{22}$ is Asn or Gln;
$X^{23}$ is Phe or Glu;
$X^{24}$ is His or Val;

$X^{25}$ is His or Arg;
$X^{26}$ is Ser or Leu;
$X^{27}$ is Ser or Gln;
$X^{28}$ is Asn or Thr;
$X^{29}$ is absent or is Asn or Gln;
$X^{30}$ is absent or is Phe;
$X^{31}$ is absent or is Gly;
$X^{32}$ is absent or is Pro;
$X^{33}$ is absent or is Ile, Lys, or Lys-γ-Glu-γ-Glu-C═O$(CH_2)_nR^3$;
$X^{34}$ is Leu or Tyr;
$X^{35}$ is Pro, Lys Arg, or Lys-γ-Glu-γ-Glu-C═O$(CH_2)_nR^3$;
$X^{36}$ is Val or Thr; and
$X^{37}$ is Ser, Lys, or Lys-γ-Glu-γ-Glu-C═($(CH_2)_nR^3$,
wherein
$R^1$ and $R^2$ are each independently H or $C_{1-5}$ alkyl,
$R^3$ is —$CO_2H$, —$CO_2CH_3$, —$CO_2NH_2$, —$CO_2NHCH_3$, —$CO_2N(CH_3)_2$, —$CH_3$, or —$NH_2$,
n is an integer from 12-20.

In particular embodiments, any of the Peptides of the Invention described herein comprise one or more half-life extension moiety and/or one or more linker moieties conjugated to the peptide. In particular embodiments, the half-life extension moiety is conjugated to the peptide component of the Peptide of the Invention via one or more linker moieties.

In certain embodiments, any of the Peptides of the Invention described herein further comprise a conjugated chemical substituent. In particular embodiments, the conjugated chemical substituent is a lipophilic substituent or a polymeric moiety, e.g., Ac, Palm, gamma-Glu-Palm, isoGlu-Palm, PEG2-Ac, PEG4-isoGlu-Palm, (PEG) 5-Palm, succinic acid, glutaric acid, pyroglutaric acid, benzoic acid, IVA, octanoic acid, 1,4 diaminobutane, isobutyl, Alexa488, Alexa647, or biotin. In certain embodiments, the conjugated chemical substituent is a polyethylene glycol with a molecular mass of 400 Da to 40,000 Da.

In a related aspect, the present invention includes a Peptide of the Invention comprising at least two peptide components connected via one or more linker moieties, wherein each peptide subunit comprises a sequence of Formula (I)-(V) or any other sequence or structure set forth herein. In certain embodiments, the linker is any of those described herein. In certain embodiments, the linker moiety is a diethylene glycol linker, an iminodiacetic acid (IDA) linker, a β-Ala-iminodiaceticacid (B-Ala-IDA) linker, or a PEG linker. In certain embodiments, the PEG linker is a polyethylene glycol with a molecular mass of 400 Da to 40,000 Da. In certain embodiments, the linker is a Fc protein molecule. In particular embodiments, the N-terminus of each peptide monomer subunit is connected by the linker moiety. In particular embodiments, the C-terminus of each peptide monomer subunit is connected by the linker moiety. In other embodiments, the linker connects an internal amino acid residue of at least one of the peptide components to the N-terminus, C-terminus, or an internal amino acid residue of another peptide component.

In a further related embodiment, the invention includes a sequence encoding a Peptide of the Invention or one or more peptide subunits of a Peptide of the Invention. The present invention also includes a vector comprising the polynucleotide.

In another aspect, the invention includes a pharmaceutical composition comprising a Peptide of the Invention, and a pharmaceutically acceptable carrier, excipient, or diluent. In particular embodiments, the pharmaceutical composition comprises an enteric coating. In certain embodiments, the enteric coating protects and releases the pharmaceutical composition within a subject's gastrointestinal system.

In certain embodiments, the pharmaceutical composition is provided to the subject by an oral, intravenous, peritoneal, intradermal, subcutaneous, intramuscular, intrathecal, inhalation, vaporization, nebulization, sublingual, buccal, parenteral, rectal, intraocular, inhalation, vaginal, or topical route of administration. In certain embodiments, the pharmaceutical composition is provided to the subject topically, parenterally, intravenously, subcutaneously, peritoneally, or intravenously for treating obesity.

DETAILED DESCRIPTION OF THE INVENTION

Definitions

Figure 1A:
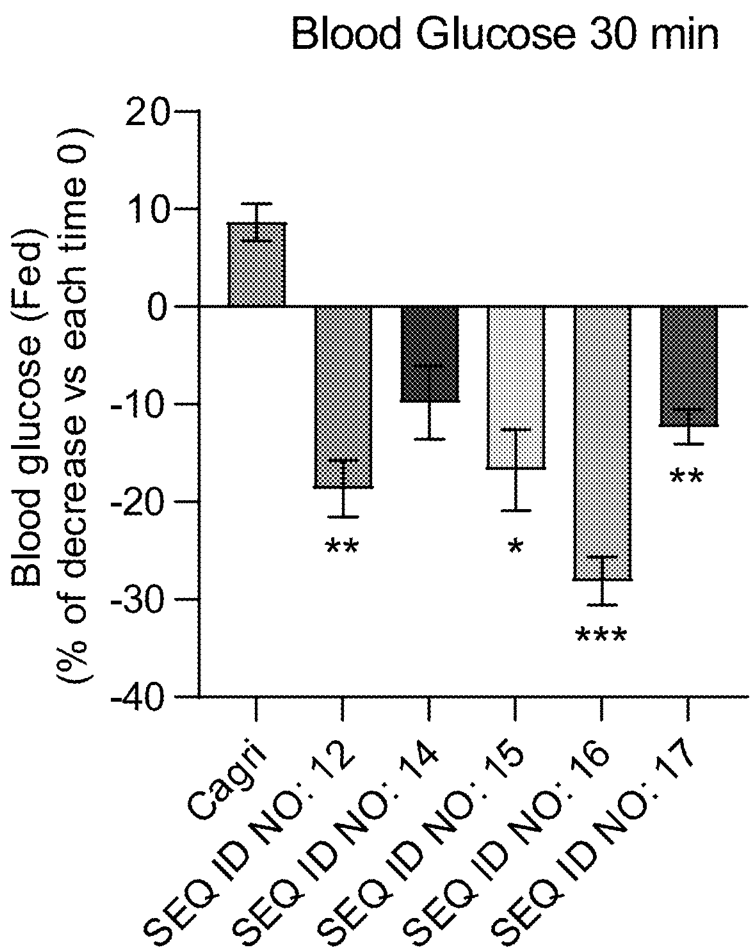
FIGS. 1A and 1B illustrates reduction of blood glucose after single administration of exemplary peptides of the invention. Blood glucose was measured after 30 minutes (FIG. 1A) or 120 minutes (FIG. 1B).

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

Throughout this specification, the word "comprise" or variations such as "comprises" or "comprising" will be understood to imply the inclusion of a stated component(s) or group of component(s), but not the exclusion of any other components or group of components.

The singular forms "a," "an," and "the" include the plurals unless the context clearly dictates otherwise.

The term "including" is used to mean "including but not limited to." "Including" and "including but not limited to" are used interchangeably.

The term "hybrid" is used to mean a peptide that includes combinations or portions of two or more peptides, for example, GLP-1-GIP-amylin; or GIP-amylin.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term "peptide," as used herein, refers broadly to a sequence of two or more amino acids joined together by peptide bonds. It should be understood that this term does not connote a specific length of a polymer of amino acids, nor is it intended to imply or distinguish whether the polypeptide is produced using recombinant techniques, chemical or enzymatic synthesis, or is naturally occurring. The term peptide also includes cyclic peptides.

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, considering the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna. CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4:11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215:403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. Another example of a conservative substitution with a residue normally not found in endogenous, mammalian peptides and proteins is the conservative substitution of Arg or Lys with, for example, ornithine, canavanine, aminoethylcysteine or another basic amino acid. In some embodiments, one or more cysteines of a peptide analogue of the invention may be substituted with another residue, such as a serine. For further information concerning phenotypically silent substitutions in peptides and proteins, see, for example, Bowie et.al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|---|---|---|---|
| A | N | H | M | F |
| S | D | R | L | Y |
| T | E | K | I | W |
| P | Q | | V | |
| G | | | C | |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|---|---|---|---|---|
| A | E | H | M | F |
| L | D | R | S | Y |
| I | | K | T | W |
| P | | | C | |
| G | | | N | |
| V | | | Q | |

The term "amino acid" or "any amino acid" as used here refers to any and all amino acids, including naturally occurring amino acids (e.g., a-amino acids), unnatural amino acids, modified amino acids, and non-natural amino acids. It includes both D- and L-amino acids. Natural amino acids include those found in nature, such as, e.g., the 23 amino acids that combine into peptide chains to form the building-blocks of a vast array of proteins. These are primarily L stereoisomers, although a few D-amino acids occur in bacterial envelopes and some antibiotics. The 20 "standard," natural amino acids are listed in the above tables. The "non-standard," natural amino acids are pyrrolysine (found in methanogenic organisms and other eukaryotes), selenocysteine (present in many noneukaryotes as well as most eukaryotes), and N-formylmethionine (encoded by the start codon AUG in bacteria, mitochondria and chloroplasts). "Unnatural" or "non-natural" amino acids are non-proteinogenic amino acids (i.e., those not naturally encoded or found in the genetic code) that either occur naturally or are chemically synthesized. Over 140 unnatural amino acids are known and thousands of more combinations are possible. Examples of "unnatural" amino acids include β-amino acids ($\beta^3$ and $\beta^2$), homo-amino acids, proline and pyruvic acid derivatives, 3-substituted alanine derivatives, glycine derivatives, ring-substituted phenylalanine and tyrosine derivatives, linear core amino acids, diamino acids, D-amino acids, alpha-methyl amino acids and N-methyl amino acids. Unnatural or non-natural amino acids also include modified amino acids. "Modified" amino acids include amino acids (e.g., natural amino acids) that have been chemically modified to include a group, groups, or chemical moiety not naturally present on the amino acid. According to certain embodiments, a peptide comprises an intramolecular bond between two amino acid residues present in the peptide. It is understood that the amino acid residues that form the bond will be altered somewhat when bonded to each other as compared to when not bonded to each other. Reference to a particular amino acid is meant to encompass that amino acid in both its unbonded and bonded state. For example, the amino acid residue homoSerine (hSer) or homoSerine(Cl) in its unbonded form may take the form of 2-aminobutyric acid (Abu) when participating in an intramolecular bond according to the present invention.

Typically, the names of naturally occurring and non-naturally occurring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)" Biochemistry, 14 (2), (1975). To the extent that the names and abbreviations of amino acids and aminoacyl residues employed in this specification and appended claims differ from those suggestions, they will be made clear to the reader. Some abbreviations useful in describing the invention are defined below in the following Table 1.

TABLE 1

Abbreviations of exemplary Non-Natural Amino Acids and Chemical Moieties (for amino acid derivatives)

| Abbreviation | Definition |
|---|---|
| (1-Me)His | (1-Methyl)Histidine |
| (d)(N-Me)Tyr | NMe(d)Tyr or N-Me-(d)Tyrosine |
| (d)Tyr | (d)Tyrosine |
| (d)aMePhe | (d)-alpha-Me-Phenylalanine |
| (d)aMeTyr | (d)-alpha-Me-Tyrosine |
| (N-benzyl)Asn | N-benzyl-Asparagine |
| (N-Ph)Asn | N-Ph-Asparagine |
| 4-Aba | 4-Aminobenzoic Acid |
| 4-Ana | 4-amino-naphthalene-1-carboxylic acid |
| 6-Ana | 6-amino-naphthalene-1-carboxylic acid |
| Abu | 2-Aminobutyric acid |
| Ac- | Acetyl |
| AEP | 3-(2-aminoethoxy)propanoic acid |
| Ahx | 6-aminohexanoic acid |
| Aib | 2-aminoisobutyric acid |
| α-MeAsn, alpha-MeAsn | α-Methyl-L-Asparagine |
| α-MeGln, alpha-MeGln | α-Methyl-L-Glutamine |
| α-MeGlu or αMeGlu | alpha-Methyl Glutamic Acid |
| α-MePhe(4-F) | alpha-Methyl-(4-Fluoro)phenylalanine |
| α-MePro | alpha-Methyl-L-Proline |
| $CONH_2$ | Carboxamide |
| COOH | Carboxylic Acid |
| His_3Me or 3MeHis | (3-Methyl)Histidine |
| hArg | L-homoArginine |
| hLeu | L-homoLeucine |
| hLys(Ac) or homo-Lys(Ac), | homo-L-Lysine |
| Hph | Homophenylalanine |
| hPhe(3,4-dimethoxy) | 3,4-dimethoxy-L-homophenylalanine |
| hSer | L-homoSerine |
| Hy | Hydrogen (Free N-terminal) |
| Hyp | 4-Hydroxy-L-Proline |
| iPr or i-Pr | Iso-Propyl |
| Lys(Ac) | N-a-acetyl-L-Lysine |
| Lys(CO2Allyl) | N-(C(O)2-Allyl)-Lysine |
| Lys($COCF_3$) | N-a-trifluoroacetyl-L-Lysine |
| Lys(COCF3) | N-Trifluoroacetyl-Lysine |
| Lys(COcPr) | Lys(CO-cyclopropyl) |
| Lys(COEt) | N-(C(O)-Et)-Lysine |
| Lys(COiBu) | N-ε-[C(O)-i-Bu]-L-Lysine |
| Lys(COiPr) | N-(C(O)-i-Pr)-Lysine |
| Lys(COPent) | Lys(CO-pentyl) |
| Lys(COPr) | N-(C(O)-n-Pr)-Lysine |
| Lys(COtBu) | N-ε-[C(O)-t-Bu]-L-Lysine |
| Lys(COtBu) | N-(C(O)-t-Bu)-Lysine |
| Lys(isobutyl,Ac) | $N^{\varepsilon}$-acetyl-$N^{\varepsilon}$-isobutyl-L-Lysine or Lys(N-acetyl-N-isobutyl) |

TABLE 1-continued

| Abbreviations of exemplary Non-Natural Amino Acids and Chemical Moieties (for amino acid derivatives) | |
|---|---|
| Abbreviation | Definition |
| | 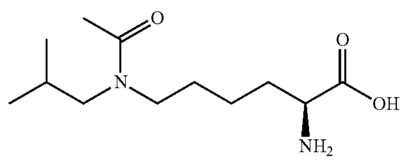 [SMILES: CC(=O)N(CCCC[C@H](N)C(=O)O)CC(C)C] |
| Lys(propyl,Ac) | $N^{\varepsilon}$-acetyl-$N^{\varepsilon}$-propyl-L-Lysine or Lys(N-acetyl-N-propyl) 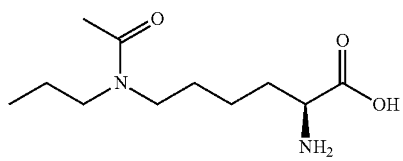 [SMILES: CCCN(CCCC[C@H](N)C(=O)O)C(C)=O] |
| Lys(R') | N-ε-[R']-L-Lysine (exemplary R' = Aib, bAla, IVA, Ala, cyclohexanoic, octanoic, —$C(O)CH_2Ph$, trifluoropropionic, Gly, acetyl, trifluoroacetyl, etc) |
| 2-Nal | 2-naphthyl-alanine |
| N(NBu) | N-butyl-L-asparagine (L-asparagine, N-butyl) |
| N(NBzl) | N-benzyl-L-asparagine (L-asparagine, N-benzyl) |
| N(Nchx) | N-cyclohexyl-L-asparagine (L-asparagine, N-cyclohexy1) |
| N(Ncpx) | N-cyclopropyl-L-asparagine (L-asparagine, N-cyclopropyl) |
| N(NEt) | N-ethyl-L-asparagine (L-asparagine, N-ethyl) |
| N(NiBu) | N-isobutyl-L-asparagine (L-asparagine, N-isobutyl) |
| N(NiPr) | N-isopropyl-L-asparagine (L-asparagine, N-isopropyl) |
| N(NMe) | N-methyl-L-asparagine (L-asparagine, N-methyl) |
| N-MeAla | N-Methyl-L-Alanine |
| N-MeArg | N-Methyl-L-Arginine |
| N-MeAsn | N-Methyl-L-Asparagine |
| N-MeGln | N-Methyl-L-Glutamine |
| N-MeLys | N-Methyl-Lysine |
| N-Me-Lys | N-Methyl-L-Lysine |
| N-Me-Lys(Ac) | N-ε-Acetyl-N-Methyl-L-lysine |
| N-MeTrp | N-Methyl-L-Tryptophan |
| NMeβA or NMebA | N-Methyl-beta-Alanine |
| Sarc or NMeGly | Sarcosine or N-methylglycine |
| t-butyl-Ala | 3-(tert-butyl)-L-Alanine-OH |
| t-butyl-Gly | tert-butyl-glycine |
| Tyr(3-t-Bu) | 3-t-butyl-L-tyrosine |
| α-MeArg, a-MeArg, or alpha-MeArg | alpha-methyl-L-Arginine |
| α-MeCys, alpha-MeCys, or a-MeCys | alpha-methyl-L-Cysteine |
| α-MeLeu, a-MeLeu, alpha-MeLeu | alpha-methyl-L-Leucine |
| α-MeLys(Ac), a-MeLys(Ac), or alpha-MeLys(Ac) | ε-acetyl-alpha-methyl-L-Lysine |
| α-MeLys, a-MeLys, or alpha-MeLys | alpha-methyl-L-Lysine |
| α-MeOrn | alpha-methyl-L-Ornithine |
| α-MePhe or a-MePhe or a-Me-Phe | alpha-methyl-L-Phenylalanine |
| α-MeTrp | alpha-methyl-L-Tryptophan |
| α-MeTyr | alpha-methyl-L-Tyrosine |
| α-DiethylGly | a-DiethylGlycine |
| βAla, beta-Ala, or bA | beta-Alanine |

Single letter and three letter abbreviations for naturally occurring amino acids described in the invention are defined below in the following Table 2.

TABLE 2

| Naturally Occurring Amino Acids | | |
|---|---|---|
| Amino Acid | Three letter Code | One letter Code |
| Alanine | Ala | A |
| Cysteine | Cys | C |
| Aspartic Acid | Asp | D |
| Glutamic Acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

Throughout the present specification, unless naturally occurring amino acids are referred to by their full name (e.g., alanine, arginine, etc.), they are designated by their conventional three-letter or single-letter abbreviations (e.g., Ala or A for alanine, Arg or R for arginine, etc.). Unless otherwise indicated, three-letter and single-letter abbreviations of amino acids refer to the L-isomeric form of the amino acid in question. The term "L-amino acid," as used herein, refers to the "L" isomeric form of a peptide, and conversely the term "D-amino acid" refers to the "D" isomeric form of a peptide (e.g., Dasp, (d) Asp or D-Asp; Dphe, (d) Phe or D-Phe). Amino acid residues in the D isomeric form can be substituted for any L-amino acid residue, as long as the desired function is retained by the peptide. D-amino acids may be indicated as customary in lower case when referred to using single-letter abbreviations.

In the case of less common or non-naturally occurring amino acids, unless they are referred to by their full name (e.g. sarcosine, ornithine, etc.), frequently employed three- or four-character codes are employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (γ-glutamic acid), Gaba (γ-aminobutanoic acid), β-Pro (pyrrolidine-3-carboxylic acid), and 8Ado (8-amino-3,6-dioxaoctanoic acid), Abu (2-amino butyric acid), βhPro (β-homoproline), βhPhe(β-homophenylalanine) and Bip (β,β diphenylalanine), and Ida (Iminodiacetic acid).

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-" moiety at the amino terminus (N-terminus) of the sequence, and either an "—OH" moiety or an "—$NH_2$" moiety at the carboxy terminus (C-terminus) of the sequence. In such cases, and unless otherwise indicated, a "Hy-" moiety at the N-terminus of the sequence in question indicates a hydrogen atom, corresponding to the presence of a free primary or secondary amino group at the N-terminus, while an "—OH" or an "—$NH_2$" moiety at the C-terminus of the sequence indicates a hydroxy group or an amino group, corresponding to the presence of an amido ($CONH_2$) group at the C-terminus, respectively. In each sequence of the invention, a C-terminal "—OH" moiety may be substituted for a C-terminal "—$NH_2$" moiety, and vice-versa.

One of skill in the art will appreciate that certain amino acids and other chemical moieties are modified when bound to another molecule. For example, an amino acid side chain may be modified when it forms an intramolecular bridge with another amino acid side chain, e.g., one or more hydrogen may be removed or replaced by the bond. Accordingly, as used herein, reference to an amino acid or modified amino acid present in a Peptide of the Invention is meant to include the form of such amino acid or modified amino acid present in the peptide both before and after forming the intramolecular bond.

The term "$NH_2$," as used herein, can refer to a free amino group present at the amino terminus of a polypeptide. The term "OH," as used herein, can refer to a free carboxy group present at the carboxy terminus of a peptide. Further, the term "Ac," as used herein, refers to Acetyl protection through acylation of the C- or N-terminus of a polypeptide. In certain peptides shown herein, the $NH_2$ locates at the C-terminus of the peptide indicates an amino group.

The term "carboxy," as used herein, refers to-$CO_2H$.

The term "isostere replacement," as used herein, refers to any amino acid or other analog moiety having chemical and/or structural properties similar to a specified amino acid. In certain embodiments, an isostere replacement is a conservative substitution or an analog of a specified amino acid.

The term "cyclized," as used herein, refers to one part of a peptide molecule being linked to another part of the peptide molecule to form a closed ring, such as by forming a disulfide bridge or thioether bond.

The terms "component" or "subunit," are used interchangeably and refer to one of a pair of peptide monomers that are joined to form a Peptide of the Invention.

The term "linker moiety," as used herein, refers broadly to a chemical structure that is capable of linking or joining together two peptide subunits.

The term "pharmaceutically acceptable salt," as used herein, represents salts or zwitterionic forms of the peptides or Peptides of the Invention, which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quarternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. A pharmaceutically acceptable salt may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type $N(R_1)(R_2)(R_3)(R_4)+$, wherein each of $R_1$, $R_2$, $R_3$ and $R_4$ independently will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66:2 (1977). Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts.

The term "N(alpha) Methylation" as used herein, describes the methylation of the alpha amine of an amino acid, also generally termed as an N-methylation.

The term "symmethylation" or "Arg-Me-sym" as used herein, describes the symmetrical methylation of the two nitrogens of the guanidine group of arginine. Further, the term "asym methylation" or "Arg-Me-asym" describes the methylation of a single nitrogen of the guanidine group of arginine.

The term "acylating organic compounds" as used herein refers to various compounds with carboxylic acid functionality that are used to acylate the N-terminus of an amino acid or a peptide component, e.g., a monomer subunit prior to forming a C-terminal dimer. Non-limiting examples of acylating organic compounds include cyclopropylacetic acid, 4-Fluorobenzoic acid, 4-fluorophenylacetic acid, 3-Phenylpropionic acid, Succinic acid, Glutaric acid, Cyclopentane carboxylic acid, 3,3,3-trifluoropropeonic acid, 3-Fluoromethylbutyric acid, Tetrahedro-2H-Pyran-4-carboxylic acid.

The term "alkyl" includes a straight chain or branched, noncyclic or cyclic, saturated aliphatic hydrocarbon containing from 1 to 24 carbon atoms. Representative saturated straight chain alkyls include, but are not limited to, methyl, ethyl, n-propyl, n-butyl, n-pentyl, n-hexyl, and the like, while saturated branched alkyls include, without limitation, isopropyl, sec-butyl, isobutyl, tert-butyl, isopentyl, and the like. Representative saturated cyclic alkyls include, but are not limited to, cyclopropyl, cyclobutyl, cyclopentyl, cyclohexyl, and the like, while unsaturated cyclic alkyls include, without limitation, cyclopentenyl, cyclohexenyl, and the like.

"Halo" or "halogen" refers to bromo (Br), chloro (Cl), fluoro (F) or iodo (I) substituents.

The terms "haloalkyl" includes alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

An "alkoxy" group refers to a (alkyl)O-group, where alkyl is as defined herein.

An "aryloxy" group refers to an (aryl)O-group, where aryl is as defined herein.

"Aminocarbonyl" or "carboxamido" refers to a $—CONH_2$ radical.

"2-Aminoethoxy" refers to $—OCH_2CH_2—NH_2$ radical.

"2-Acetylaminoethoxy" refers to $—OCH_2CH_2—N(H)C(O)Me$ radical.

The term "mammal" refers to any mammalian species such as a human, mouse, rat, dog, cat, hamster, guinea pig, rabbit, livestock, and the like.

As used herein, a "therapeutically effective amount" of a Peptide of the Invention is meant to describe a sufficient amount to treat or prevent any of the diseases and disorders described herein (for example, to treat obesity). In particular embodiments, the therapeutically effective amount will achieve a desired benefit/risk ratio applicable to any medical treatment.

An "analog" of an amino acid, e.g., a "Phe analog" or a "Tyr analog" means an analog of the referenced amino acid. A variety of amino acid analogs are known and available in the art, including Phe and Tyr analogs. In certain embodiments, an amino acid analog, e.g., a Phe analog or a Tyr analog comprises one, two, three, four or five substitutions as compared to Phe or Tyr, respectively. In certain embodiments, the substitutions are present in the side chains of the amino acids. In certain embodiments, a Phe analog has the structure $Phe(R^2)$, wherein $R^2$ is a Hy, OH, $CH_3$, $CO_2H$, $CONH_2$, $CONH_2OCH_2CH_2NH_2$, t-Bu, $OCH_2CH_2NH_2$, phenoxy, $OCH_3$, OAllyl, Br, Cl, F, $NH_2$, $N_3$, or guanadino. In certain embodiments, $R^2$ is $CONH_2OCH_2CH_2NH_2$, $OCH_3$, $CONH_2$, $OCH_3$ or $CO_2H$. Examples of Phe analogs include, but are not limited to: hPhe, Phe(4-OMe), $\alpha$-Me-Phe, hPhe(3,4-dimethoxy), Phe(4-$CONH_2$), Phe(4-phenoxy), Phe(4-guanadino), Phe(4-tBu), Phe(4-CN), Phe(4-Br), Phe(4-OBzl), Phe(4-$NH_2$), BhPhe(4-F), Phe(4-F), Phe (3,5 DiF), Phe($CH_2CO_2H$), Phe(penta-F), Phe(3,4-Cl2), Phe (3,4-F2), Phe(4-CF3), BB-diPheAla, Phe(4-$N_3$), Phe [4-(2-aminoethoxy)], 4-Phenylbenzylalanine, Phe(4-$CONH_2$), Phe(3,4-Dimethoxy), Phe(4-$CF_3$), Phe(2,3-$Cl_2$), and Phe(2,3-$F_2$). Examples of Tyr analogs include, but are not limited to: hTyr, N-Me-Tyr, Tyr (3-tBu), Tyr (4-$N_3$) and $\beta$hTyr.

The invention relates generally to Peptides of the Invention for treating or prevention various metabolic and liver diseases and disorders. In certain embodiments, this invention demonstrates a new paradigm for treatment of obesity, metabolic disorders, and liver disorders, and other diseases and disorders by administration of a Peptide of the Invention. The administration of the Peptides of the Invention is expected to maximize drug levels in diseased tissues while limiting drug concentrations in circulation, thereby providing efficacious, safe, and durable delivery for life-long treatment of obesity and metabolic and liver diseases and disorders.

In certain embodiments, the Peptides of the Invention encompass various peptides, or peptide hetero- or homo-monomer subunits, that optionally form cyclized structures through disulfide or other bonds. In certain embodiments, the disulfide or other bonds are intramolecular bonds. The cyclized structure of the peptides have been shown to increase potency and selectivity of the Peptides of the Invention. In certain embodiments, the Peptides of the Invention may include one or more intermolecular bonds linking the two peptide subunits within the peptide.

In certain embodiments, the Peptides of the Invention reduces the presence of a disease or disorder by at least 20%, at least 30%, at least 40%, at least 50%, at least 60%, at least 70%, at least 80%, or at least 90% as compared to a negative control peptide.

In some embodiments, the half-life is measured in vitro using any suitable method known in the art, e.g., in some embodiments, the stability of a Peptides of the Invention is determined by incubating the peptide with pre-warmed human serum or plasma at 37° C. (one of ordinary skill in the art will recognize that serum or plasma from other species (e.g., rat, mouse, etc.) may be used). Samples are taken at various time points, typically up to 24 hours, and the stability of the sample is analyzed by separating the peptide from the serum or plasma proteins and then analyzing for the presence of the peptide of interest using LC-MS.

In some embodiments, a Peptide of the Invention exhibits improved solubility or reduced aggregation characteristics as compared to a control peptide. Solubility may be determined via any suitable method known in the art. In some embodiments, suitable methods known in the art for determining solubility include incubating peptides in various buffers (Acetate pH 4.0, Acetate pH 5.0, Phosphate/Citrate pH 5.0, Phosphate/Citrate pH 6.0, Phosphate pH 6.0, Phosphate pH 7.0, Phosphate pH 7.5, Strong PBS pH 7.5, Tris pH 7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide is more soluble in a given liquid than is a control peptide. In some embodiments, reduced aggregation means the peptide has less aggregation in a given liquid under a given set of conditions than a control peptide.

In some embodiments, the Peptides of the Invention have less degradation, e.g., over a period of time (i.e., more degradation stability), e.g., greater than or about 10% less, greater than or about 20% less, greater than or about 30% less, greater than or about 40 less, or greater than or about 50% less degradation than a control peptide. In some embodiments, degradation stability is determined via any suitable method known in the art. In some embodiments, the degradation is enzymatic degradation. For example, in certain embodiments, the Peptides of the Invention have reduced susceptibility to degradation by trypsin, chymotrypsin or elastase. In some embodiments, suitable methods known in the art for determining degradation stability include the method described in Hawe et al., J Pharm Sci, VOL. 101, No. 3, 2012, p 895-913, incorporated herein in its entirety. Such methods are in some embodiments used to select potent peptide sequences with enhanced shelf lives.

The various Peptides of the Invention may be constructed solely of natural amino acids. Alternatively, the Peptides of the Invention may include non-natural amino acids including, but not limited to, modified amino acids. In certain embodiments, modified amino acids include natural amino acids that have been chemically modified to include a group, groups, or chemical moiety not naturally present on the amino acid. The Peptides of the Invention may additionally include one or more D-amino acids. Still further, the Peptides of the Invention may include amino acid analogs.

In certain embodiments, Peptides of the Invention include one or more modified or unnatural amino acids. In some embodiments of the present invention, Peptides of the Invention includes one or more non-natural amino acids shown in Table 1. In certain embodiments, the Peptides of the Invention include any of those described herein, including, but not limited to, any of those comprising an amino acid sequence or peptide structure shown herein.

The invention also includes any of the Peptides of the Invention described herein in either a free or a salt form. Thus, embodiments of any of the Peptides of the Invention described herein (and related methods of use thereof) include a pharmaceutically acceptable salt of the Peptides of the Invention.

The invention also includes variants of any of the Peptides of the Invention described herein, including but not limited to any of those comprising a sequence shown in any one of the tables herein, wherein one or more L-amino acid residue is substituted with the D isomeric form of the amino acid residue, e.g., an L-Ala is substituted with a D-Ala.

Peptides of the Invention described herein include isotopically-labeled peptides. In particular embodiments, the present disclosure provides Peptides of the Invention identical to any of those having or recited in the various formulas and structures presented herein, but for the fact that one or more atoms are replaced by an atom having an atomic mass or mass number different from the atomic mass or mass number usually found in nature. Examples of isotopes that can be incorporated into the Peptides of the Invention include isotopes of hydrogen, carbon, nitrogen, oxygen, fluorine and chlorine, such as $^{2}H$, $^{3}H$, $^{13}C$, $^{14}C$, $^{15}N$, $^{180}$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Furthermore, substitution with isotopes such as deuterium, i.e., $^{2}H$, can afford certain therapeutic advantages resulting from greater metabolic stability, for example increased in vivo half-life or reduced dosage requirements.

The invention also includes any of the peptide components described herein linked to a linker moiety, including any of the specific linker moieties described herein. In particular embodiments, a linker is attached to an N-terminal or C-terminal amino acid, while in other embodiments, a linker is attached to an internal amino acid. In particular embodiments, a linker is attached to two internal amino acids, e.g., an internal amino acid in each of two monomer subunits. In some embodiments, a Peptide of the Invention comprises one or more linker moieties.

The invention also includes peptides comprising a peptide having at least 90%, at least 95%, at least 98%, or at least 99% sequence identity to the peptide sequence of a Peptide of the Invention described herein. In particular embodiments, Peptides of the Invention comprise a core peptide sequence and one or more N-terminal and/or C-terminal modification (e.g., Ac and $NH_2$) and/or one or more conjugated linker moiety and/or half-life extension moiety. As used herein, the core peptide sequence is the amino acid sequence of the peptide component absent such modifications and conjugates.

In certain embodiments, a Peptide of the Invention comprises, consists essentially of, or consists of 10 to 90 amino acid residues, 15 to 80 amino acid residues, 20 to 75 amino acid residues, 25 to 70 amino acid residues, 30 to 65 amino acid residues, 35 to 60 amino acid residues, 40 to 55 amino acid residues, 45 to 50 amino acid residues, and, optionally, one or more additional non-amino acid moieties, such as a conjugated chemical moiety, e.g., a PEG or linker moiety.

In particular embodiments, a Peptide of the Invention (or a component thereof), including, but not limited to, those of any embodiments of Formula I-V, is greater than 10, greater than 12, greater than 15, greater than 20, greater than 25, greater than 30 or greater than 35 amino acids, e.g., 35 to 80 amino acids. In certain embodiments, a Peptide of the Invention (or a component monomer subunit thereof) is less than 90, less than 75, less than 60, less than 45, less than 30, less than 25, less than 20, or less than 10 amino acids. In particular embodiments, a component monomer subunit of a Peptide of the Invention comprises or consists of 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues. In particular embodiments, a monomer subunit of a Peptide of the Invention comprises or consists of 10 to 75 amino acid residues and, optionally, one or more additional non-amino acid moieties, such as a conjugated chemical moiety, e.g., a PEG or lapidated amino acid residue.

In particular embodiments of the present invention, the amino acid sequences of the Peptides of the Invention are not present within an antibody, or are not present within a VH or VL region of an antibody.

Peptides of the Invention

The Peptides of the Invention include peptides comprising or consisting of any of the amino acid sequences described herein, peptides having any of the structures described herein.

In one embodiment, the invention encompasses Peptides of the Invention or a pharmaceutically acceptable salt or solvate thereof, wherein the Peptides of the Invention comprises, consists essentially of, or consists of an amino acid sequence of Formula (I):

$X^1$-$X^2$-E-G-T-F-$X^3$-S-D-Y-S-I-$X^4$-$X^5$-D-K-I-$X^6$-Q-$X^7$-$X^8$-F-V-$X^9$-W-L-$X^{10}$-$X^{11}$-$X^{12}$-$X^{13}$ $X^{14}$-$X^{15}$-$X^{16}$-C-N-T-A-T-C-$X^{17}$-$X^{18}$-$X^{19}$-$X^{20}$-L-$X^{21}$-$X^{22}$-$X^{23}$-L-$X^{24}$-$X^{25}$-$X^{26}$-$X^{27}$-$X^{28}$-$X^{29}$ $X^{30}$-$X^{31}$-$X^{32}$-$X^{33}$ $X^{34}$-P-$X^{35}$-T-N-$X^{36}$-G-$X^{37}$-N-T-Y-($NR^1R^2$) (SEQ ID NO: 23)

(I)

wherein $X^1$ is Tyr or (d) Tyr;

$X^2$ is Ala, (d) Ala, or Aib;

$X^3$ is Ile or Thr;

$X^4$ is Ala, Aib or Gln;

$X^5$ is Met, Leu, or Val;

$X^6$ is Ala or His;

$X^7$ is Gln, Lys, or Lys-γ-Glu-γ-Glu-C═O$(CH_2)_nR^3$;

$X^8$ is Ala or Asp;

$X^9$ is Asn or Gln;

$X^{10}$ is Leu, Val, or Ile;

$X^{11}$ is Ala or Val;

$X^{12}$ is Gly or Gln;

$X^{13}$ is Gly, Lys, Arg, Ser, or Lys-γ-Glu-γ-Glu-C═O $(CH_2)_n$ $R^3$;

$X^{14}$ is Pro, Gly, Lys, or Lys-γ-Glu-γ-Glu-C═O$(CH_2)$ $R^3$;

$X^{15}$ is Ser, Gly, Lys, or Lys-γ-Glu-γ-Glu-C═$((CH_2)_nR^3$;

$X^{16}$ is absent or is Gly or Ser;

$X^{17}$ is Ala, Met or Val;

$X^{18}$ is Thr or Leu;

$X^{19}$ is Gln or Gly;

$X^{20}$ is Arg, Lys, Gln, or Lys-γ-Glu-γ-Glu-C—O$(CH_2)_nR^3$;

$X^{21}$ is Ala or Ser;

$X^{22}$ is Asn or Gln;

$X^{23}$ is Phe or Glu;

$X^{24}$ is His or Val;

$X^{25}$ is His or Arg;

$X^{26}$ is Ser or Leu;

$X^{27}$ is Ser or Gln;

$X^{28}$ is Asn or Thr;

$X^{29}$ is absent or is Asn or Gln;

$X^{30}$ is absent or is Phe;

$X^{31}$ is absent or is Gly;

$X^{32}$ is absent or is Pro;

$X^{33}$ is absent or is Ile, Lys, or Lys-γ-Glu-γ-Glu-C═$((CH_2)_n$ $R^3$;

$X^{34}$ is Leu or Tyr;

$X^{35}$ is Pro, Lys Arg, or Lys-Y-Glu-γ-Glu-C═O$(CH_2)_nR^3$;

$X^{36}$ is Val or Thr; and $X^{37}$ is Ser, Lys, or Lys-γ-Glu-γ-Glu-C═$((CH_2)_nR^3$, wherein $R^1$ and $R^2$ are each independently H or $C_{1-5}$ alkyl, $R^3$ is —$CO_2H$, —$CO_2CH_3$, —$CO_2NH_2$, —$CO_2NHCH_3$, —$CO_2N(CH_3)_2$, —$CH_3$, or —$NH_2$, n is an integer from 12-20.

In certain embodiments, $R^3$ is —$CO_2H$.

In certain embodiments, $R^3$ is —$CO_2CH_3$.

In certain embodiments, $R^3$ is —$CO_2NH_2$.

In certain embodiments, $R^3$ is —$CO_2NHCH_3$.

In certain embodiments, $R^3$ is —$CO_2N(CH_3)$ 2.

In certain embodiments, $R^3$ is —$CH_3$.

In certain embodiments, $R^3$ is —$NH_2$.

In certain embodiments, n is 12.

In certain embodiments, n is 13.

In certain embodiments, n is 14.

In certain embodiments, n is 15.

In certain embodiments, n is 16.

In certain embodiments, n is 17.

In certain embodiments, n is 18.

In certain embodiments, n is 19.

In certain embodiments, n is 20.

In certain embodiments, the Peptide of the Invention is a peptide or pharmaceutically acceptable salt thereof of Formula I wherein:

$X^1$ is Tyr;

$X^2$ is Aib;

$X^3$ is Ile;

$X^4$ is Ala;

$X^5$ is Leu;

$X^6$ is His;

$X^7$ is Lys or Lys-γ-Glu-γ-Glu-C═O$(CH_2)_nCH_3$;

$X^8$ is Asp;

$X^9$ is Asn;

$X^{10}$ is Leu;

$X^{11}$ is Ala;

$X^{12}$ is Gln;

$X^{13}$ is Lys or Lys-γ-Glu-γ-Glu-C═O$(CH_2)_nCH_3$;

$X^{14}$ is absent or Pro;

$X^{15}$ is absent or Ser;

$X^{16}$ is absent or Ser or $X^{14}$, $X^{15}$, and $X^{16}$ are together a linking group;

$X^{17}$ is Ala;

$X^{18}$ is Thr;

$X^{19}$ is Gln;

$X^{20}$ is Arg;

$X^{21}$ is Ala;

$X^{22}$ is Asn;

$X^{23}$ is Phe;

$X^{24}$ is Val;
$X^{25}$ is His;
$X^{26}$ is Ser;
$X^{27}$ is Ser;
$X^{28}$ is Asn;
$X^{29}$ is absent or is Asn;
$X^{30}$ is absent or is Phe;
$X^{31}$ is absent or is Gly;
$X^{32}$ is absent or is Pro;
$X^{33}$ is absent or is Ile;
$X^{34}$ is Leu;
$X^{35}$ is Pro;
$X^{36}$ is Val; and
$X^{37}$ is Ser.

In another embodiment, the invention encompasses Peptides of the Invention or a pharmaceutically acceptable salt or solvate thereof, wherein the Peptides of the Invention comprises or consists of an amino acid sequence of Formula (II):

$X^1$-$X^2$-E-G-T-F-$X^3$-S-D-Y-S-I-A-$X^4$-D-K-I-$X^5$-Q-$X^6$-$X^7$-F-V-$X^8$-W-L-L-A-Q-$X^9$-$X^{10}$-$X^{11}$ $X^{12}$-C-N-T-A-T-C-A-T-Q-R-L-A-N-F-L-V-H-S-S-N-N-F-G-P-$X^{13}$-L-P-P-T-N-V-G-$X^{14}$-N-T-Y($NR^1R^2$) (SEQ ID NO: 24)

(II)

wherein:
$X^1$ is Tyr or (d)-Tyr;
$X^2$ is Ala, (d) Ala, or Aib;
$X^3$ is Thr or Ile;
$X^4$ is Met, Leu, or Val;
$X^5$ is His or Ala;
$X^6$ is Gln, Lys, or Lys-γ-Glu-γ-Glu-C=(($CH_2$)$_n$$R^3$;
$X^7$ is Asp or Ala;
$X^8$ is Asn or Gln;
$X^9$ is Gln, Lys, or Lys-Y-Glu-γ-Glu-C=O($CH_2$)$_n$$R^3$;
$X^{10}$ is any naturally occurring amino acid;
$X^{11}$ is any naturally occurring amino acid;
$X^{12}$ is any naturally occurring amino acid;
$X^{13}$ is Ile, Lys, or Lys-γ-Glu-γ-Glu-C=O($CH_2$)$_n$$R^3$; and
$X^{14}$ is Ser, Lys, or Lys-γ-Glu-γ-Glu-C=O($CH_2$)$_n$$R^3$,
wherein
$R^1$ and $R^2$ are each independently H or $C_{1-5}$ alkyl,
$R^3$ is —$CO_2H$, —$CO_2CH_3$, —$CO_2NH_2$, —$CO_2NHCH_3$, —$CO_2N(CH_3)_2$, —$CH_3$, or —$NH_2$,
n is an integer from 12-20.

In certain embodiments, the Peptide of the Invention is a peptide or pharmaceutically acceptable salt thereof of Formula II wherein:
$X^1$ is Tyr;
$X^2$ is Ala;
$X^3$ is Leu;
$X^4$ is Lys-γ-Glu-γ-Glu-C=O($CH_2$)$_n$$R^3$;
$X^5$ is Asn;
$X^6$ is Gln;
$X^7$ is any amino acid;
$X^8$ is any amino acid;
$X^9$ is any amino acid;
$X^{10}$ is Ile; and
$X^{11}$ is Ser (SEQ ID NO: 29).

In certain embodiments, naturally occurring amino acids can be substituted by non-naturally occurring amino acids, and the Peptides of the Invention maintain the biological activity.

In another embodiment, the invention encompasses Peptides of the Invention or a pharmaceutically acceptable salt or solvate thereof, wherein the Peptides of the Invention comprises or consists of an amino acid sequence of Formula (III):

$X^1$-$X^2$-E-G-T-F-$X^3$-S-D-Y-S-I-$X^4$-L-D-K-I-A-Q-$X^5$-A-F-V-Q-W-L-$X^6$-A-G-G-P-S-C-N-T-A-T-C-V-L-G-R-L-S-Q-E-L-H-R-L-Q-T-Y-P-R-T-N-T-G-$X^7$-N-T-Y ($NR^1R^2$) (SEQ ID NO: 25)

(III)

wherein:
$X^1$ is (d) Tyr or Tyr;
$X^2$ is Ala, (d) Ala or Aib;
$X^3$ is Ile or Thr;
$X^4$ is Ala or Aib;
$X^5$ is Gln, Lys, or Lys-γ-Glu-γ-Glu-C=(($CH_2$): $R^3$;
$X^6$ is Leu or Ile; and
$X^7$ is Ser, Lys, or Lys-γ-Glu-γ-Glu-C=O($CH_2$)$_n$$R^3$,
wherein
$R^1$ and $R^2$ are each independently H or $C_{1-5}$ alkyl,
$R^3$ is —$CO_2H$, —$CO_2CH_3$, —$CO_2NH_2$, —$CO_2NHCH_3$, —$CO_2N(CH_3)_2$, —$CH_3$, or —$NH_2$,
n is an integer from 12-20.

In certain embodiments, the Peptide of the Invention is a peptide or pharmaceutically acceptable salt thereof of Formula IV wherein:
$X^1$ is (d) Tyr;
$X^2$ is Aib;
$X^3$ is Thr;
$X^4$ is Aib;
$X^5$ is Gln;
$X^6$ is Ile; and
$X^7$ is Lys-Y-Glu-γ-Glu-C=O($CH_2$)$_n$$R^3$.

In certain embodiments, exemplary peptide components of the Peptides of the Invention include fragments of a component peptide hormone selected from: amylin, ADM, CT, CGRP, intermedin, CCK, leptin, PYY (1-36), PYY (3-36), GLP-1 (1-37), GLP-1 (7-37), GLP-1 (7-36), GLP-2, OXM, a natriuretic peptide, a urocortin family peptide, e.g., Ucn-2 and Ucn-3, a neuromedin family peptide, e.g. neuromedin U25 or splice variant, exendin-3, and exendin-4, wherein the fragment exhibits at least one hormonal activity of the component peptide.

Yet other exemplary peptide components of the Peptides of the Invention include fragments of analogs or derivatives of a component peptide hormone selected from: amylin, ADM, CT, CGRP, intermedin, CCK, leptin, GLP-1 (1-37), GLP-1 (7-37), GLP-1 (7-36), GLP-2, human catestatin, OXM, ANP, BNP, CNP, urodilatin, FGF-19, FGF-21, Ucn-2 and Ucn-3, neuromedin U25 or splice variant, neuromedin S, exendin-3 and exendin-4, wherein the fragment exhibits at least one hormonal activity of the component peptide hormone. Again, the analog may comprise one or more insertions, deletions, or substitutions of the amino acid sequence of the component peptide hormone, and the derivative may comprise one or more chemical modifications of an amino acid residue of an analog or component peptide hormone, as described more fully herein and known in the art.

Certain exemplary fragments that exhibit at least one hormonal activity include the following.

Amylin: amylin (2-37), amylin (1-35), amylin (1-20), amylin (1-18), amylin (1-17), amylin (1-16), amylin (1-15), amylin (1-7)
GLP-1: GLP-1 (7-37), GLP-1 (7-36), GLP-1 (7-35)
GIP: GIP (1-14), GIP (1-28), GIP (1-30) or longer, GIP (1-39) or longer
Exendin: exendin-4 (1-27), exendin-4 (1-28), exendin-4 (1-29), exendin-4 (1-30) or longer.

The Peptides of the Invention may be amidated, but within the context of the present invention, may optionally be in the acid form unless otherwise specified. Further, the above exemplary peptides may be combined with any of the analogs or derivatives discussed herein or known in the art. For example, exemplary analog fragments may include 5Ala, 14Leu, 25Phe-exendin-4 (1-28), 14Leu, 25Phe-exendin-4 (1-27), 5Ala, 14Leu, 25Phe-exendin-4 (1-28), 14Leu, 25Phe-exendin-4 (1-27), or any other combinations of the disclosed fragments, analogs, and derivatives.

Yet other exemplary peptide components include structural motifs of component peptide hormones (including analogs and derivatives thereof) that impart a desired chemical stability, conformational stability, metabolic stability, bioavailability, organ/tissue targeting, receptor interaction, protease inhibition, plasma protein binding, and/or other pharmacokinetic characteristic to the peptide. Exemplary peptide components of the Peptides of the Invention include the following.

Amylin Family: amylin (32-37), amylin (33-37), amylin (34-37), amylin (35-37), amylin (36-37), amylin (37), ADM (47-52), ADM (48-52), ADM (49-52), ADM (50-52), ADM (51-52), ADM (52), CT (27-32), CT (27-32), CT (28-32), CT (29-32), CT (30-32), CT (31-32), CT (32), CGRP (32-37), CGRP (33-37), CGRP (34-37), CGRP (35-37), CGRP (36-37), CGRP (37), intermedin (42-47), intermedin (43-47), intermedin (44-47), intermedin (45-47), intermedin (46-47), intermedin (47).

GLP-1 and 2: GLP-1 (29-37); GLP-1 (30-37); GLP-2 (24-31), GLP-2 (25-31).

GIP: GIP (31-42), GIP (32-42), GIP (33-42), GIP (34-42), GIP (35-42), GIP (36-42), GIP (37-42), GIP (38-42), GIP (39-42), GIP (40-42), GIP (41-42), GIP (42).

Exendin-4: exendin-4 (31-39), exendin-4 (32-39), exendin-4 (33-39), exendin-4 (34-39), exendin-4 (35-39), exendin-4 (36-39), exendin-4 (37-39), exendin-4 (38-39), exendin-4 (39)

In certain embodiments, combinations of the GIP analogs and derivatives taken together with the peptide components described herein are contemplated. For example, the last six amino acid residues of amylin family peptide hormone analogs and derivatives known in the art and/or described above are also contemplated as exemplary peptide components. For example, as further discussed herein, the peptidic enhancer Ex-4 short tail, which is an exemplary Trp-Cage sequence, or analog thereof, is added to the C-terminus of any GIP analog, and in further embodiments the peptidic enhancer is attached using a linker.

In one aspect, the Peptides of the Invention include a GIP portion exhibiting at least 50%, at least 60%, at least 65%, at least 70%, at least 75%, at least 80%, at least 85%, at least 90%, at least 95% or at least 98% sequence identity to a native GIP (1-30), native GIP (1-26), native GIP (1-14), native GIP (1-39), native GIP (19-30), native GIP (19-26), native GIP (19-39), native GIP (19-42) or native GIP (1-42) over the entire length of that GIP portion.

Accordingly, in certain embodiments the Peptides of the Invention can comprise a trp-cage motif. In certain embodiments, the Peptides of the Invention include an N-terminal GIP or novel GIP analog fragment in combination with a C-terminal polypeptide or fragment thereof having a body weight lowering or glucose lowering activity (e.g., antidiabetics, exendin) or the ability to inhibit or reduce gastric emptying. In certain embodiments, the Peptides of the Invention include an N-terminal GIP fragment or novel GIP analog fragment in combination with a C-terminal exendin, GLP1, amylin, CCK, gastrin, secretin, GRP, neuromedins, urocortin, calcitonin, or salmon calcitonin, or fragment thereof. In other embodiments, the Peptides of the Invention include a C-terminal GIP or novel GIP analog fragment in combination with an N-terminal polypeptide or fragment thereof having a body weight reduction or glucose lowering activity (e.g., antidiabetics, exendin) or the ability to inhibit or reduce gastric emptying. In certain embodiments, the Peptides of the Invention include a C-terminal GIP, a novel GIP analog (in which case a Trp-cage forming sequence is present), or fragment thereof, in combination with a N-terminal exendin, GLP1, amylin, CCK, gastrin, secretin, GRP, neuromedins, urocortin, calcitonin, or salmon calcitonin, or fragment thereof.

In other embodiments, a peptide component of a Peptide of the Invention is combined with a gastrin/CCK receptor ligand; an amylin receptor ligand; a calcitonin receptor ligand; an CGRP receptor ligand, an EGF receptor ligand; a Glucagon-like peptide 1 receptor ligand; a Glucagon-like peptide 2 receptor ligand; a gastric inhibitory polypeptide (GIP) receptor ligand; a keratinocyte growth factor (KGF) receptor 1 ligand; a dipeptidyl peptidase IV inhibitor; a REG protein receptor ligand; a Growth Hormone receptor ligand; a Prolactin (PRL) receptor ligand; an Insulin-like Growth Factor (IGF) receptor ligand; PTH-related protein (PTHrP) receptor ligand; hepatocyte growth factor (HGF) receptor ligand; a bone morphogenetic protein (BMP) receptor ligand, a transforming growth factor (TGF receptor ligand; a laminin receptor ligand; a vasoactive intestinal peptide (VIP) receptor ligand; a fibroblast growth factor (FGF) receptor ligand; a nerve growth factor (NGF) receptor ligand; an islet neogenesis associated protein (INGAP) receptor ligand; an Activin-A receptor ligand; a vascular endothelial growth factor (VEGF) receptor ligand; an erythropoietin (EPO) receptor ligand; a pituitary adenylate cyclase activating polypeptide (PACAP) receptor ligand; a granulocyte colony stimulating factor (G-CSF) receptor ligand; a granulocyte-macrophage colony stimulating factor (GM-CSF); a platelet-derived growth factor (PDGF) receptor ligand, and a secretin receptor ligand.

The Peptides of the Invention will preferably retain, at least in part, a biological activity of native human GIP, e.g., the Peptides of the Invention will generally be GIP agonists or antagonists. In one embodiment, the Peptides of the Invention will exhibit biological activity in the treatment and prevention of metabolic conditions and disorders. Further, the novel GIP analog of the Peptides of the Invention may include internal linker compounds, may include chemical modifications at internal amino acid residues, or may be chemically modified at the N-terminal or C-terminal residue. In yet another embodiment, the Peptides of the Invention include only natural L amino acid residues and/or modified natural L amino acid residues. Alternatively, in another embodiment, the Peptides of the Invention do not include unnatural amino acid residues.

In exemplary embodiments, the GIP portion of the Peptides of the Invention comprises a GIP N-terminal region modified or substituted to provide DPP-IV resistance superior to that of native GIP.

In exemplary embodiments, the Peptides of the Invention include a GIP or a novel GIP analog combined with an amylin family peptide including amylin, adrenomedullin ("ADM"), calcitonin ("CT"), calcitonin gene related peptide ("CGRP"), intermedin (also known as "AFP-6") and related peptides. Native amylin family peptide hormones are known in art, as are functional peptide analogs and derivatives. Certain exemplary native peptides, peptide analogs and derivatives are described herein, however it should be recognized that any known amylin family peptides that exhibit hormonal activity known in the art may be used in conjunction with the present invention. Any amylin analog or derivative known in the art may be used in conjunction with the present invention.

The amylin family of peptide hormones is implicated in metabolic diseases and disorders including amylin, calcitonin, calcitonin gene related peptide, adrenomedullin, and intermedin (also known as "AFP-6"). In certain embodiments, the Peptides of the Invention include as a component peptide one or more of an amylin family peptide. Amylin is a 37-amino acid peptide hormone. It was isolated, purified and chemically characterized as the major component of amyloid deposits in the islets of pancreases of human Type 2 diabetics (Cooper et al., Proc. Natl. Acad. Sci., USA, 84:8628-8632 (1987)). The amylin molecule has two post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the N-terminal position, a typical sequence for amidation by protein amidating enzyme, PAM (Cooper et al., Biochem. Biophys. Acta, 1014:247-258 (1989)). By "adrenomedullin" or "ADM" is meant the human peptide hormone and species variants thereof. More particularly, ADM is generated from a 185 amino acid preprohormone through consecutive enzymatic cleavage and amidation. This process culminates in the liberation of a 52 amino acid bioactive peptide. By "calcitonin" or "CT" is meant the human peptide hormone and species variants thereof, including salmon calcitonin ("sCT"). More particularly, CT is a 32 amino acid peptide cleaved from a larger prohormone. It contains a single disulfide bond, which causes the amino terminus to assume the shape of a ring. Alternative splicing of the calcitonin pre-mRNA can yield a mRNA encoding calcitonin gene-related peptide; that peptide appears to function in the nervous and vascular systems. The calcitonin receptor has been cloned and shown to be a member of the seven-transmembrane, G protein-coupled receptor family. By "calcitonin gene related peptide" or "CGRP" is meant the human peptide hormone and species variants thereof, in any physiological form. By "intermedin" or "AFP-6" is meant the human peptide hormone and species variants thereof, in any physiological form.

In certain embodiments, the Peptides of the Invention include as a component peptide an amylin peptide. Amylin is believed to regulate gastric emptying, and suppress glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intrahypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue.

In certain embodiments, the Peptides of the Invention include as a component peptide calcitonin. The hormone calcitonin (CT) was named for its secretion in response to induced hypercalcemia and its rapid hypocalcemic effect. It is produced in and secreted from neuroendocrine cells in the thyroid that have since been termed C cells. The best-studied action of CT (1-32) is its effect on the osteoclast. In vitro effects of CT include the rapid loss of ruffled borders and decreased release of lysosomal enzymes. Ultimately, the inhibition of osteoclast functions by CT results in a decrease in bone resorption. However, neither a chronic reduction of serum CT in the case of thyroidectomy nor the increased serum CT found in medullary thyroid cancer appears to be associated with changes in serum calcium or bone mass. It is thus most likely that a major function of CT (1-32) is to combat acute hypercalcemia in emergency situations and/or protect the skeleton during periods of "calcium stress" such as growth, pregnancy, and lactation. (Reviewed in Becker, JCEM, 89 (4): 1512-1525 (2004) and Sexton, Current Medicinal Chemistry 6:1067-1093 (1999)). Consistent with this is recent data from the calcitonin gene knockout mouse, which removes both the calcitonin and the CGRP-I peptides, that revealed that the mouse had normal levels of basal calcium-related values, but an increased calcemic response (Kurihara H, et al., Hypertens Res. 2003 February; 26 Suppl: S105-8).

CT has an effect on plasma calcium levels and inhibits osteoclast function and is widely used for the treatment of osteoporosis. Therapeutically, salmon CT (sCT) appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

In human studies, salmon calcitonin inhibits gastric emptying and gastrin release following a meal while evoking a dose-dependent relaxation of the gallbladder both in the postprandial and fasting state In mice and monkeys, salmon calcitonin acts anorectically and causes weight loss after a single administration. In chronic studies, oral preparations of salmon calcitonin also reduce food intake and body weight in rat models of obesity and diabetes. Therefore, having a calcitonin component in a therapeutic may be beneficial for weight loss.

In certain embodiments, the Peptides of the Invention include as a component peptide a calcitonin gene related peptide. Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptide discovered to date. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuro-modulation, regulation of calcium metabolism, osteogenic stimulation, insulin secretion, an increase in body temperature and a decrease in food intake. (Wimalawansa, Amylin, calcitonin gene-related peptide, calcitonin and ADM: a peptide superfamily. Crit. Rev Neurobiol. 1997; 11 (2-3): 167-239). An important role of CGRP is to control blood flow to various organs by its potent vasodilatory actions, as evidenced by a decrease of mean arterial pressure following intravenous administration of a-CGRP. The vasodilatory actions are also supported by recent analysis of homozygous knockout CGRP mice, which demonstrated elevated peripheral vascular resistance and high blood pressure caused by increased peripheral sympathetic activity (Kurihara H, et al., Targeted disruption of ADM and aCGRP genes reveals their distinct biological roles. Hypertens Res. 2003 February; 26 Suppl: S105-8). Thus, CGRP appears to elicit vasodilatory effects, hypotensive effects and an increase in heart rate among other actions.

Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension. Preeclamptic toxemia of pregnancy and preterm labor are also potentially treatable. (Wimalawansa, 1997). Recent therapeutic uses include the use of CGRP antagonists for the treatment of migraine headaches.

In certain embodiments, the Peptides of the Invention include as a component peptide adrenomedullin. Adrenomedullin (ADM) is almost ubiquitously expressed with many more tissues containing the peptide than not. A published review of ADM, (Hinson, J. P. et al., Endocrine Reviews (2000) 21 (2): 138-167) details its effects on the cardiovascular system, cellular growth, the central nervous system and the endocrine system, with a range of biological actions including vasodilation, cell growth, regulation of hormone secretion, and natriuresis. Studies in rat, cat, sheep, and man confirm that intravenous infusion of ADM results in potent and sustained hypotension, and is comparable to that of CGRP. However, the hypotensive effect of ADM on mean arterial pressure in the anesthetized rat is not inhibited by the CGRP antagonist CGRP8-37 suggesting that this effect is not mediated via CGRP receptors. Acute or chronic administration of human ADM in rats, anesthetized, conscious or hypertensive, results in a significant decrease in total peripheral resistance accompanied by a fall in blood pressure, with a concomitant rise in heart rate, cardiac output and stroke volume.

ADM has also been proposed as an important factor in embryogenesis and differentiation and as an apoptosis survival factor for rat endothelial cells. This is supported by recent mouse ADM knockout studies, in which mice homozygous for loss of the ADM gene demonstrated defective vascular formation during embryogenesis and thus died mid-gestation. It was reported that ADM+/−heterozygous mice had high blood pressure along with susceptibility to tissue injury (Kurihara H, et al., Hypertens Res. 2003 February; 26 Suppl: S105-8).

ADM affects such endocrine organs as the pituitary, the adrenal gland, reproductive organs and the pancreas. The peptide appears to have a role in inhibiting ACTH release from the pituitary. In the adrenal gland, it appears to affect the secretory activity of the adrenal cortex in both rat and human and it increases adrenal blood flow, acting as a vasodilator in the adrenal vascular bed in intact rats. ADM has been shown to be present throughout the female reproductive tract and plasma levels are elevated in normal pregnancy. Studies in a rat model of preeclampsia show that ADM can reverse hypertension and decrease pup mortality when given to rats during late gestation. Because it did not have a similar effect in animals in early gestation or non-pregnant rats in the preeclampsia model, this suggests that ADM may play an important regulatory role in the utero-placental cardiovascular system. In the pancreas, ADM most likely plays an inhibitory role since it attenuated and delayed insulin response to an oral glucose challenge, resulting in initial elevated glucose levels. ADM can also affect renal function. A bolus administered peripherally can significantly lower mean arterial pressure and raise renal blood flow, glomerular filtration rate and urine flow. In some cases, there is also an increase in Na+ excretion.

ADM also has other peripheral effects on bone and on the lung. For bone, studies have supported a role beyond the cardiovascular system and fluid homeostasis and have demonstrated that ADM acts on fetal and adult rodent osteoblasts to increase cell growth comparable to those of known osteoblast growth factors such as transforming growth factor —alpha. This is important clinically as one of the major challenges in osteoporosis research is to develop a therapy that increases bone mass via osteoblastic stimulation. In the lung, ADM not only causes pulmonary vasodilation, but also inhibits bronchoconstriction induced by histamine or acetylcholine. Recent studies using aerosolized ADM to treat pulmonary hypertension in a rat model indicate that inhalation treatment of this condition is effective, as evidenced by the fact that mean pulmonary arterial pressure and total pulmonary resistance were markedly lower in rats treated with ADM than in those given saline. This result was achieved without an alteration in systemic arterial pressure or heart rate (Nagaya N et al., Am J Physiol Heart Circ Physiol. 2003; 285: H2125-31).

In healthy volunteers, i.v. infusion of ADM has been shown to reduce arterial pressure and to stimulate heart rate, cardiac output, plasma levels of CAMP, prolactin, norepinephrine and rennin. In these patients, there was little or no increase in urine volume or sodium excretion observed. In patients with heart failure or chronic renal failure, i.v. ADM had similar effects to those seen in normal subjects, and also induced diuresis and natriuresis, depending on the dose administered (Nicholls, M G et al. Peptides. 2001; 22:1745-1752) Experimental ADM treatment has also been shown to be beneficial in arterial and pulmonary hypertension, septic shock and ischemia/reperfusion injury (Beltowski J., Pol J. Pharmacol. 2004; 56:5-27). Other indications for ADM treatment include peripheral vascular disease, subarachnoid hemorrhage, hypertension, preeclamptic toxemia of pregnancy and preterm labor, and osteoporosis.

Expression of AFP-6 (i.e., intermedin) is primarily in the pituitary and gastrointestinal tract. A specific receptor for AFP-6 has not been reported; however, binding studies indicate that AFP-6 binds to all the known receptors of the Amylin Family. AFP-6 has been shown to increase cAMP production in SK-N-MC and L6 cells expressing endogenous CGRP receptors and competes with labeled CGRP for binding to its receptors in these cells. In published in vivo studies, AFP-6 administration led to blood pressure reduction in both normal and spontaneously hypertensive rats, most likely via interactions with the CRLR/RAMP receptors. In vivo administration in mice led to a suppression of gastric emptying and food intake. (Roh et al. J Biol. Chem. 2004 Feb. 20; 279 (8): 7264-74.)

It has been reported that the biological actions of amylin family peptide hormones are generally mediated via binding to two closely related type II G protein-coupled receptors (GPCRs), the calcitonin receptor (CTR) and the calcitonin receptor like receptor (CRLR). Cloning and functional studies have shown that CGRP, ADM, and amylin interact with different combinations of CTR or the CRLR and the receptor activity modifying protein (RAMP). Many cells express multiple RAMPs. It is believed that co-expression of RAMPs and either the CTR or CRLR is required to generate functional receptors for calcitonin, CGRP, ADM, and amylin. The RAMP family comprises three members (RAMP1,-2, and -3), which share less than 30% sequence identity, but have a common topological organization. Co-expression of CRLR and RAMP1 leads to the formation of a receptor for CGRP. Co-expression of CRLR and RAMP2 leads to the formation of a receptor for ADM. Co-expression of CRLR and RAMP3 leads to the formation of a receptor for ADM and CGRP. Co-expression of hCTR2 and RAMP1 leads to the formation of a receptor for amylin and CGRP. Co-expression of hCTR2 and RAMP3 leads to the formation of a receptor for amylin.

In certain embodiments, a Peptide of the Invention comprising an amylin family hormone module can provide the functions and uses associated with the amylin family module, e.g. amylin, amylin/sCT/amylin, ADM, CGRP, as discussed, in addition to a GIP function.

In one embodiment, the amylin analogs and derivatives have at least one hormonal activity of native amylin. In certain embodiments, the amylin analogs are agonists of a receptor which native amylin is capable of specifically binding. Exemplary amylin analogs and derivatives include those described in US 2003/0026812 A1, which is hereby incorporated by reference.

In certain embodiments, the Peptides of the Invention include as a component peptide CCK. CCKs, including hCCK (cholecystokinin) and species variants, and various analogs thereof are known in the art. Generally, CCK has a 33-amino acid sequence first identified in humans, and includes a 8-amino acid in vivo C-terminal fragment ("CCK-8") that has been reportedly demonstrated in pig, rat, chicken, chinchilla, dog and humans. Other species variants include a 39-amino acid sequence found in pig, dog and guinea pig, and a 58-amino acid found in cat, dog and humans, and a 47-amino acid sequences homologous to both CCK and gastrin. The C-terminal tyrosine-sulfated octapeptide sequence (CCK-8) is relatively conserved across species, and may be the minimum sequence for biological activity in the periphery of rodents. Thus, the term CCK-33 will generally refer to human CCK (1-33), while CCK-8 (CCK (26-33)) will refer to the C-terminal octapeptide generically in both the sulfated and unsulfated unless otherwise specified. Further, pentagastrin or CCK-5 will refer to the C-terminal peptide CCK (29-33), and the CCK-4 will refer to the C-terminal tetrapeptide CCK (30-33).

CCK was identified from preparations of intestinal extracts by its ability to stimulate gallbladder contraction. Other biological actions of CCK have since been reported, including stimulation of pancreatic secretion, delayed gastric emptying, stimulation of intestinal motility and stimulation of insulin secretion. See Lieverse et al., Ann. N.Y. Acad. Sci. 713:268-272 (1994). The actions of CCK, also reportedly include effects on cardiovascular function, respiratory function, neurotoxicity and seizures, cancer cell proliferation, analgesia, sleep, sexual and reproductive behaviors, memory, anxiety and dopamine-mediated behaviors. Crawley and Corwin, Peptides 15:731-755 (1994). Other reported effects of CCK include stimulation of pancreatic growth, stimulation of gallbladder contraction, inhibition of gastric acid secretion, pancreatic polypeptide release and a contractile component of peristalsis. Additional reported effects of CCK include vasodilation. Walsh, "Gastrointestinal Hormones," In Physiology of the Gastrointestinal Tract (3d ed. 1994; Raven Press, New York).

It has been reported that injections of combinations of glucagon, CCK and bombesin potentiated the inhibition of intake of condensed milk test meals in nondeprived rats over the inhibitions observed with individual compounds. Hinton et al., Brain Res. Bull. 17:615-619 (1986). It has also been reported that glucagon and CCK synergistically inhibit sham feeding in rats. LeSauter and Geary, Am. J. Physiol. 253: $R^{217}$-225 (1987); Smith and Gibbs, Annals N.Y. Acad. Sci. 713:236-241 (1994). It has also been suggested that estradiol and CCK can have a synergistic effect on satiety. Dulawa et al., Peptides 15:913-918 (1994); Smith and Gibbs, supra. It has also been proposed that signals arising from the small intestine in response to nutrients therein may interact synergistically with CCK to reduce food intake. Cox, Behav. Brain Res. 38:35-44 (1990). Additionally, it has been reported that CCK induces satiety in several species. For example, it has been reported that feeding depression was caused by CCK injected intraperitoneally in rats, intraarterially in pigs, intravenously in cats and pigs, into the cerebral ventricles in monkeys, rats, dogs and sheep, and intravenously in obese and non-obese humans. See Lieverse et al., supra. Studies from several laboratories have reportedly confirmed the behavioral specificity of low doses of CCK on inhibition in feeding, by comparing responding for food to responding for nonfood reinforcers in both monkeys and rats and by showing that CCK elicits the sequence of behaviors normally observed after meal ingestion (i.e., the postprandial satiety sequence). Additionally, comparison of behavior after CCK to behavior after food ingestion, alone or in combination with CCK has reportedly revealed behavioral similarities between CCK and food ingestion. It has also been reported that CCK in physiological plasma concentrations inhibits food intake and increases satiety in both lean and obese humans.

CCK is characterized as a 33-amino acid peptide. Species-specific molecular variants of the amino acid sequence of CCK have been identified. The 33-amino acid sequence and a truncated peptide, its 8-amino acid C-terminal sequence (CCK-8) have been reportedly identified in pig, rat, chicken, chinchilla, dog and humans. A 39-amino acid sequence was reportedly found in pig, dog and guinea pig. A 58-amino acid sequence was reported to have been found in cat, dog and humans. Frog and turtle reportedly show 47-amino acid sequences homologous to both CCK and gastrin. Very fresh human intestine has been reported to contain small amounts of an even larger molecule, termed CCK-83. In the rat, a principal intermediate form has been reportedly identified, and is termed CCK-22. Walsh, "Gastrointestinal Hormones," In Physiology of the Gastrointestinal Tract (3d ed. 1994; Raven Press, New York). A non-sulfated CCK-8 and a tetrapeptide (termed CCK-4 (CCK (30-33)) have been reported in rat brain. The C-terminal pentapeptide (termed CCK-4 (CCK (29-33)) conserves the structural homology of CCK, and also homology with the neuropeptide, gastrin. The C-terminal sulfated octapeptide sequence, CCK-8, is reportedly relatively conserved across species. Cloning and sequence analysis of a cDNA encoding preprocholecystokinin from rat thyroid carcinoma, porcine brain, and porcine intestine reportedly revealed 345 nucleotides coding for a precursor to CCK, which is 115 amino acids and contains all of the CCK sequences previously reported to have been isolated. Crawley and Corwin, supra.

CCK is said to be distributed throughout the central nervous system and in endocrine cells and enteric nerves of the upper small intestine. CCK agonists include CCK itself (also referred to as CCK-33), CCK-8 (CCK (26-33)), non-sulfated CCK-8, pentagastrin (CCK-5 or CCK (29-33)), and the tetrapeptide, CCK-4 (CCK (30-33)). At the pancreatic CCK receptor, CCK-8 reportedly displaced binding with a 1000-5000 greater potency than unsulfated CCK-8 or CCK-4, and CCK-8 has been reported to be approximately 1000-fold more potent than unsulfated CCK-8 or CCK-4 in stimulating pancreatic amylase secretion. Crawley and Corwin, supra. In homogenates from the cerebral cortex, CCK receptor binding was said to be displaced by unsulfated CCK-8 and by CCK-4 at concentrations that were equimolar, 10-fold or 100-fold greater than sulfated CCK-8. Id. Receptors for CCK have been reportedly identified in a variety of tissues, and two primary subtypes have been described: type A receptors and type B receptors. Type A receptors have been reported in peripheral tissues including pancreas, gallbladder, pyloric sphincter and afferent vagal fibers, and in discrete areas of the brain. The type A receptor subtype (CCKA) has been reported to be selective for the sulfated octapeptide. The Type B receptor subtype (CCKB) has been identified throughout the brain and in the stomach, and reportedly does not require sulfation or all eight amino acids. See Reidelberger, J. Nutr. 124 (8 Suppl.) 1327S-1333S (1994); Crawley and Corwin, supra.

Various in vivo and in vitro screening methods for CCK analogs are known in the art. Examples include in vivo assays involving the contraction of the dog or guinea pig gallbladder after rapid intravenous injection of the compound to be tested for CCK-like activity, and in vitro assays using strips of rabbit gallbladder. See Walsh, "Gastrointestinal Hormones", In Physiology of the Gastrointestinal Tract (3d ed. 1994; Raven Press, New York).

Component peptide hormones useful as components of the Peptides of the Invention include GLP-1 peptide hormones. Native GLP-1 peptide hormones, including GLP-1 (1-37), GLP-1 (7-37), and GLP-1 (7-36) amide, are known in art, as are functional peptide analogs and derivatives. As used herein, GLP-1 refers to all native forms of GLP-1 peptide hormones. Certain exemplary native peptides, peptide analogs and derivatives are described herein, however it should be recognized that any known GLP-1 peptides that exhibit hormonal activity known in the art may be used in conjunction with the present invention.

Central to many metabolic diseases and disorders is the regulation of insulin levels and blood glucose levels. Insulin secretion is modulated in part by secretagogue hormones, termed as incretins, which are produced by enteroendocrine cells. The incretin hormone, glucagon-like peptide-1 ("GLP-1") is a peptide hormone secreted by intestinal cells that has been shown in multiple studies to produce an enhancing effect on insulin secretion. GLP-1 is processed from proglucagon in the gut and enhances nutrient-induced insulin release (Krcymann B., et al., Lancet, 2:1300-1303 (1987)). Various truncated forms of GLP-1 are known to stimulate insulin secretion (insulinotropic action) and cAMP formation (see, e.g., Mojsov, S., Int. J. Pep. Pro. Res., 40:333-343 (1992)). A relationship between various in vitro laboratory experiments and mammalian, especially human, insulinotropic responses to exogenous administration of GLP-1, GLP-1 (7-36) amide, and GLP-1 (7-37) acid has been established (see, e.g., Nauck, M. A., et al., Diabetologia, 36:741-744 (1993); Gutniak, M., et al., New Eng. J. of Med., 326 (20): 1316-1322 (1992); Nauck, M. A., et al., J. Clin. Invest., 91:301-307 (1993); and Thorens, B., et al., Diabetes, 42:1219-1225 (1993)).

GLP-1 (7-36) amide exerts a pronounced antidiabetogenic effect in insulin-dependent diabetics by stimulating insulin sensitivity and by enhancing glucose-induced insulin release at physiological concentrations (Gutniak M., et al., New Eng. J. Med., 326:1316-1322 (1992)). When administered to non-insulin dependent diabetics, GLP-1 (7-36) amide stimulates insulin release, lowers glucagon secretion, inhibits gastric emptying and enhances glucose utilization (Nauck, 1993; Gutniak, 1992; Nauck, 1993). However, the use of GLP-1 type molecules for prolonged therapy of diabetes has been complicated because the serum half-life of such peptides is quite short.

More particularly, GLP-1 is a 30-amino acid peptide derived from proglucagon, a 160-amino acid prohormone. Actions of different prohormone convertases in the pancreas and intestine result in the production of glucagon and other ill-defined peptides, whereas cleavage of proglucagon results in the production of GLP-1 and GLP-2 as well as two other peptides. The amino acid sequence of GLP-1 is 100% homologous in all mammals, implying a critical physiological role. GLP-1 (7-37) acid is C-terminally truncated and amidated to form GLP-1 (7-36) $NH_2$. The biological effects and metabolic turnover of the free acid GLP-1 (7-37) OH, and the amide, GLP-1 (7-36) $NH_2$, are indistinguishable. By convention, the numbering of the amino acids is based on the processed GLP-1 (1-37) OH from proglucagon. The biologically active GLP-1 is the result of further processing: GLP-1 (7-36) $NH_2$. Thus, the first amino acid of GLP-1 (7-37) OH or GLP-1 (7-36) $NH_2$ is 7His.

In the gastrointestinal tract, GLP-1 is produced by L-cells of intestinal, colonic and rectal mucosa, in response to stimulation by intraluminal glucose. The plasma half-life of active GLP-1 is $<5$ minutes, and its metabolic clearance rate is around 12-13 minutes (Holst, Gastroenterology 107 (6): 1848-55 (1994)). The major protease involved in the metabolism of GLP-1 is dipeptidyl peptidase (DPP-IV or CD26) which cleaves the N-terminal His-Ala dipeptide, thus producing metabolites, GLP-1 (9-37) OH or GLP-1 (9-36) $NH_2$ which are variously described as inactive, weak agonist or antagonists of GLP-1 receptor. The GLP-1 receptor (GLP-1R) is a G protein coupled receptor of 463 amino acid and is localized in pancreatic beta cells, in the lungs, and to a lesser extent in the brain, adipose tissue and kidneys. The stimulation of GLP-1R by GLP-1 (7-37) OH or GLP-1 (7-36) $NH_2$ results in adenylate cyclase activation, cAMP synthesis, membrane depolarization, rise in intracellular calcium and increase in glucose-induced insulin secretion (Holz et al., J. Biol. Chem. 270 (30): 17749-57 (1995)).

GLP-1 is a potent insulin secretagogue that is secreted from the intestinal mucosa in response to food intake. The profound incretin effect of GLP-1 is underscored by the fact that GLP-1R knockout mice are glucose-intolerant. The incretin response of i.v. infused GLP-1 is preserved in diabetic subjects, though the incretin response to oral glucose in these patients is compromised. GLP-1 administration by infusion or sc injections controls fasting glucose levels in diabetic patients, and maintains the glucose threshold for insulin secretion (Gutniak et al., N. Engl. J. Med. 326:1316-22 (1992); Nauck et al., Diabet. Med. 13: (9 Suppl 5): S39-S43 (1996); Nauck et al., J. Clin. Endocrinol. Metab.

76:912-917 (1993)). GLP-1 has shown tremendous potential as a therapeutic agent capable of augmenting insulin secretion in a physiological manner, while avoiding hypoglycemia associated with sulfonylurea drugs.

Other important effects of GLP-1 on glucose homeostasis are suppression of glucagon secretion and inhibition of gastric motility. GLP-1 inhibitory actions on pancreatic alpha cell secretion of glucagon leads to decreases in hepatic glucose production via reduction in gluconeogenesis and glycogenolysis. This antiglucagon effect of GLP-1 is preserved in diabetic patients.

The so-called ileal brake effect of GLP-1, in which gastric motility and gastric secretion are inhibited, is affected via vagal efferent receptors or by direct action on intestinal smooth muscle. Reduction of gastric acid secretion by GLP-1 contributes to a lag phase in nutrient availability, thus obviating the need for rapid insulin response. In summary, the gastrointestinal effects of GLP-1 contribute significantly to delayed glucose and fatty acid absorption and modulate insulin secretion and glucose homeostasis.

GLP-1 has also been shown to induce beta cell specific genes, such as GLUT-1 transporter, insulin (via the interaction of PDX-1 with insulin gene promoter), and hexokinase-1. Thus GLP-1 could potentially reverse glucose intolerance normally associated with aging, as demonstrated by rodent experiments. In addition, GLP-1 may contribute to beta cell neogenesis and increase beta cell mass, in addition to restoring beta cell function during states of beta cell insufficiency.

Central effects of GLP-1 include increases in satiety coupled with decreases in food intake, effected via the action of hypothalamic GLP-1R. A 48-hour continuous SC infusion of GLP-1 in type II diabetic subjects, decreased hunger and food intake and increased satiety. These anorectic effects were absent in GLP-1R knock out mice. Thus, a GIP hybrid comprising an incretin family hormone module can provide the functions and uses associated with the incretin family module, e.g. exendin-4, GLP1, GLP2, as discussed, in addition to having a GIP function.

Any GLP-1 peptide analog or derivative known in the art may be used in conjunction with the present invention. In one embodiment, the GLP-1 peptide analogs and derivatives have at least one hormonal activity of a native GLP-1 peptide. In certain embodiments, the GLP-1 peptide analogs are agonists of a receptor which a native GLP-1 peptide is capable of specifically binding. Exemplary GLP-1 peptide analogs and derivatives include those described in, e.g., WO 91/11457, which is hereby incorporated by reference.

In certain embodiments, the Peptides of the Invention comprise or is any one of the amino acid sequence listed below:

| Peptide No. | SEQ ID NO. | Peptide Sequence |
|---|---|---|
| 1 | SEQ ID NO: 1 | Y-(d)A-E-G-T-F-I-S-D-Y-S-I-A-L-D-K-I-H-Q-Q-D-F-V-N-W-L-L-A-Q-K-G-S-G-C-N-T-A-T-C-A-T-Q-R-L-A-N-F-L-V-H-S-S-N-N-F-G-P-I-L-P-P-T-N-V-G-S-N-T-Y-$NH_2$ |
| 2 | SEQ ID NO: 2 | Y-(d)A-E-G-T-F-I-S-D-Y-S-I-A-L-D-K-I-H-Q-Q-D-F-V-N-W-L-L-A-Q-K-G-K*-G-C-N-T-A-T-C-A-T-Q-R-L-A-N-F-L-V-H-S-S-N-N-F-G-P-I-L-P-P-T-N-V-G-S-N-T-Y-$NH_2$ |
| 3 | SEQ ID NO: 3 | Y-(d)A-E-G-T-F-I-S-D-Y-S-I-A-L-D-K-I-H-Q-Q-D-F-V-N-W-L-L-A-Q-K-G-S-G-C-N-T-A-T-C-A-T-Q-R-L-A-N-F-L-V-H-S-S-N-N-F-G-P-K*-L-P-P-T-N-V-G-S-N-T-Y-$NH_2$ |
| 4 | SEQ ID NO: 4 | Y-(d)A-E-G-T-F-I-S-D-Y-S-I-A-L-D-K-I-H-Q-Q-D-F-V-N-W-L-L-A-Q-K-G-S-G-C-N-T-A-T-C-A-T-Q-R-L-A-N-F-L-V-H-S-S-N-N-F-G-P-I-L-P-P-T-N-V-G-K*-N-T-Y-$NH_2$ |
| 5 | SEQ ID NO: 5 | Y-(d)A-E-G-T-F-I-S-D-Y-S-I-A-L-D-K-I-H-Q-Q-D-F-V-N-W-L-L-A-G-G-P-S-S-C-N-T-A-T-C-A-T-Q-R-L-A-N-F-L-V-H-S-S-N-N-F-G-P-I-L-P-P-T-N-V-G-S-N-T-Y-$NH_2$ |
| 6 | SEQ ID NO: 6 | Y-(d)A-E-G-T-F-I-S-D-Y-S-I-A-L-D-K-I-H-Q-Q-D-F-V-N-W-L-L-A-Q-K-G-S-G-C-N-T-A-T-C-V-L-G-R-L-S-Q-E-L-H-R-L-Q-T-Y-P-R-T-N-T-G-S-N-T-Y-$NH_2$ |
| 7 | SEQ ID NO: 7 | Y-(d)A-E-G-T-F-I-S-D-Y-S-I-A-L-D-K-I-H-Q-Q-D-F-V-N-W-L-L-A-Q-K-G-K*-G-C-N-T-A-T-C-V-L-G-R-L-S-Q-E-L-H-R-L-Q-T-Y-P-R-T-N-T-G-S-N-T-Y-$NH_2$ |
| 8 | SEQ ID NO: 8 | Y-(d)A-E-G-T-F-I-S-D-Y-S-I-A-L-D-K-I-H-Q-Q-D-F-V-N-W-L-L-A-Q-K-G-S-G-C-N-T-A-T-C-V-L-G-R-L-S-Q-E-L-H-R-L-Q-T-Y-P-R-T-N-T-G-K*-N-T-Y-$NH_2$ |
| 9 | SEQ ID NO: 9 | Y-Aib-E-G-T-F-T-S-D-Y-S-I-Aib-L-D-K-I-A-Q-Q-A-F-V-Q-W-L-L-A-G-G-P-S-C-N-T-A-T-C-A-T-Q-R-L-A-N-F-L-V-H-S-S-N-N-F-G-P-I-L-P-P-T-N-V-G-S-N-T-Y-$NH_2$ |
| 10 | SEQ ID NO: 10 | Y-Aib-E-G-T-F-T-S-D-Y-S-I-Aib-L-D-K-I-A-Q-K*-A-F-V-Q-W-L-L-A-G-G-P-S-C-N-T-A-T-C-A-T-Q-R-L-A-N-F-L-V-H-S-S-N-N-F-G-P-I-L-P-P-T-N-V-G-S-N-T-Y-$NH_2$ |
| 11 | SEQ ID NO: 11 | Y-Aib-E-G-T-F-T-S-D-Y-S-I-Aib-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| 12 | SEQ ID NO: 12 | Y-Aib-E-G-T-F-T-S-D-Y-S-I-Aib-L-D-K-I-A-Q-K*-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| 13 | SEQ ID NO: 13 | Y-(d)A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |

-continued

| Peptide No. | SEQ ID NO. | Peptide Sequence |
|---|---|---|
| 14 | SEQ ID NO: 14 | Y-(d)A-E-G-T-F-T-S-D-Y-S-I-A-L-D-K-I-A-Q-K*-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| 15 | SEQ ID NO: 15 | Y-(d)A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-K*-N-T-Y-$NH_2$ |
| 16 | SEQ ID NO: 16 | (d)Y-A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| 17 | SEQ ID NO: 17 | (d)Y-A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-K*-N-T-Y-$NH_2$ |
| 18 | SEQ ID NO: 18 | (d)Y-A-E-G-T-F-T-S-D-Y-S-I-A-L-D-K-I-A-Q-K*-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| 19 | SEQ ID NO: 19 | (d)Y-A-E-G-T-F-T-S-D-Y-S-I-Q-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-K*-N-T-Y-$NH_2$ |
| 20 | SEQ ID NO: 20 | (d)Y-A-E-G-T-F-T-S-D-Y-S-I-Q-L-D-K-I-A-Q-Q-A-F-V-Q-W-L-L-A-G-K*-G-S-C-N-T-A-T-C-V-L-G-R-L-S-Q-E-L-H-R-L-Q-T-Y-P-R-T-N-T-G-S-N-T-Y-$NH_2$ |
| 21 | SEQ ID NO: 21 | (d)Y-A-E-G-T-F-T-S-D-Y-S-I-Q-L-D-K-I-A-Q-Q-A-F-V-Q-W-L-L-A-G-S-G-C-N-T-A-T-C-V-L-G-R-L-S-Q-E-L-H-R-L-Q-T-Y-P-R-T-N-T-G-K*-N-T-Y-$NH_2$ |
| 22 | SEQ ID NO: 22 | (d)Y-A-E-G-T-F-T-S-D-Y-S-I-Q-L-D-K-I-A-Q-Q-A-F-V-Q-W-L-L-A-G-S-G-C-N-T-A-T-C-A-T-Q-R-L-A-N-F-L-V-H-S-S-N-N-F-G-P-I-L-P-P-T-N-V-G-K*-N-T-Y-$NH_2$ |

AA with a * indicate the presence of a linking group (e.g., Lys-γGlu-γGlu-C(=O)$(CH_2)_nR^3$, wherein $R^3$ and n are defined above.

Any of the Peptides of the Invention may be further defined, for example, as described below. It is understood that each of the further defining features described herein may be applied to any of the Peptides of the Invention where the amino acids at particular position chemically allows the presence of the further defining feature. In particular embodiments, these features may be present in any of the Peptides of the Invention of Formula (I)-(V).

In various embodiments, a nitrogen group of any of the amino acids of the Peptides of the Invention may be substituted optionally with a $C_1$-$C_6$ alkyl, a $C_6$-$C_{12}$ aryl, a C6-$C_{12}$ aryl $C_1$-$C_6$ alkyl, or a C1-$C_{20}$ alkanoyl, and including PEGylated versions alone or as spacers of any of the foregoing, e.g., acetyl. It is understood that the N-substitution may be absent. In certain embodiments, the Peptides of the Invention comprise an N-terminus selected from hydrogen, a $C_1$-$C_6$ alkyl, a C6-$C_{12}$ aryl, a C6-$C_{12}$ aryl $C_1$-$C_6$ alkyl, or a C1-$C_{20}$ alkanoyl, and including PEGylated versions alone or as spacers of any of the foregoing, e.g., acetyl. In particular embodiments of any of the Peptides of the Invention described herein, the N-terminal moiety is hydrogen.

In certain embodiments of any of the Peptides of the Invention having any of the various Formulas set forth herein, the N-substituted moiety is selected from methyl, acetyl, formyl, benzoyl, trifluoroacetyl, isovaleryl, isobutyryl, octanyl, and the conjugated amides of lauric acid, hexadecanoic acid, and γ-Glu-hexadecanoic acid. In certain embodiments, the N-substituted moiety is pGlu. In particular embodiments, N substitution is acetyl, whereby the Peptide of the Invention is acylated at its N (e.g., to cap or protect an N-terminal amino acid residue, e.g., an N-terminal Pen residue).

In certain embodiments of any of the Peptides of the Invention described herein, the N-substituted moiety is an acid. In certain embodiments, the N-substituted moiety is an acid selected from acetic acid, formic acid, benzoic acid, trifluoroacetic acid, isovaleric acid, isobutyric acid, octanoic acid, lauric acid, hexadecanoic acid, 4-biphenylacetic acid, 4-fluorophenylacetic acid, gallic acid, pyroglutamic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, 4-methylbicyclo (2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, an alkylsulfonic acid and an arylsulfonic acid.

In particular embodiments, the N-substituted moiety is an alkylsulfonic acid selected from methanesulfonic acid, ethanesulfonic acid, 1,2-ethane-disulfonic acid, and 2-hydroxyethanesulfonic acid.

In particular embodiments, the N-substituted moiety is an arylsulfonic acid selected from benzenesulfonic acid, 4-chlorobenzenesulfonic acid, 2-naphthalenesulfonic acid, 4-toluenesulfonic acid, and camphorsulfonic acid.

In certain embodiments, the Peptides of the Invention include one or more linker groups covalently linking one peptide component with a second subunit. The subunits are optionally linked via their C-termini.

The Peptides of the Invention generally comprise at least two peptide components wherein at least one of the peptide components, for example a GIP component, exhibits at least one hormonal activity. Within the context of the invention, at least one of the peptide components will be comprised from a GIP peptide, analog, derivative, fragment, or peptidic enhancer. The peptide components that exhibits the at least one hormonal activity may be located at the N-terminal end of the peptide, the C-terminal end of the peptide, or in the event that the peptide comprises more than two peptide components may be located for example in the internal portion of the peptide.

In certain embodiments, it may be preferable to locate the peptide component exhibiting the at least one hormonal activity such that the C-terminal end of the peptide component is amidated. Amidation of the C-terminal end of the peptide components may be accomplished by locating the module at the C-terminal end of the hybrid peptide, or by configuring the peptide in the C-terminal-to-N-terminal direction at the N-terminal end of the peptide. In both configurations, the C-terminal end of the peptide component is available for amidation. Specific component peptides where C-terminal amidation may preferably include amylin family peptide, CCK, PYY, hGLP-1 (7-36) and hGLP-2. Specific component peptides where C-terminal amidation is not necessarily exemplary (stated otherwise, where elongation at the C-terminal end of the module is easily tolerated) include exendin-4, exendin-4 (1-28), GIP, GLP-1 (7-37), frog GLP-1 (7-36), and frog GLP-2. However, if these component peptide are located at the C-terminal end of the peptide, they may still be optionally amidated, and in fact may preferably be optionally amidated.

The Peptides of the Invention component peptides may be covalently linked in any manner known in the art. Stable linkages may be used, or cleavable linkage may be used. In one embodiment, the carboxy of a first peptide may be directly linked to the amino of a second peptide. In another embodiment, linking groups may be used to attached modules. Further, if desired, spacers or turn inducers known in the art may be employed to stabilize the linkage. By way of example, where amidation of the C-terminal end of the N-terminally located peptide component is not desired, the module may be attached to a second module directly, or using any appropriate linking group known in the art, such as, for example, an alkyl; PEG; amino acid, e.g., Lys, Glu, beta-Ala; polyaminoacids, e.g., poly-his, poly-arg, poly-lys, poly-ala, Gly-Ser-Gly, Gly-Gly-Pro-Ser (SEQ ID NO: 26), Ala-Lys-Ala, Gly-Lys-Arg (GKR) etc.; bifunctional linker (see, e.g., Pierce catalog, Rockford, Ill.); aminocaproyl ("Aca"), beta-alanyl, 8-amino-3,6-dioxaoctanoyl, or other cleavable and non-cleavable linker known in the art. Specifically described herein, as if each were explicitly drawn, are embodiments of specific hybrids in which the linker in each exemplified linker-containing hybrid is replaced by a Gly linker, particularly embodiments where the Gly linker is Gly-Gly-Gly. In one embodiment a linker or spacer is 1 to 30 residues long, in another embodiment 2 to 30 residues, and in yet another 3-30 residues long, and any integer length from 2 to 30 inclusive; each integer unit is contemplated, e.g. 2, 3, 4, 5, 6, 7, etc. In one embodiment a Gly linker is used, and in a particular embodiment a three-residue linker Gly-Gly-Gly.

In certain embodiments, peptide components of the invention may be linked by a suitable linking moiety, e.g., a disulphide bridge between two cysteine residues, one in each peptide subunit, or by another suitable linker moiety, including but not limited to those defined herein. In certain embodiments, the subunit may be modified to eliminate either the C- or N-terminal free amine, thereby permitting dimerization at the remaining free amine. Further, in some instances, a terminal end of one or more monomer subunits is acylated with an acylating organic compound selected from the group consisting of: trifluoropentyl, acetyl, octanyl, butyl, pentyl, hexyl, palmityl, trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid, and glutaric acid. In some instances, subunits comprise both a free carboxy terminal and a free amino terminal, whereby a user may selectively modify the subunit to achieve dimerization at a desired terminus. One having skill in the art will appreciate that the subunits of the invention may be selectively modified to achieve a single, specific amine for a desired linking.

It is further understood that the C-terminal residues of the subunits disclosed herein are optionally amides. Further, it is understood that, in certain embodiments, dimerization at the C-terminus is facilitated by using a suitable amino acid with a side chain having amine functionality, as is generally understood in the art. Regarding the N-terminal residues, it is generally understood that coupling may be achieved through the free amine of the terminal residue, or may be achieved by using a suitable amino acid side chain having a free amine, as is generally understood in the art.

The linker moieties connecting subunits may include any structure, length, and/or size that is compatible with the teachings herein. In at least one embodiment, a linker moiety is selected from the non-limiting group consisting of cysteine, lysine, DIG, PEG4, PEG4-biotin, PEG13, PEG25, PEGIK, PEG2K, PEG3.4K, PEG4K, PEG5K, IDA, ADA, Boc-IDA, Glutaric acid, Isophthalic acid, 1,3-phenylenediacetic acid, 1,4-phenylenediacetic acid, 1,2-phenylenediacetic acid, Triazine, Boc-Triazine, IDA-biotin, PEG4-Biotin, AADA, suitable aliphatics, aromatics, heteroaromatics, and polyethylene glycol based linkers having a molecular weight from approximately 400 Da to approximately 40,000 Da. In certain embodiments, PEG2 is $HO_2CCH_2CH_2OCH_2CH_2OCH_2CH_2CO_2H$.

Non-limiting examples of suitable linker moieties are provided in Table 3. Table 3. Illustrative Linker Moieties

| Abbreviation | Description | Structure |
|---|---|---|
| DIG | DiGlycolic acid, | 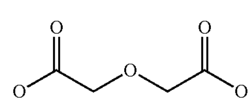 |
| PEG4 | Bifunctional PEG linker with 4 PolyEthylene Glycol units | 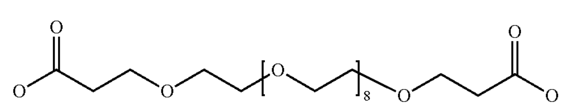 |
| PEG13 | Bifunctional PEG linker with 13 Poly Ethylene Glycol units | 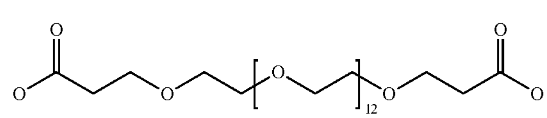 |

-continued

| Abbreviation | Description | Structure |
|---|---|---|
| PEG25 | Bifunctional PEG linker with 25 PolyEthylene Glycol units | 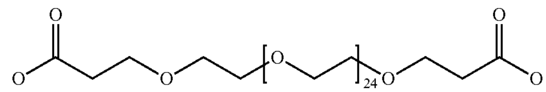 |
| PEG1K | Bifunctional PEG linker with Poly Ethylene Glycol Mol wt of 1000 Da | |
| PEG2K | Bifunctional PEG linker with PolyEthylene Glycol Mol wt of 2000 Da | |
| PEG3.4K | Bifunctional PEG linker with Poly Ethylene Glycol Mol wt of 3400 Da | |
| PEG5K | Bifunctional PEG linker with Poly Ethylene Glycol Mol wt of 5000 Da | |
| PEG20K | Bifunctional PEG linker with Poly Ethylene Glycol Mol wt of 20,000 Da | |
| PEG40K | Bifunctional PEG linker with Poly Ethylene Glycol Mol wt of 40,000 Da | |
| DIG | DIGlycolic acid | 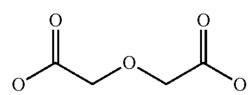 |
| β-Ala-IDA | B-Ala-Iminodiacetic acid | 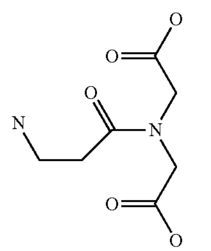 [SMILES: NCCC(=O)N(CC(=O)O)CC(=O)O] |
| Boc-β-Ala-IDA | Boc-β-Ala-Iminodiacetic acid | 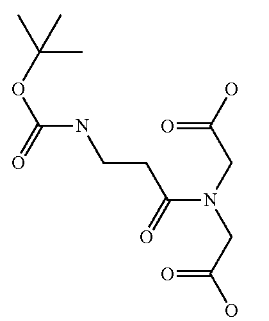 [SMILES: CC(C)(C)OC(=O)NCCC(=O)N(CC(=O)O)CC(=O)O] |
| Ac-β-Ala-IDA | Ac-β-Ala-Iminodiacetic acid | 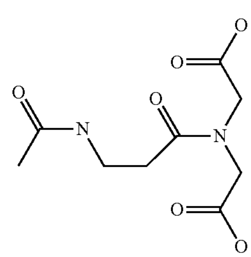 [SMILES: CC(=O)NCCC(=O)N(CC(=O)O)CC(=O)O] |

-continued
| Abbreviation | Description | Structure |
| --- | --- | --- |
| IDA-β-Ala-Palm | Palmityl-β-Ala-Iminodiacetic acid | 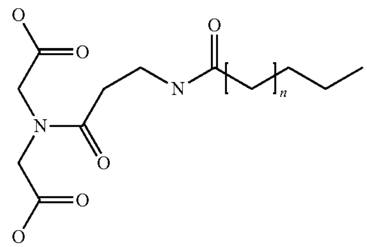 |
| GTA | Glutaric acid | 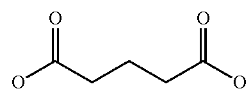 |
| PMA | Pemilic acid | 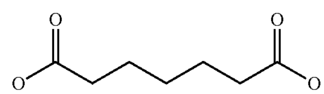 [SMILES: O=C(O)CCCCCC(=O)O] |
| AZA | Azelaic acid | 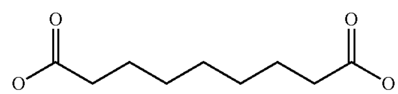 [SMILES: O=C(O)CCCCCCCC(=O)O] |
| DDA | Dodecanedioic acid | 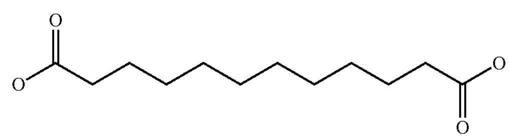 [SMILES: O=C(O)CCCCCCCCCCC(=O)O] |
| IPA | Isopthalic acid | 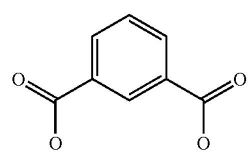 [SMILES: O=C(O)c1cccc(C(=O)O)c1] |
| 1,3-PDA | 1,3- Phenylenediacetic acid | 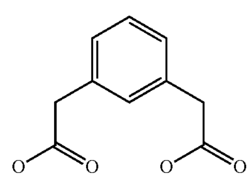 [SMILES: O=C(O)Cc1cccc(CC(=O)O)c1] |
| 1,4-PDA | 1,4- Phenylenediacetic acid | 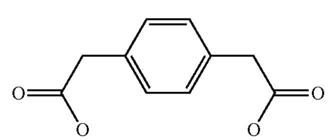 [SMILES: O=C(O)Cc1ccc(CC(=O)O)cc1] |
| 1,2-PDA | 1,2 - Phenylenediacetic acid | 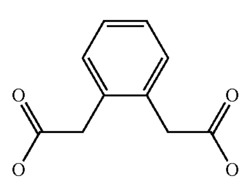 [SMILES: O=C(O)Cc1ccccc1CC(=O)O] |

-continued

| Abbreviation | Description | Structure |
|---|---|---|
| Triazine | Amino propyl Triazine di-acid | 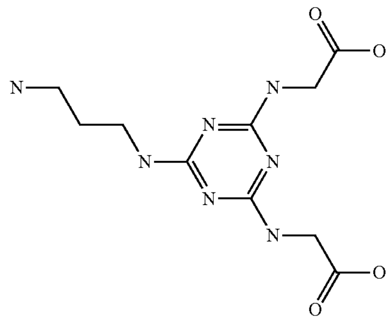 [SMILES: NCCCNc1nc(NCC(=O)O)nc(NCC(=O)O)n1] |
| Boc-Triazine | Boc-Triazine di-acid | 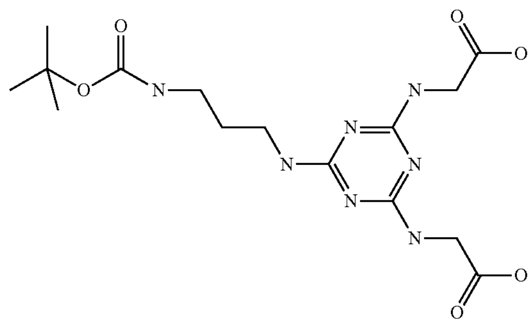 [SMILES: CC(C)(C)OC(=O)NCCCNc1nc(NCC(=O)O)nc(NCC(=O)O)n1] |
| ADA | Amino diacetic acid (which may also be referred to as Iminodiacetic acid) | 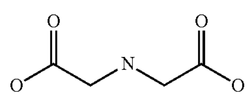 |
| AADA | n-Acetyl amino acetic acid (which may also be referred to as N- acetyl Iminodiacetic acid) | 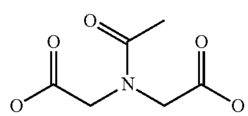 |
| PEG4-Biotin | PEG4-Biotin (Product number 10199, QuantaBioDesign) | 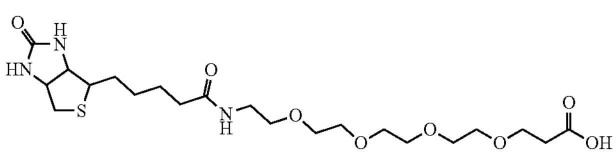 [SMILES: O=C(O)CCOCCOCCOCCOCCNC(=O)CCCCC1SCC2NC(=O)NC21] |
| IDA-Biotin | N-Biotin-β-Ala-Iminodiacetic acid | 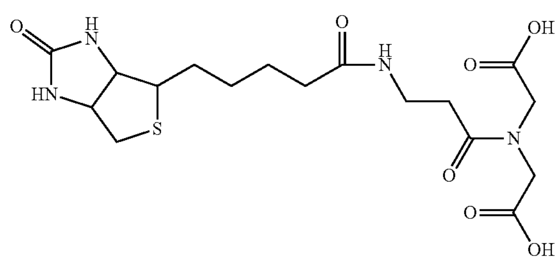 [SMILES: O=C(O)CN(CC(=O)O)C(=O)CCNC(=O)CCCCC1SCC2NC(=O)NC21] |
| Lys | Lysine | 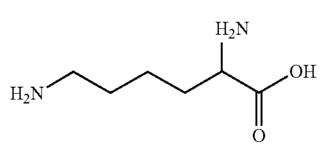 |

In some embodiments, the Peptides of the Invention include a linker moiety. In some embodiments, the Peptide of the Invention subunits are joined by an intermolecular disulfide bond formed between two cysteine residues, one in each subunit. In some embodiments, Peptides of the Invention include both a linker moiety and an intermolecular disulfide bond formed between two cysteine residues. In some embodiments, the intramolecular bond is a thioether, lactam, triazole, selenoether, diselenide or olefin, instead of the disulfide bond.

One having skill in the art will appreciate that the linker (e.g., C- and N-terminal linker) moieties disclosed herein are non-limiting examples of suitable linkers, and that the invention may include any suitable linker moiety. Thus, some embodiments of the invention comprise a homo- or heterodimer peptide comprised of two monomer subunits selected from the peptides shown in any of tables herein or comprising or consisting of a sequence presented in any of tables herein, wherein the C- or N-termini of the respective subunits (or internal amino acid residues) are linked by any suitable linker moiety to provide a Peptide of the Invention. In certain embodiments, a linker binds to the N- or C-terminus of one subunit and an internal amino acid residue of the other subunit making up the Peptides of the Invention. In certain embodiments, a linker binds to an internal amino acid residue of one monomer subunit and an internal amino acid residue of the other monomer subunit making up the Peptides of the Invention. In further embodiments, a linker binds to the N- or C-terminus of both subunits.

In particular embodiments, one or more of the subunits comprise the sequence or structure of any one of Formula (I)-(V), or any of the peptides described herein. In particular embodiments of Peptides of the Invention, the linker moiety is any of the linkers described herein. In certain embodiments, the linker is a lysine linker, a diethylene glycol linker, an iminodiacetic acid (IDA) linker, a β-Ala-iminodiaceticacid (β-Ala-IDA) linker, or a PEG linker.

In various embodiments of any of the Peptides of the Invention, each of the peptide subunits is attached to a linker moiety via its N-terminus, C-terminus, or an internal amino acid residue. In certain embodiments of any of the Peptides of the Invention, the N-terminus of each peptide subunit is connected by a linker moiety. In certain embodiments of any of the Peptides of the Invention, the C-terminus of each peptide subunit is connected by a linker moiety. In certain embodiments of any of the Peptides of the Invention, each peptide subunit is connected by a linker moiety attached to an internal amino acid.

In certain embodiments, Peptides of the Invention comprise one or more conjugated chemical substituents, such as lipophilic substituents and polymeric moieties, which may be referred to herein as half-life extension moieties. Without wishing to be bound by any particular theory, it is believed that the lipophilic substituent binds to albumin in the bloodstream, thereby shielding the Peptides of the Invention from enzymatic degradation, and thus enhancing its half-life. In addition, it is believed that polymeric moieties enhance half-life and reduce clearance in the bloodstream.

In additional embodiments, any of the Peptides of the Invention for example peptides of Formula (I)-(V) further comprise a linker moiety attached to an amino acid residue present in the peptide, e.g., a linker moiety may be bound to a side chain of any amino acid of the peptide, to the N-terminal amino acid of the peptide, or to the C-terminal amino acid of the peptide.

In additional embodiments, any of the Peptides of the Invention e.g. peptides of Formulas (I)-(V), further comprise half-life extension moiety attached to an amino acid residue present in the peptide, e.g., a half-life extension moiety may be bound to a side chain of any amino acid of the peptide, to the N-terminal amino acid of the peptide, or to the C-terminal amino acid of the peptide.

In additional embodiments, any of the Peptides of the Invention e.g. peptides of Formulas (I)-(V), further comprise half-life extension moiety attached to a linker moiety that is attached to an amino acid residue present in the peptide, e.g., a half-life extension moiety may be bound to a linker moiety that is bound to a side chain of any amino acid of the peptide, to the N-terminal amino acid of the peptide, or to the C-terminal amino acid of the peptide.

In particular embodiments, a peptide comprises a half-life extension moiety having the structure shown below, wherein n=0 to 24 or n=14 to 24:

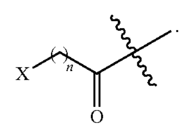

n = 0 to 24
X = $CH_3$, $CO_2H$, $NH_2$, OH

In certain embodiments, a Peptide of the Invention comprises a half-life extension moiety shown in Table 4.

TABLE 4

| Illustrative Half-Life Extension Moieties | |
|---|---|
| # | Half-Life Extension Moieties |
| C1 | 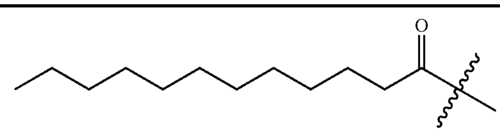 (Lauric acid) |
| C2 | 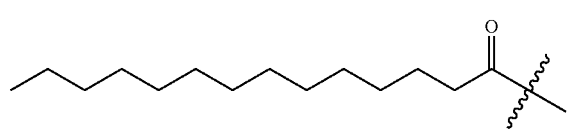 (Mysteric acid) |
| C3 | 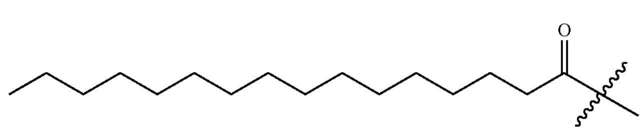 (Palm or palmitic acid) |

TABLE 4-continued
| Illustrative Half-Life Extension Moieties | |
|---|---|
| # | Half-Life Extension Moieties |
| C4 | 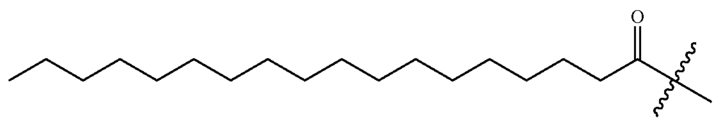<br>(Stearic acid) |
| C5 | 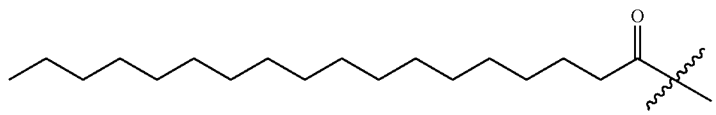<br>C20 |
| C6 | 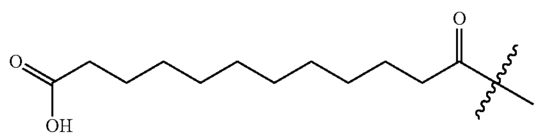<br>diacid |
| C7 | 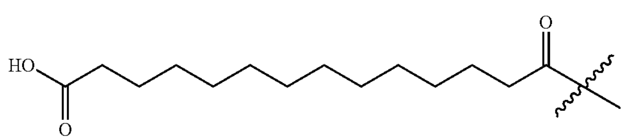<br>diacid |
| C8 | 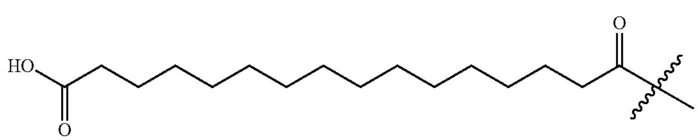<br>diacid |
| C9 | 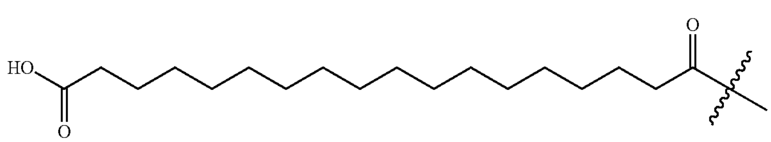<br>diacid |
| C10 | 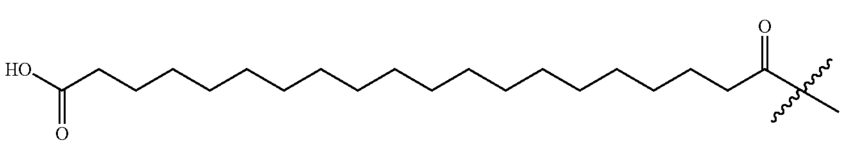<br>diacid |

In certain embodiments, a half-life extension moiety is bound directly to a peptide, while in other embodiments, a half-life extension moiety is bound to the peptide via a linker moiety, e.g., any of those depicted herein.

TABLE 5

Illustrative Linker Moieties

| # | Linker Moiety |
|---|---|
| L1 | 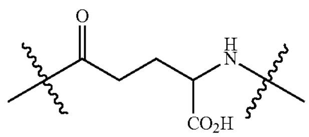<br>IsoGlu |
| L2 | 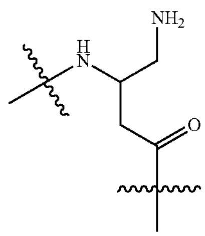 [SMILES: *NC(CN)CC(*)=O]<br>Dapa |
| L3 | 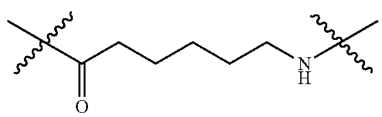 [SMILES: *NCCCCCC(*)=O]<br>Ahx |
| L4 | Lipidic based linkers:<br>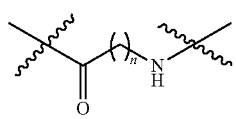<br>n = 1 to 24 |
| L5 | 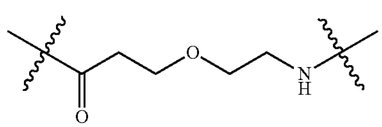 [SMILES: *NCCOCCC(*)=O]<br>PEG1 |
| L6 | 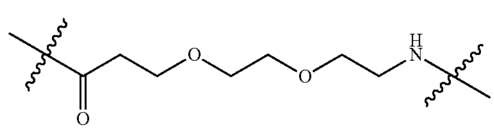 [SMILES: *NCCOCCOCCC(*)=O]<br>PEG2 |
| L7 | 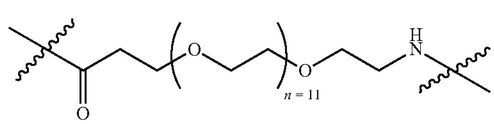<br>PEG11 (40 atoms) also known as PEG12 |
| L8 | 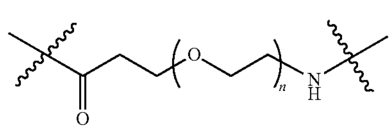 |

TABLE 5-continued
| Illustrative Linker Moieties | |
|---|---|
| # | Linker Moiety |
| | n = 1 to 25<br>PEG based linkers |
| L9 | 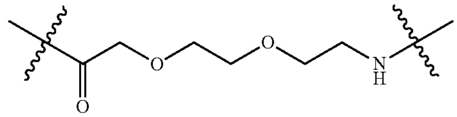 [SMILES: *NCCOCCOCC(*)=O]<br>OEG |
| L10 | 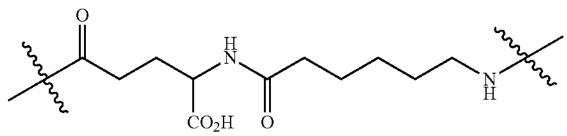 [SMILES: *NCCCCCC(=O)NC(CCC(*)=O)C(=O)O]<br>IsoGlu-Ahx |
| L11 | 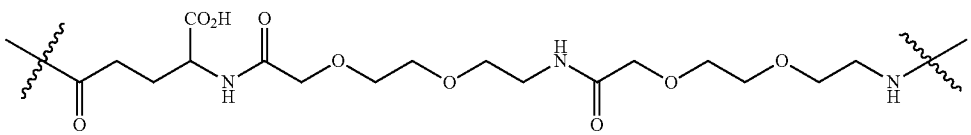 [SMILES: *NCCOCCOCC(=O)NCCOCCOCC(=O)NC(CCC(*)=O)C(=O)O]<br>IsoGlu-OEG-OEG |
| L12 | 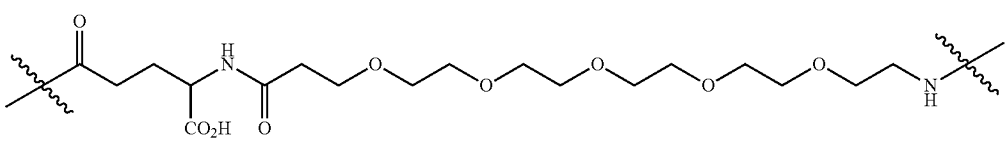 [SMILES: *NCCOCCOCCOCCOCCOCCC(=O)NC(CCC(*)=O)C(=O)O]<br>IsoGlu-PEG5 |
| L13 | 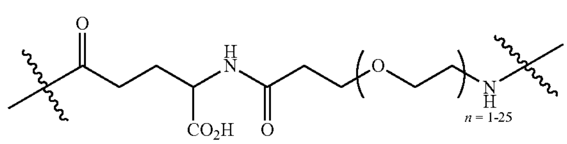<br>IsoGlu-PEGn |
| L14 | 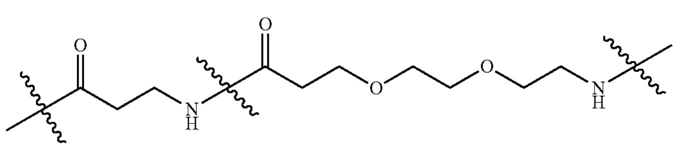<br>βAla-PEG2 |
| L15 | 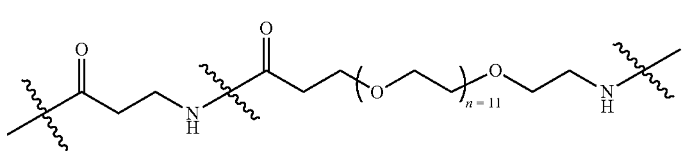<br>βAla-PEG11 (40 atoms) |

In particular embodiments, a Peptide of the Invention comprises any of the linker moieties shown herein and any of the half-life extension moieties shown herein including any of the following combinations shown in Table 6.

TABLE 6

Illustrative Combinations of Linkers and Half-Life Extension Moieties in Peptides of the Invention

| Linker | Half-Life Extension Moiety |
|---|---|
| L1 | C1 |
| L2 | C1 |
| L3 | C1 |
| L4 | C1 |
| L5 | C1 |
| L6 | C1 |
| L7 | C1 |
| L8 | C1 |
| L9 | C1 |
| L10 | C1 |
| L11 | C1 |
| L12 | C1 |
| L13 | C1 |
| L14 | C1 |
| L15 | C1 |
| L1 | C2 |
| L2 | C2 |
| L3 | C2 |
| L4 | C2 |
| L5 | C2 |
| L6 | C2 |
| L7 | C2 |
| L8 | C2 |
| L9 | C2 |
| L10 | C2 |
| L11 | C2 |
| L12 | C2 |
| L13 | C2 |
| L14 | C2 |
| L15 | C2 |
| L1 | C3 |
| L2 | C3 |
| L3 | C3 |
| L4 | C3 |
| L5 | C3 |
| L6 | C3 |
| L7 | C3 |
| L8 | C3 |
| L9 | C3 |
| L10 | C3 |
| L11 | C3 |
| L12 | C3 |
| L13 | C3 |
| L14 | C3 |
| L15 | C3 |
| L1 | C4 |
| L2 | C4 |
| L3 | C4 |
| L4 | C4 |
| L5 | C4 |
| L6 | C4 |
| L7 | C4 |
| L8 | C4 |
| L9 | C4 |
| L10 | C4 |
| L11 | C4 |
| L12 | C4 |
| L13 | C4 |
| L14 | C4 |
| L15 | C4 |
| L1 | C5 |
| L2 | C5 |
| L3 | C5 |
| L4 | C5 |
| L5 | C5 |
| L6 | C5 |
| L7 | C5 |

TABLE 6-continued

Illustrative Combinations of Linkers and Half-Life Extension Moieties in Peptides of the Invention

| Linker | Half-Life Extension Moiety |
|---|---|
| L8 | C5 |
| L9 | C5 |
| L10 | C5 |
| L11 | C5 |
| L12 | C5 |
| L13 | C5 |
| L14 | C5 |
| L15 | C5 |
| L1 | C6 |
| L2 | C6 |
| L3 | C6 |
| L4 | C6 |
| L5 | C6 |
| L6 | C6 |
| L7 | C6 |
| L8 | C6 |
| L9 | C6 |
| L10 | C6 |
| L11 | C6 |
| L12 | C6 |
| L13 | C6 |
| L14 | C6 |
| L15 | C6 |
| L1 | C7 |
| L2 | C7 |
| L3 | C7 |
| L4 | C7 |
| L5 | C7 |
| L6 | C7 |
| L7 | C7 |
| L8 | C7 |
| L9 | C7 |
| L10 | C7 |
| L11 | C7 |
| L12 | C7 |
| L13 | C7 |
| L14 | C7 |
| L15 | C7 |
| L1 | C8 |
| L2 | C8 |
| L3 | C8 |
| L4 | C8 |
| L5 | C8 |
| L6 | C8 |
| L7 | C8 |
| L8 | C8 |
| L9 | C8 |
| L10 | C8 |
| L11 | C8 |
| L12 | C8 |
| L13 | C8 |
| L14 | C8 |
| L15 | C8 |
| L1 | C9 |
| L2 | C9 |
| L3 | C9 |
| L4 | C9 |
| L5 | C9 |
| L6 | C9 |
| L7 | C9 |
| L8 | C9 |
| L9 | C9 |
| L10 | C9 |
| L11 | C9 |
| L12 | C9 |
| L13 | C9 |
| L14 | C9 |
| L15 | C9 |
| L1 | C10 |
| L2 | C10 |
| L3 | C10 |
| L4 | C10 |
| L5 | C10 |

TABLE 6-continued

Illustrative Combinations of Linkers and Half-Life Extension Moieties in Peptides of the Invention

| Linker | Half-Life Extension Moiety |
|---|---|
| L6 | C10 |
| L7 | C10 |
| L8 | C10 |
| L9 | C10 |
| L10 | C10 |
| L11 | C10 |
| L12 | C10 |
| L13 | C10 |
| L14 | C10 |
| L15 | C10 |
| L16 | C10 |
| L17 | C10 |
| L18 | C10 |

In some embodiments there may be multiple linkers present between the peptide the conjugated moiety, e.g., half-life extension moiety, e.g., as depicted in Table 7.

TABLE 7

Illustrative Combinations of Linkers and Half-Life Extension Moieties in Peptides of the Invention

| Linker | Half-Life Extension Moiety | Linker | Half-Life Extension Moiety |
|---|---|---|---|
| L1-L2 | C10 | L1-L2 | C8 |
| L2-L5-L3 | C10 | L2-L5-L3 | C8 |
| L3-L8 | C10 | L3-L8 | C8 |
| L1-L2-L3 | C10 | L1-L2-L3 | C8 |
| L5-L3-L3-L3 | C10 | L5-L3-L3-L3 | C8 |

In certain embodiments, the half-life of the Peptides of the Invention that include a conjugated chemical substituent, i.e., a half-life extension moiety, is at least 100%, at least 120%, at least 150%, at least 200%, at least 250%, at least 300%, at least 400%, or at least 500% of the half-life of the same peptide but without the conjugated chemical substituent. In certain embodiments, the lipophilic substituents and/or polymeric moieties enhance the permeability of the peptide through the epithelium and/or its retention in the lamina propria. In certain embodiments, the permeability through the epithelium and/or the retention in the lamina propria of a Peptide of the Invention that includes a conjugated chemical substituent is at 100%, at least 120%, at least 150%, at least 200%, at least 250%, at least 300%, at least 400%, or at least 500% of the half-life of the same peptide but without the conjugated chemical substituent.

In certain embodiments, a side chain of one or more amino acid residues (e.g., Lys residues) in a Peptide of the Invention is conjugated (e.g., covalently attached) to a lipophilic substituent. The lipophilic substituent may be covalently bonded to an atom in the amino acid side chain, or alternatively may be conjugated to the amino acid side chain via one or more spacers. The spacer, when present, may provide spacing between the peptide subunit and the lipophilic substituent. In particular embodiments, the Peptides of the Invention comprise any of the conjugated moieties disclosed herein.

In certain embodiments, the lipophilic substituent may comprise a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A lipophilic substituent may be conjugated to any amino acid side chain in a Peptide of the Invention. In certain embodiments, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. In certain embodiments, the lipophilic substituent is conjugated to Lys. An amino acid shown as Lys in any of the Formula provided herein may be replaced by, e.g., Dbu, Dpr or Orn where a lipophilic substituent is added.

In certain embodiments, the Peptides of the Invention may be modified, e.g., to enhance stability, increase permeability, or enhance drug like characteristics, through conjugation of a chemical moiety to one or more amino acid side chain within the peptide. For example, the N (epsilon) of lysine N (epsilon), the β-carboxyl of aspartic, or the γ-carboxyl of glutamic acid may be appropriately functionalized. Thus, to produce the modified peptide, an amino acid within the peptide may be appropriately modified. Further, in some instances, the side chain is acylated with an acylating organic compound selected from the group consisting of: Trifluoropentyl, Acetyl, Octanyl, Butyl, Pentyl, Hexyl, Palmityl, Trifluoromethyl butyric, cyclopentane carboxylic, cyclopropylacetic, 4-fluorobenzoic, 4-fluorophenyl acetic, 3-Phenylpropionic, tetrahedro-2H-pyran-4carboxylic, succinic acid glutaric acid or bile acids. One having skill is the art will appreciate that a series of conjugates can be linked, e.g., for example PEG4, isoglu and combinations thereof. One having skill is the art will appreciate that an amino acid with the peptide can be isosterically replaced, for example, Lys may be replaced for Dap, Dab, α-MeLys or Orn. Examples of modified residues within a peptide are shown in Table 8.

TABLE 8
| Examples of modified Lysine, Asp and Asn within the peptide |
|---|
| 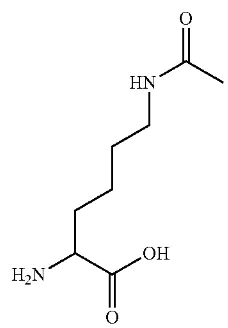 |
| $N^e$-Lys(Ac) |
| 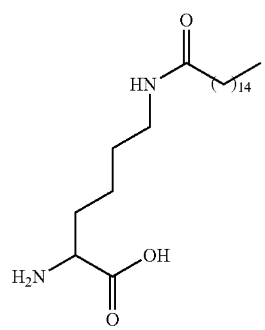 |
| $N^e$-Lys(Palm) |
| 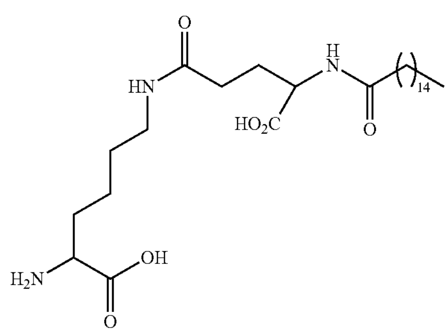 |
| $N^e$-Lys-gamaGlu-Palm |
| 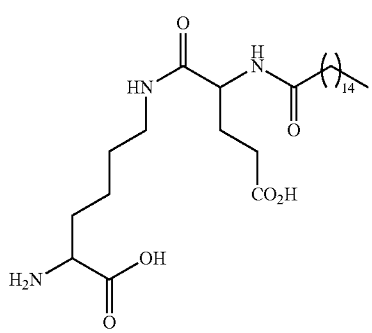 |
| $N^e$-Lys-isoGlu-Palm |

TABLE 8-continued
| Examples of modified Lysine, Asp and Asn within the peptide |
| --- |
| 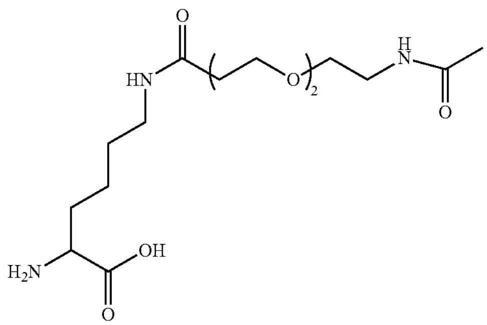 |
| $N^e$-Lys(PEG2-Ac) |
| 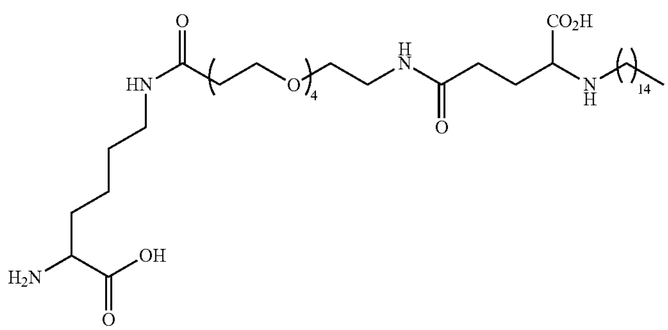 |
| $N^e$-Lys(PEG4-isoGlu-Palm) |
| 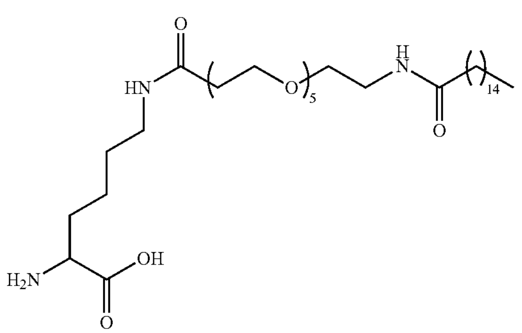 |
| $N^e$-Lys(PEG)$_5$-Palm |
| 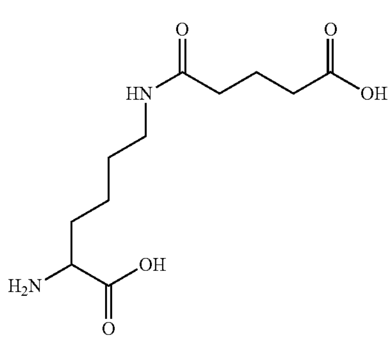 [SMILES: NC(CCCCNC(=O)CCCC(=O)O)C(=O)O] |
| $N^e$-Lys(succinic acid) |

TABLE 8-continued
| Examples of modified Lysine, Asp and Asn within the peptide |
| --- |
| 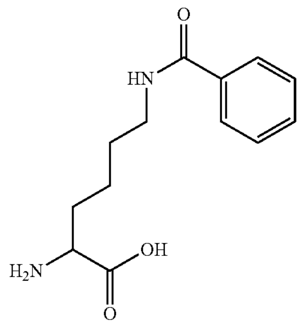 [SMILES: NC(CCCCNC(=O)c1ccccc1)C(=O)O] |
| $N^e$-Lys(glutaric acid) |
| 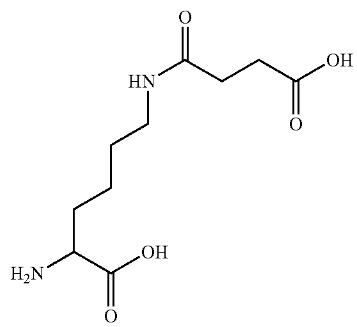 [SMILES: NC(CCCCNC(=O)CCC(=O)O)C(=O)O] |
| $N^e$-Lys(Pyroglutaric acid) |
| 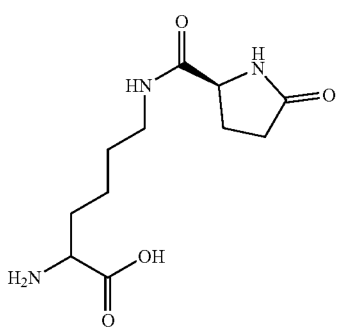 [SMILES: NC(CCCCNC(=O)[C@@H]1CCC(=O)N1)C(=O)O] |
| $N^e$-Lys(Benzoic acid) |
| 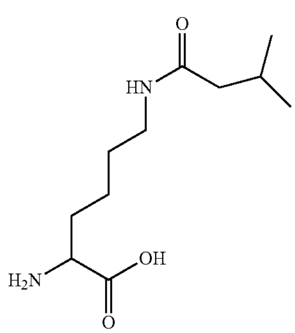 [SMILES: CC(C)CC(=O)NCCCCC(N)C(=O)O] |
| $N^e$-Lys(IVA) |

TABLE 8-continued

| Examples of modified Lysine, Asp and Asn within the peptide |
|---|
| 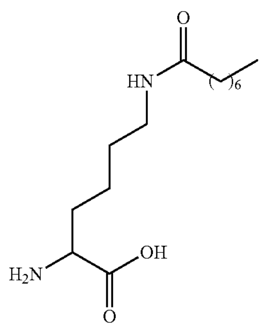<br>$N^e$-Lys(octanoic acid) |
| 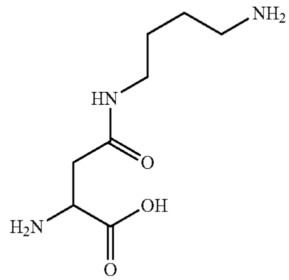 [SMILES: NCCCCNC(=O)CC(N)C(=O)O]<br>Asp(1,4 diaminobutane) |
| 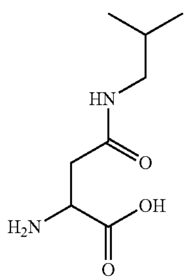<br>Asn(isobutyl) |
| 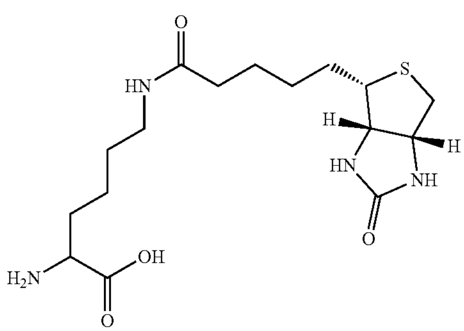 [SMILES: NC(CCCCNC(=O)CCCC[C@@H]1SC[C@@H]2NC(=O)N[C@@H]21)C(=O)O]<br>$N^e$-Lys(Biotin) |

In further embodiments of the invention, alternatively or additionally, a side-chain of one or more amino acid residues in a Peptide of the Invention is conjugated to a polymeric moiety, for example, in order to increase solubility and/or half-life in vivo (e.g. in plasma) and/or bioavailability. Such modifications are also known to reduce clearance (e.g. renal clearance) of therapeutic proteins and peptides.

As used herein, "Polyethylene glycol" or "PEG" is a polyether compound of general Formula $H—(O—CH_2—CH_2)_n—OH$. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 Da, PEO to polymers with a molecular mass above 20,000 Da, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 Da to 10,000,000 Da. While PEG and PEO with different molecular weights find use in different applications, and have different physical properties (e.g., viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are PEGs that are prepared for purpose of half-life extension, for example, mono-activated, alkoxy-terminated polyalkylene oxides (POA's) such as mono-methoxy-terminated polyethyelene glycols (mPEG's); bis activated polyethylene oxides (glycols) or other PEG derivatives are also contemplated. Suitable polymers will vary substantially by weights ranging from about 200 Da to about 40,000 Da or from about 200 Da to about 60,000 Da are usually selected for the purposes of the present invention. In certain embodiments, PEGs having molecular weights from 200 to 2,000 or from 200 to 500 are used. Different forms of PEG may also be used, depending on the initiator used for the polymerization process-a common initiator is a monofunctional methyl ether PEG, or methoxypoly(ethylene glycol), abbreviated mPEG.

Lower-molecular-weight PEGs are also available as pure oligomers, referred to as monodisperse, uniform, or discrete. These are used in certain embodiments of the present invention.

PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear. The numbers that are often included in the names of PEGs indicate their average molecular weights (e.g. a PEG with n=9) would have an average molecular weight of approximately 400 daltons, and would be labeled PEG 400.

As used herein, "PEGylation" is the act of covalently coupling a PEG structure to the Peptides of the Invention, which is then referred to as a "PEGylated peptide". In certain embodiments, the PEG of the PEGylated side chain is a PEG with a molecular weight from about 200 to about 40,000. In certain embodiments, the PEG of a PEGylated spacer is PEG3, PEG4, PEG5, PEG6, PEG7, PEG8, PEG9, PEG10, or PEG11. In certain embodiments, the PEG of a PEGylated spacer is PEG3 or PEG8.

Other suitable polymeric moieties include poly-amino acids such as poly-lysine, poly-aspartic acid and poly-glutamic acid (see for example Gombotz, et al. (1995), Bioconjugate Chem., vol. 6:332-351; Hudecz, et al. (1992), Bioconjugate Chem., vol. 3, 49-57 and Tsukada, et al. (1984), J. Natl. Cancer Inst., vol. 73,: 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a Peptide of the Invention may comprise two or more such polymeric moieties, in which case the total molecular weight of all such moieties will generally fall within the ranges provided above.

In some embodiments, the polymeric moiety is coupled (by covalent linkage) to an amino, carboxyl or thiol group of an amino acid side chain. Certain examples are the thiol group of Cys residues and the epsilon amino group of Lys residues, and the carboxyl groups of Asp and Glu residues may also be involved.

One of ordinary skill in the art will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two-step process. As used herein, for a single oxidation step, the trityl protecting group is often employed during assembly, allowing deprotection during cleavage, followed by solution oxidation. When a second disulfide bond is required, one has the option of native or selective oxidation. For selective oxidation requiring orthogonal protecting groups, Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation, the trityl protecting group is used for all cysteines, allowing for natural folding of the peptide. A skilled worker will be well aware of suitable techniques which can be used to perform the oxidation step.

Several chemical moieties, including poly(ethylene)glycol, react with functional groups present in the twenty naturally occurring amino acids, such as, for example, the epsilon amino group in lysine amino acid residues, the thiol present in cysteine amino acid residues, or other nucleophilic amino acid side chains. When multiple naturally occurring amino acids react in a peptide, these non-specific chemical reactions result in a final Peptide of the Invention that contains many isomers of peptides conjugated to one or more poly(ethylene)glycol strands at different locations within the Peptides of the Invention.

One advantage of certain embodiments of the invention includes the ability to add one or more chemical moiety (such as PEG) by incorporating one or more non-natural amino acid(s) that possess unique functional groups that react with an activated PEG by way of chemistry that is unreactive with the naturally occurring amino acids present in the Peptides of the Invention. For example, azide and alkyne groups are unreactive with all naturally occurring functional groups in a protein. Thus, a non-natural amino acid may be incorporated in one or more specific sites in a Peptide of the Invention where PEG or another modification is desired without the undesirable non-specific reactions. In certain embodiments, the particular chemistry involved in the reaction results in a stable, covalent link between the PEG strand and the Peptides of the Invention. In addition, such reactions may be performed in mild aqueous conditions that are not damaging to most peptides. In certain embodiments, the non-natural amino acid residue is AHA.

Chemical moieties attached to natural amino acids are limited in number and scope. By contrast, chemical moieties attached to non-natural amino acids can utilize a significantly greater spectrum of useful chemistries by which to attach the chemical moiety to the target molecule. Essentially any target molecule, including any protein (or portion thereof) that includes a non-natural amino acid, e.g., a non-natural amino acid containing a reactive site or side chain where a chemical moiety may attach, such as an aldehyde- or keto-derivatized amino acid, can serve as a substrate for attaching a chemical moiety.

Numerous chemical moieties may be joined or linked to a particular molecule through various known methods in the art. A variety of such methods are described in U.S. Pat. No. 8,568,706. As an illustrative example, azide moieties may be useful in conjugating chemical moieties such as PEG or others described herein. The azide moiety serves as a reactive functional group, and is absent in most naturally occurring compounds (thus it is unreactive with the native amino acids of naturally occurring compounds). Azides also undergo a selective ligation with a limited number of reaction partners, and azides are small and can be introduced to biological samples without altering the molecular size of significantly. One reaction that allows incorporation or introduction of azides to molecules is the copper-mediated Huisgen [3+2] cycloaddition of an azide. This reaction can be used for the selective PEGylation of peptide. (Tornoe et al., J. Org. Chem. 67:3057, 2002; Rostovtsev et al., Angew. Chem., Int. Ed. 41:596, 2002; and Wang et al., J. Am. Chem. Soc. 125:3192, 2003, Speers et al., J. Am. Chem. Soc., 2003, 125, 4686).

In another embodiment, the Peptides of the Invention peptides may have one or more amino acid residues deleted from the amino acid sequence of native peptide, or a region S, alone or in combination with one or more insertions or substitutions. In one aspect, the GIP analog or peptides of the invention may have one or more amino acid residues deleted from the N-terminus or C-terminus of a native GIP. In another embodiment, the Peptide of the Invention may have one or more amino acid residues deleted at amino acid positions 1 through 42 of a native GIP, GIP (1-14), GIP (1-26), GIP (1-30), GIP (1-39), GIP (19-26), GIP (19-30), GIP (19-39) or GIP (19-42) or a region S. Such deletions may include more than one consecutive or non-consecutive deletion. In an exemplary embodiments no more than 1, no more than 2, no more than 3, no more than 4, or no more than 5 amino acids are deleted from a native GIP, from GIP (1-30), GIP (1-14), GIP (1-26), GIP (1-39), GIP (19-30), GIP (19-26), GIP (19-39) or GIP (19-42) or from a region S as when region is exendin (31-39) or exendin (27-39) for example. In one embodiment the native GIP is human, rat, mouse, porcine or bovine.

In one embodiment of the Peptides of the Invention, a GIP peptide, either analog, derivative or hybrid, when intended for use as an agonist, does not include a deletion at any one of positions 1-15, corresponding to positions YAEGTFISDYSIAMD (SEQ ID NO: 27) of the N-terminal sequence of GIP. In other words, each of the corresponding 1-15 positions of GIP will be present, although they may be substituted or derivatized. In a further embodiment the agonist GIP compound does not include a deletion at any one of positions 4-15, corresponding to positions GTFISDYSIAMD (SEQ ID NO: 28), of the C-terminal sequence of GIP. In other words, each of the corresponding 4-15 positions of GIP will be present, although they may be substituted or derivatized. Accordingly, in embodiments of an agonist GIP compound, each of the positions 1-15 or 4-15 will be present and occupied by the amino acid present in that position of a naturally-occurring GIP species or by a substitution or derivative thereof. In yet another embodiment of agonist GIP compounds, excluded from the various embodiments described herein are the GIP compounds that did not demonstrate adequate receptor binding activity or receptor activation activity as shown.

In one embodiment of the Peptide of the Invention, a GIP peptide, either analog, derivative or hybrid, when intended for use as an agonist, does not include a deletion at any one of positions 1-15, corresponding to positions YAEGTFISDYSIAMD (SEQ ID NO: 27), of the N-terminal sequence of GIP. In other words, each of the corresponding 1-15 positions of GIP will be present, although they may be substituted or derivatized. In a further embodiment the agonist GIP compound does not include a deletion at any one of positions 4-15, corresponding to positions, of the C-terminal sequence of GIP. In other words, each of the corresponding 4-15 positions of GIP will be present, although they may be substituted or derivatized.

In another embodiment of the Peptide of the Invention, a GIP analog or hybrid may have one or more amino acid residues inserted into the amino acid sequence of native GIP from GIP (1-30), GIP (1-14), GIP (1-26), GIP (1-39), GIP (19-30), GIP (19-26), GIP (19-39) or GIP (19-42) or region S, alone or in combination with one or more deletions and/or substitutions. In one aspect, the invention relates to GIP analog or hybrid peptides that have a single insertion, or consecutive or non-consecutive insertions of more than one amino acid residues into the amino acid sequence of native GIP, GIP (1-30), GIP (1-14), GIP (1-26), GIP (1-39), GIP (19-30), GIP (19-26), GIP (19-39) or GIP (19-42), or region S, for example exendin (27-39) and exendin (31-39). In one embodiment the native GIP is human, rat, mouse, porcine or bovine.

In another embodiment of the Peptides of the Invention, a GIP analog or hybrid may include insertions of one or more unnatural amino acids and/or non-amino acids into the sequence of GIP, GIP (1-30), GIP (1-14), GIP (1-26), GIP (1-39), GIP (19-30), GIP (19-26), GIP (19-39) or GIP (19-42), or a region S, for example exendin (27-39) and exendin (31-39). In an exemplary embodiment, the unnatural amino acids inserted into the sequence of GIP, GIP (1-30), GIP (1-14), GIP (1-26), GIP (1-39), GIP (19-30), GIP (19-26), GIP (19-39) or GIP (19-42) or region S, for example exendin (27-39) and exendin (31-39) may be beta-turn mimetics or linker molecules. In further such embodiments the native GIP can be human, rat, mouse, porcine or bovine.

Accordingly, while compounds are shown with optional linking groups, in one embodiment of the sequences herein, the linker is a Gly linker, for example Gly-Gly-Gly, or a betaAla linker, for example betaAla-betaAla; all of which are specifically envisioned. Linker molecules of particular interest include aminocaproyl ("Aca"), beta-alanyl, and 8-amino-3,6-dioxaoctanoyl. Further in other embodiments a beta-turn mimetic is used, which includes mimic A: N-(3S,6S,9S)-2-oxo-3-amino-1-azabicyclo[4.3.0]-nonane-9-carboxylic acid, mimic B: N-(3S,6S,9R)-2-oxo-3-amino-7-thia-1-azabicyclo[4.3.0]-nonane-9-carboxylic acid, and also Ala-Aib and Ala-Pro dipeptides.

In another embodiment of the Peptides of the Invention, a GIP analog or hybrid may include insertions of polyamino acid sequences (e.g., poly-his, poly-arg, poly-lys, poly-ala, etc.) at either terminus of the polypeptide, known as "extensions" or "tails."

In some embodiments novel Peptides of the Invention comprise amino acid sequence insertions include an alanine substitution at each amino acid position along the length of native GIP, GIP (1-30), GIP (1-14), GIP (1-26), GIP (1-39), GIP (19-30), GIP (19-26), GIP (19-39) or GIP (19-42), or region S, for example exendin (27-39) and exendin (31-39).

The Peptides of the Invention also include derivatives of the GIP analogs and hybrid peptides. Such derivatives include GIP analog and hybrid polypeptides conjugated to one or more water soluble polymer molecules, such as polyethylene glycol ("PEG") or fatty acid chains of various lengths (e.g., stearyl, palmitoyl, octanoyl, etc.), or by the addition of polyamino acids, such as poly-his, poly-arg, poly-lys, and poly-ala. Modifications to the polypeptides can also include small molecule substituents, such as short alkyls and constrained alkyls (e.g., branched, cyclic, fused, adamantyl), and aromatic groups. The water-soluble polymer molecules will preferably have a molecular weight ranging from about 500 to about 20,000 Daltons.

Such polymer-conjugations and small molecule substituent modifications may occur singularly at the N- or C-terminus or at the side chains of amino acid residues within the sequence of the GIP analog and hybrid polypeptides. Alternatively, there may be multiple sites of derivatization along the GIP analog and hybrid peptide. Substitution of one or more amino acids with lysine, aspartic acid, glutamic acid, or cysteine may provide additional sites for derivatization. See, e.g., U.S. Pat. Nos. 5,824,784 and 5,824,778. In one embodiment, the Peptides of the Invention may be conjugated to one, two, or three polymer molecules.

A water-soluble polymer molecule is preferably linked to an amino, carboxyl, or thiol group, and may be linked by N or C termini, or at the side chains of lysine, aspartic acid, glutamic acid, or cysteine. Alternatively, water-soluble polymer molecules may be linked with diamine and dicarboxylic groups. In an exemplary embodiment, the Peptides of the Invention are conjugated to one, two, or three PEG molecules through an epsilon amino group on a lysine amino acid.

The Peptides of the Invention also include chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of, for example, the GIP analog and hybrid peptides. In one embodiment, the C-terminus of these peptides may have a free —OH or —$NH_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group or a Fmoc group. In an exemplary embodiment, cyclization can be through the formation of disulfide bridges. Alternatively, there may be multiple sites of chemical alteration along the Peptides of the Invention.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the component peptide of the Peptide of the Invention, may be identical to the sequences of for example a GIP described herein, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be identical to the sequences of for example a novel GIP analog and hybrid peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

In another embodiment the bond between the second and third residues that is a target for cleavage by DPP-IV is replaced to a peptidase-resistant bond as disclosed herein.

Peptoid derivatives of the Peptides of the Invention represent another class of peptide mimetics that retain the important structural determinants for biological activity, yet eliminate the peptide bonds, thereby conferring resistance to proteolysis (Simon, et al., Proc. Natl. Acad. Sci. USA, 89:9367-9371 (1992), incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the GIP peptides may be replaced with the N-substituted glycine corresponding to the replaced amino acid.

In one embodiment the Peptides of the Invention include combinations of the above-described modifications, i.e., deletion, insertion, and substitution.

Also included within the scope of the invention are component peptides wherein the indicated amino acid residue is chemically modified or derivatized (e.g., through fatty acid derivatization, PEGylation, amidation, glycolization, etc.). Exemplary embodiments include derivatization of a lysine residue, particularly at position 16 or 30. Also contemplated within the scope of the invention are D-amino acid residues of the indicated amino acids. In another embodiment, exemplary GIP analog or hybrid polypeptides include the polypeptides of the formulas with internal deletions, particularly in areas not corresponding to the active sites as described herein.

Exemplary Peptides of the Invention can comprise substitutions of unnatural amino acids. Exemplary derivatives of for example the GIP analog or hybrid peptides of the invention include polymer-conjugated GIP analog or hybrid peptides, wherein the GIP analog or hybrid peptide includes any of the above-described insertions, deletions, substitutions, or combinations thereof, and the polymer molecule is conjugated at a lysine residue. In one embodiment, the Peptides of the Invention include a derivative or substitution of the methionine and have a longer duration of action compared to human GIP or to the analog. For example, an octyl-glycine at the methionine increases the duration of action of the compound in vivo. Duration of action was increased to at least 4 hours by this modification. Accordingly, in one embodiment are Peptides of the Invention conjugated to one or more water soluble polymer molecules, such as polyethylene glycol ("PEG") or fatty acid chain of various lengths (e.g., stearyl, palmitoyl, octanoyl, etc.), or by the addition of polyamino acids, such as poly-his, poly-arg, poly-lys, poly-glu and poly-ala. Modifications to the polypeptides can also include small molecule substituents, such as short alkyls and constrained alkyls (e.g., branched, cyclic, fused, adamantyl), and aromatic groups.

Further specifically envisioned are D-Tyrl and D-Ala2 variants of each peptide component herein. In yet other embodiments envisioned are variants of each of the above sequences where the Peptide of the Invention is modified by one, two or three modifications as described herein. Exemplary modifications are those at the first, second or third N-terminal amino acid of GIP that impart DPP-IV resistance superior to that of native GIP. In yet a further embodiment the novel Peptides of the Invention comprise a C-terminal amide.

In a further embodiment the Peptides of the Invention comprise a half-life at least twice that of human GIP (1-30)amide. Further the half-life can be at least 1, 2, 3, 4, 5, 6, 7, 8, 9, 10, 12, 14, 16, 18, 20, 22, 24, 36, 48, 72, or 96 hours. In a particular embodiment, the half-life can be at least 24 hours.

In another embodiment is a pharmaceutically acceptable salt of a Peptide of the Invention. The Peptides of the Invention can be formulated in a composition comprising a pharmaceutically acceptable carrier.

Synthesis of Peptides of the Invention

The Peptides of the Invention may be synthesized by many techniques that are known to those skilled in the art. In certain embodiments, peptide subunits are synthesized, purified, and dimerized using the techniques known in the art. In certain embodiments, the invention provides a method of producing a Peptide of the Invention (or subunit thereof), comprising chemically synthesizing a peptide comprising, consisting of, or consisting essentially of a peptide having an amino acid sequence described herein, including but not limited to any of the amino acid sequences set forth in any of Formulas I-V or in the tables herein. In other embodiments, the peptide is recombinantly synthesized, instead of being chemically synthesized. In certain embodiments, the Peptides of the Invention, and the method comprises synthesizing both monomer subunits of the Peptides of the Invention and then linking the two subunits to produce the Peptides of the Invention. In various embodiments, coupling or linking is accomplished via any of the various methods described herein.

In particular embodiments, methods of producing a Peptide of the Invention (or monomer subunit thereof) further comprise cyclizing the Peptide of the Invention (or monomer subunit thereof) after its synthesis. In particular embodiments, cyclization is accomplished via any of the various methods described herein. In certain embodiments, the present invention provides a method of producing a peptide (or monomer subunit thereof), comprising introducing an intramolecular bond, e.g., a disulfide, an amide, or a thioether bond between two amino acids residues within a peptide comprising, consisting of, or consisting essentially of a peptide having an amino acid sequence described herein, including but not limited to any of the amino acid sequences set forth in any of Formulas (I)-(V), the accompanying Examples or Tables.

The Peptides of the Invention may be prepared using standard recombinant techniques or chemical peptide synthesis techniques known in the art, e.g., using an automated or semi-automated peptide synthesizer, or both.

The Peptides of the Invention can be synthesized in solution or on a solid support in accordance with conventional techniques. Such methods are described, for example, herein and in U.S. Pat. Nos. 6,610,824 and 5,686,411 and in patent application Ser. No. 454,533 (filed Dec. 6, 1999), the entirety of which are incorporated herein by reference. Various automatic synthesizers are commercially available and can be used in accordance with known protocols. See, e.g., Stewart and Young, Solid Phase Peptide Synthesis, 2d. ed., Pierce Chemical Co. (1984); Tam et al, J. Am. Chem. Soc. 105:6442 (1983); Merrifield, Science 232:341-7 (1986); and Barany and Merrifield, The Peptides, Gross and Meienhofer, eds., Academic Press, New York, 1-284 (1979). Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Peptides may also be assembled using an Advanced Chem Tech Synthesizer (Model MPS 350, Louisville, Ky.). Peptides may be purified by RP-HPLC (preparative and analytical) using, e.g., a Waters Delta Prep 3000 system and a C4, C8, or C18 preparative column (10 μ, 2.2×25 cm; Vydac, Hesperia, Calif.). Polypeptides can be synthesized by convergent methods such as "native chemical ligation", and variations thereof, in which two or more peptide fragments with appropriate orthogonally reactive ends are ligated with native amide bond formation. The newly formed peptide can be further ligated to create even longer polypeptides. The individual starting peptides can be derivatized as desired or can be derivatized after a ligation step.

Peptides analogs can be synthesized on a Pioneer continuous flow peptide synthesizer (Applied Biosystems) using PAL-PEG-PS resin (Applied Biosystems) with a loading of 0.2 mmol/g (0.25 mmole scale). Fmoc amino acid (4.0 eq, 1.0 mmol) residues are activated using 4.0 eq HBTU, 4.0 eq of HOBT, 8.0 eq DIEA and coupled to the resin for 1 hour. The Fmoc group is removed by treatment with 20% (v/v) piperidine in dimethylformamide. Final deprotection and cleavage of the peptide from the solid support is performed by treatment of the resin with reagent B (93% TFA, 3% phenol, 3% water and 1% triisopropylsilane) for 2-3 hours. The cleaved peptide is precipitated using tert-butyl methyl ether, pelleted by centrifugation and lyophilized. The pellet is re-dissolved in water (10-15 mL), filtered and purified via reverse phase HPLC using a C-18 column and an acetonitrile/water gradient containing 0.1% TFA. The purified product is lyophilized and analyzed by ESI-LC/MS and analytical HPLC and were demonstrated to be pure (>98%). Mass results all agreed with calculated values.

Alternatively, peptides are assembled on a Symphonyl peptide synthesizer (Protein Technologies, Inc., Woburn, Mass.) using Rink amide resin (Novabiochem, San Diego, Calif.) with a loading of 0.43-0.49 mmol/g at 0.050-0.100 mmol. Fmoc amino acid (Applied Biosystems, Inc. 5.0 eq, 0.250-0.500 mmol) residues are dissolved at a concentration of 0.10 M in 1-methyl-2-pyrrolidinone. All other reagents (HBTU, HOBT and N,N-diisopropylethylamine) are prepared as 0.55 M dimethylformamide solutions. The Fmoc protected amino acids are then coupled to the resin-bound amino acid using, HBTU (2.0 eq, 0.100-0.200 mmol), HOBT (1.8 eq, 0.090-0.18 mmol), N,N-diisopropylethylamine (2.4 eq, 0.120-0.240 mmol) for 2 hours. Following the last amino acid coupling, the peptide is deprotected using 20% (v/v) piperidine in dimethylformamide for 1 hour. Once peptide sequence is completed, the Symphonyl peptide synthesizer is programmed to cleave the resin. Trifluoroacetic acid (TFA) cleavage of the peptide from resin is carried out using a reagent mixture composed of 93% TFA, 3% phenol, 3% water and 1% triisopropylsilane. The cleaved peptide is precipitated using tert-butyl methyl ether, pelleted by centrifugation and lyophilized. The pellet is dissolved in acetic acid, lyophilized and then dissolved in water, filtered and purified via reverse phase HPLC using a $C_{18}$ column and an acetonitrile/water gradient containing 0.1% TFA. Analytical HPLC is used to assess purity of peptide and identity is confirmed by LC/MS and MALDI-MS.

The active protein can be readily synthesized and then screened in screening assays designed to identify reactive peptides.

The Peptides of the Invention may alternatively be produced by recombinant techniques well known in the art. See, e.g., Sambrook et al., Molecular Cloning: A Laboratory Manual, 2d ed., Cold Spring Harbor (1989). The Peptides of the Invention produced by recombinant technologies may be expressed from a polynucleotide. One skilled in the art will appreciate that polynucleotides, including DNA and RNA, that encode such GIP analog or hybrid peptides may be obtained from the wild-type cDNA, e.g. GIP, GLP1, amylin, taking into consideration the degeneracy of codon usage, or may be engineered as desired. These polynucleotide sequences may incorporate codons facilitating transcription and translation of mRNA in microbial hosts. Such manufacturing sequences may readily be constructed according to the methods well known in the art. See, e.g., WO 83/04053. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, Bioorg. Chem. 14:356-77 (1986).

A variety of expression vector/host systems may be utilized to contain and express a Peptide of the Invention coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein.

As such, polynucleotide sequences provided by the invention are useful in generating new and useful viral and plasmid DNA vectors, new and useful transformed and transfected prokaryotic and eukaryotic host cells (including bacterial, yeast, and mammalian cells grown in culture), and new and useful methods for cultured growth of such host cells capable of expression of the present GIP polypeptides. The polynucleotide sequences encoding GIP analogs or hybrids herein may be useful for gene therapy in instances where underproduction of GIP or other component peptide hormone(s) of the hybrid would be alleviated, or the need for increased levels of such would be met.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the Peptides of the Invention. The coding region of for example, the GIP polypeptide cDNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, Cell, 30:933-43 (1982)). The pre-pro-alpha leader coding sequence and GIP polypeptide coding sequence fragments are ligated into a plasmid containing the yeast alcohol dehydrogenase (ADH2) promoter, such that the promoter directs expression of a fusion protein consisting of the pre-pro-alpha factor fused to the mature GIP polypeptide. As taught by Rose and Broach, Meth. Enz. 185:234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., Meth. Enz. 185: 280-97 (1990)). The ADH2 promoter is induced upon exhaustion of glucose in the growth media (Price et al., Gene 55:287 (1987)). The pre-pro-alpha sequence effects secretion of the fusion protein from the cells. Concomitantly, the yeast KEX2 protein cleaves the pre-pro sequence from the mature GIP-polypeptides (Bitter et al., Proc. Natl. Acad. Sci. USA 81:5330-4 (1984)).

Peptides of the Invention may also be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted peptide is purified from the yeast growth medium by, e.g., the methods used to purify peptide from bacterial and mammalian cell supernatants.

Alternatively, the cDNA encoding Peptides of the Invention may be cloned into an expression vector, for example, a baculovirus expression vector pVL1393. This GIP-compound-encoding vector is then used according to the manufacturer's directions (Sigma Chemical Co., St. Louis, MO) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

In another example, the DNA sequence encoding the Peptides of the Invention may be amplified by PCR and cloned into an appropriate vector, for example, pGEX-3X (Pharmacia, Piscataway, N.J.). The pGEX vector is designed to produce a fusion protein comprising glutathione-5-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. For example, the pGEX-3X/GIP analog peptide construct is transformed into *E. coli* XL-1 Blue cells (Agilent, Santa Clara, CA), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl beta-D-Thiogalactopyranoside (Sigma Chemical Co., St. Louis, Mo.). Plasmid DNA from individual transformants is purified and partially sequenced using an automated sequencer to confirm the presence of the desired peptide-encoding gene insert in the proper orientation.

A fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000 ×g. The fusion protein-containing pellet is resuspended in 50 mM Tris, pH 8, and 10 mM EDTA, layered over 50% glycerol, and centrifuged for 30 min. at 6000 ×g. The pellet is resuspended in standard phosphate buffered saline solution (PBS) free of Mg++ and Ca++. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If for example a GST/GIP polypeptide fusion protein is produced in bacteria as a soluble protein, it may be purified using the GST Purification Module (Pharmacia Biotech).

A fusion protein may be subjected to digestion to cleave the GST from the mature GIP analog or hybrid peptide. The digestion reaction (20-40 μg fusion protein, 20-30 units human thrombin (4000 U/mg (Sigma) in 0.5 mL PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the peptide may be confirmed by partial amino acid sequence analysis using an Orbitrap Exploris 490 Mass Spectrometer (ThermoFisher Scientific, Waltham, MA).

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

The Peptides of the Invention may be produced using a combination of both automated peptide synthesis and recombinant techniques. For example, a GIP peptide may contain a combination of modifications including deletion, substitution, and insertion by PEGylation. Such a GIP peptide may be produced in stages. In the first stage, an intermediate GIP peptide containing the modifications of deletion, substitution, insertion, and any combination thereof, may be produced by recombinant techniques as described. Then after an optional purification step as described herein, the intermediate GIP peptide is PEGylated through chemical modification with an appropriate PEGylating reagent (e.g., from NeKtar Transforming Therapeutics, San Carlos, Calif.) to yield the desired GIP peptide. One skilled in the art will appreciate that the above-described procedure may be generalized to apply to a Peptide of the Invention containing a combination of modifications selected from deletion, substitution, insertion, derivation, and other means of modification well known in the art and contemplated by the invention.

It may be desirable to purify the GIP polypeptides generated by the present invention. Peptide purification techniques are well known to those of skill in the art. These techniques involve, at one level, the crude fractionation of the cellular milieu to peptide and non-peptide fractions. Having separated the peptide from other proteins, the peptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

Certain aspects of the invention concern the purification, and in particular embodiments, the substantial purification, of an encoded protein or peptide. The term "purified peptide" as used herein, is intended to refer to a composition, isolatable from other components, wherein the peptide is purified to any degree relative to its naturally obtainable state. A purified peptide therefore also refers to a peptide, free from the environment in which it may naturally occur. Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95% or more of the peptides in the composition.

Various techniques suitable for use in peptide purification will be well known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low-pressure chromatography system. Methods exhibiting a lower degree of relative purification may have advantages in total recovery of protein product, or in maintaining the activity of an expressed protein.

One may optionally purify and isolate such Peptides of the Invention from other components obtained in the process. Methods for purifying a polypeptide can be found in U.S. Pat. No. 5,849,883. These documents describe specific exemplary methods for the isolation and purification of G-CSF compositions that may be useful in isolating and purifying the GIP polypeptides of the present invention. Given the disclosure of these patents, it is evident that one of skill in the art would be well aware of numerous purification techniques that may be used to purify Peptides of the Invention from a given source.

It is contemplated that a combination of anion exchange and immunoaffinity chromatography may be employed to produce purified Peptides of the Invention.

Methods of Treatment

The Peptides of the Invention are useful in treating and preventing metabolic and liver diseases and disorders.

Metabolic diseases and disorders take on many forms, including obesity, diabetes, dyslipidemia, insulin resistance, cellular apoptosis, etc. Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman, Nature 404:635-43 (2000)). It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., Br. Med. J. 301: 835-7 (1990)). Obesity is also a risk factor for the group of conditions called insulin resistance syndrome, or "Syndrome X." Recent estimate for the medical cost of obesity and associated disorders is $2 Trillion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

Diabetes is a disorder of carbohydrate metabolism characterized by hyperglycemia and glucosuria resulting from insufficient production or utilization of insulin. Diabetes severely affects the quality of life of large parts of the populations in developed countries. Insufficient production of insulin is characterized as type 1 diabetes and insufficient utilization of insulin is type 2 diabetes. However, it is now widely recognized that there are many distinct diabetes related diseases which have their onset long before patients are diagnosed as having overt diabetes. Also, the effects from the suboptimal control of glucose metabolism in diabetes gives rise to a wide spectrum of related lipid and cardiovascular disorders.

Dyslipidemia, or abnormal levels of lipoproteins in blood plasma, is a frequent occurrence among diabetics. Dyslipidemia is typically characterized by elevated plasma triglycerides, low HDL (High Density Lipoprotein) cholesterol, normal to elevated levels of LDL (Low Density Lipoprotein) cholesterol and increased levels of small dense, LDL (Low Density Lipoprotein) particles in the blood. Dyslipidemia is one of the main contributors to the increased incidence of coronary events and deaths among diabetic subjects. Epidemiological studies have confirmed this by showing a several-fold increase in coronary deaths among diabetic subjects when compared with non-diabetic subjects. Several lipoprotein abnormalities have been described among diabetic subjects.

Insulin resistance is the diminished ability of insulin to exert its biologically action across a broad range of concentrations. In insulin resistance, the body secretes abnormally high amounts of insulin to compensate for this defect and a state of impaired glucose tolerance develops. Failing to compensate for the defective insulin action, the plasma glucose concentration inevitable rises, resulting in the clinical state of diabetes. It is being recognized that insulin resistance and relative hyperinsulinemia have a contributory role in obesity, hypertension, atherosclerosis and type 2 diabetes. The association of insulin resistance with obesity, hypertension and angina has been described as a syndrome, Syndrome X, having insulin resistance as the common pathogenic link.

Non-alcoholic fatty liver disease (NAFLD) is an umbrella term and encompasses the simple deposition of fat in the liver to more progressive steatosis with associated hepatitis, fibrosis, cirrhosis, and in some cases hepatocellular carcinoma. NAFLD is increasingly common around the world, especially in Western nations. In the United States, it is the most common form of chronic liver disease, affecting about one-quarter of the population. Some individuals with NAFLD can develop nonalcoholic steatohepatitis (NASH), an aggressive form of fatty liver disease, which is marked by liver inflammation and may progress to advanced scarring (cirrhosis) and liver failure. This damage is similar to the damage caused by heavy alcohol use. NAFLD is comprised of non-alcoholic fatty liver (NAFL) and non-alcoholic steatohepatitis (NASH). NAFL is characterized by steatosis of the liver, involving greater than 5% of parenchyma, with no evidence of hepatocyte injury. Whereas, NASH is defined by histologic terms, that is a necroinflammatory process whereby the liver cells become injured in a background of steatosis. The natural history of NAFLD remains incompletely characterized. Studies indicate the incidence of NAFLD increasing in concert with the rising rates of metabolic syndrome. Patients with Type 2 diabetes display a very high risk of developing NASH as well as a two-to-four-fold increased risk of fatty liver associated complications.

Apoptosis is an active process of cellular self-destruction that is regulated by extrinsic and intrinsic signals occurring during normal development. It is well documented that apoptosis plays a key role in regulation of pancreatic endocrine beta cells. There is increasing evidence that in adult mammals the beta-cell mass is subject to dynamic changes to adapt insulin production for maintaining euglycemia in particular conditions, such as pregnancy and obesity. The control of beta cell mass depends on a subtle balance between cell proliferation, growth and programmed cell death (apoptosis). A disturbance of this balance may lead to impairment of glucose homeostasis. For example, it is noteworthy that glucose intolerance develops with aging when beta cell replication rates are reduced and human autopsy studies repeatedly showed a 40-60% reduction of beta cell mass in patients with non-insulin-dependent-diabetes mellitus compared with nondiabetic subjects. It is generally agreed that insulin resistance is an invariable accompaniment of obesity but that normoglycemia is maintained by compensatory hyperinsulinemia until the beta cells become unable to meet the increased demand for insulin, at which point type 2 diabetes begins.

Attempts to treat the multiple abnormalities associated with diabetes have prompted for the administration of several anti-diabetic medicaments in order to address these abnormalities in the different patients. However, the Peptides of the Invention as discussed herein find use, when administered at therapeutically effective amounts, either in monotherapy or in adjunct therapy, in treating or preventing these and other diseases and conditions discussed throughout.

In an embodiment of the invention, reduction of hyperglycemia (e.g., as by a GLP-1 mimetic such as exenatide) in treated diabetic patients sets the stage for intervention. Whereas the chronic hyperglycemic condition in type 2 diabetes patients attenuates GIP's insulinotropic response, improved glycemic control resulting from exenatide treatment would restore responsiveness of the pancreatic beta-cell to GIP stimulation. Administration of Peptides of the Invention will lead to desired normoglycemia in diabetic patients or patients suffering from conditions associated with elevated glucose.

Since currently prescribed anti-diabetic agents (metformin, sulfonyureas, TZDs, SGLT2 inhibitors, etc) are able to achieve various degrees of glycemic control, the combination of Peptides of the Invention with any of these therapies should also elicit an improved response that leads to normalization of glucose levels.

Accordingly, in one embodiment the methods of the present invention are based on the notion that patients can be primed for therapy through prior glucose lowering with other anti-diabetic agents, such as GLP-1, a GLP-1 analog or exendin-4 or other agents, e.g. metformin, sulfonyureas, thiazolidinediones (TZDs), pramlintide, insulin, acarbose, dipeptidyl peptidase (DPP-IV) inhibitors, and SGLT-2 inhibitors. DPP-IV inhibitors are well-known and described for example in published application US20050004117, U.S. Pat. Nos. 6,710,040, and 6,645,995, which are incorporated herein by reference for their compounds. As example of a sulfonylureas (SFUs), which acts on the pancreatic tissue to produce insulin, is Glimepiride.

The Peptides of the Invention can be useful for reducing food intake, reducing appetite, reducing caloric intake, inducing satiety, reducing nutrient availability, causing weight loss, affecting body composition, altering body energy content or energy expenditure, improving lipid profile (including reducing LDL cholesterol and triglyceride levels and/or changing HDL cholesterol levels), slowing gastrointestinal motility, delay gastric emptying, moderating the postprandial blood glucose excursions, preventing or inhibiting glucagon secretion, and decreasing blood pressure. In one embodiment such GIP peptides contain an exendin, GLP1, amylin and/or sCT portion.

Of particular interest as anti-obesity, weight reduction, food reduction, metabolic rate increasing, and body fat reduction and/or fat redistribution peptides are those Peptides of the Invention that contain GIP, GLP-1 an exendin, a GLP-1-GIP receptor co-agonist such as, amylin (i.e., a dual amylin calcitonin receptor agonist), leptin family module that can effectively reduce food intake, change body composition, redistribute fat and/or reduce body weight. In embodiments of particular interest for treating obesity and related diseases and conditions (body fat reduction) as discussed herein, are Peptides of the Invention comprising GIP, an exendin-4 or analog or derivative thereof, an amylin component such as pramlintide or an dual amylin calcitonin receptor agonist, an FN38 family member such as FN38 or an analog or derivative thereof. In another embodiment, the Peptides of the Invention can have at least one, preferably two components, which act on the CNS. Particular areas of the forebrain (telencephalonic- and diencephalonic-derived constituents of the brain) and hindbrain or brainstem (including the midbrain, pons and medulla) have been identified as being involved in controlling energy balance. Forebrain structures or nuclei residing in the hypothalamus involved in food intake and/or body weight modulation include, for example, the arcuate nucleus (ARC), the paraventricular nucleus (PVN), the dorsomedial hypothalamus (DMH), the ventromedial nucleus (VMH), and the lateral hypothalamus nucleus (LHA). Hindbrain structures or nuclei residing in the brainstem involved in food intake and/or body weight modulation include, for example, the nucleus of the solitary tract (NST), the area postrema (AP), and the lateral parabrachial nucleus (lPBN). Brainstem nuclei that control the elements of the consummatory motor control system are likely controlled by primary or second order projections from brainstem regions like the NST, AP, and IPBN. It is noteworthy that the AP, NST and IPBN have all been shown to (collectively and independently) possess their own integrative abilities.

A variety of CNS-directed anti-obesity agents act upon these forebrain structures residing in the hypothalamus involved in food intake and/or body weight modulation. In addition, CNS-directed anti-obesity agents act upon hindbrain structures residing in the brainstem involved in food intake and/or body weight modulation. Such components peptide include, for example, leptin and leptin agonists, ciliary neurotrophic factor (CNTF) and CNTF agonists, peptide YY (PYY) and PYY agonists, exendin and exendin agonists, GLP-1 and GLP-1 agonist, ghrelin and ghrelin antagonists, cholecystokinin (CCK) and CCK agonists, and amylin and amylin agonists, including those described herein.

In certain embodiments, the Peptide of the Invention and method for it use include a first component that predominantly targets the energy balance centers of the hypothalamus, such as the ARC, PVN, VM, and LH. In one embodiment the Peptides of the Invention contain GIP or an analog or derivative thereof and one or more other peptide family component that also target the hypothalamus but at a different location or via a different mechanism of action than the first component. When the GIP peptide contains more than one other peptide family component and these also target the hypothalamus, the more than one other peptide family components may target the same location via the same mechanism of action as each other, or they may target different locations and/or different mechanisms of action. In another embodiment, the GIP peptide then contains one or more other peptide family components that provide one or more additional beneficial therapeutic effects as desired, including an anti-obesity effect via a location or mechanism of action different than the first component and each other, control of blood glucose, cardioprotection, and/or control of hypertension. In certain embodiments, the additional peptide family component is one that predominantly targets the energy balance centers of the hindbrain such as the NST, the AP and the IPBN.

In certain embodiments, the Peptide of the Invention and method for it use include a first component that predominantly targets the energy balance centers of the hindbrain such as the NST, the AP and the IPBN. In one embodiment the GIP peptide further contains one or more other peptide family component that also target the hypothalamus but at a different location or via a different mechanism of action than the first component and each other. In another embodiment, the Peptides of the Invention then contains one or more other peptide family components that provide one or more additional beneficial therapeutic effects as desired, including an anti-obesity effect via a location or mechanism of action different than the first component and each other, control of blood glucose, cardioprotection, and/or control of hypertension. In certain embodiments, the additional peptide family component is one that predominantly targets the energy balance centers of the hypothalamus, such as the ARC, PVN, VM, and LH.

As used herein, an anti-obesity agent that "acts on a forebrain structure involved in food intake and/or body weight modulation" stimulates or suppresses activity of a particular region, e.g., particular nuclei and/or neuronal circuits, in the forebrain. This forebrain stimulation or suppression leads to a reduction in nutrient availability to the body. An anti-obesity agent that "acts on a hindbrain structure involved in food intake and/or body weight modulation" stimulates or suppresses activity of a particular region, e.g., particular nuclei and/or neuronal circuits, in the hindbrain. This hindbrain stimulation or suppression results in a reduction in nutrient availability to the body.

In another aspect, methods for reducing fat mass by increasing the metabolic rate in a subject are provided, where the methods comprise administering a Peptide of the Invention in amounts effective to reduce fat mass by increasing the subject's metabolic rate. Fat mass can be expressed as a percentage of the total body mass. In some embodiments, the fat mass is reduced by at least 1%, at least 5%, at least 10%, at least 15%, at least 20%, or at least 25% over the course of treatment. In one aspect, the subject's lean mass is not decreased over the course of the treatment. In another aspect, the subject's lean mass is maintained or increased over the course of the treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150, 200, 250, 300, 400, 500, 600, 700, 800, 900, or 1000 fewer calories per day.

In another embodiment, methods of use in altering fat distribution, reducing fat mass, or both in a subject are provided. Accordingly, subjects for whom altering body composition is of benefit can also benefit from the present methods. Altered body composition, as intended herein, includes loss or maintenance of body fat, with minimization of loss, maintenance, or gain of lean body mass. In such situations, weight may increase as well as decrease. Accordingly, subjects may be lean, overweight, or obese as these terms are generally used in the art. Methods provided may also include reducing fat in non-adipose tissue while sparing lean mass. Uses for this method include treating diseases such as nonalcoholic steatohepatitis (NASH) or lipodystrophy.

In another embodiment, a method for altering the fat distribution in a subject is provided where the method comprises administering an anti-obesity Peptide of the Invention in amounts effective to alter fat distribution in the subject. In one aspect, the alteration results from an increased metabolism of visceral or ectopic fat, or both in the subject. By "fat distribution" is meant the location of fat deposits in the body. Such locations of fat deposition include, for example, subcutaneous, visceral and ectopic fat depots. By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference. By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body. By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases. In some embodiments, the method involves the metabolism of visceral or ectopic fat or both at a rate of at least about 5%, 10%, 15%, 20%, 25%, 30%, 40%, or 50% greater than for subcutaneous fat. In one aspect, the methods result in a favorable fat distribution. In one embodiment, favorable fat distribution is an increased ratio of subcutaneous fat to visceral fat, ectopic fat, or both. In one aspect, the method involves an increase in lean body mass, for example, as a result of an increase in muscle cell mass.

In another embodiment, methods for reducing the amount of subcutaneous fat in a subject are provided, wherein the method comprises administering, to a subject in need thereof, an anti-obesity Peptide of the Invention in amounts effective to reduce the amount of subcutaneous fat in the subject. In one instance, the amount of subcutaneous fat is reduced in a subject by at least about 5%. In other instances, the amount of subcutaneous fat is reduced by at least about 10%, 15%, 20%, 25%, 30% 40%, or 50% compared to the subject prior to administration of the anti-obesity Peptide of the Invention.

The methods described herein can be used to reduce the amount of visceral fat in a subject. In one instance, the visceral fat is reduced in a subject by at least about 5%. In other instances, the visceral fat is reduced in the subject by at least about 10%, 15%, 20%, 25%, 30% 40%, or 50% compared to the subject prior to administration of the anti-obesity Peptide of the Invention. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In another embodiment, a method for preventing the accumulation of ectopic fat or reducing the amount of ectopic fat in a subject is provided, wherein the method comprises administering, to a subject in need thereof, an anti-obesity Peptide of the Invention in amounts effective to prevent accumulation of ectopic fat or to reduce the amount of ectopic fat in the subject. In one instance, the amount of ectopic fat is reduced in a subject by at least about 5% compared to the subject prior to administration of the anti-obesity Peptide of the Invention. In other instances, the amount of ectopic fat is reduced in a subject by at least about 10%, or by at least about 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In another embodiment, methods are provided for producing a more favorable fat distribution in a subject, where the method comprises administering to a subject a Peptide of the Invention that is effective as an anti-obesity agent in an amount effective to produce a favorable fat distribution. In one embodiment, administration of an anti-obesity Peptide of the Invention reduces the amount of visceral fat or ectopic fat, or both, in a subject. In one embodiment is administered an anti-obesity Peptide of the Invention that comprises at least one family module that acts upon forebrain structures involved in food intake or body weight modulation or both in combination with at least one family module that acts upon hindbrain structures involved in food intake or body weight modulation or both. In one embodiment, the methods preferentially reduce the amount of visceral or ectopic fat, or a combination of both, over the reduction in subcutaneous fat. Such methods result in a higher ratio of subcutaneous fat to visceral fat or ectopic fat. Such improved ratios may result in a reduced risk of the development of cardiovascular diseases, polycystic ovary syndrome, metabolic syndrome, or any combinations thereof. In one embodiment, ectopic or visceral fat is metabolized at a rate 5% greater than subcutaneous fat. In other embodiments, ectopic or visceral fat is metabolized at a rate at least 10% 15%, 20%, 25%, 30% 50%, 60%, 70%, 80%, 90%, or 100% greater than subcutaneous fat.

Of particular interest for anti-obesity, body weight and fat composition related treatments as discussed herein are Peptides of the Invention containing for example GIP, an exendin, amylin, (i.e. a dual amylin calcitonin receptor agonist), leptin, or a GLP-1-GIP receptor co-agonist. In yet a further embodiment, a Peptide of the Invention contains at least two of these peptide family modules. The Peptides of the Invention can be administered either alone or in combination with a second anti-obesity agent such as an amylin, leptin, or exendin family peptide.

In still another aspect, provided is a method for the administration of a therapeutically effective amount of a Peptide of the Invention effective as an anti-obesity agent administered in combination with glucocorticosteroids. Glucocorticosteroids have the adverse effect of increasing fat mass and decreasing lean mass. Accordingly, it is contemplated that the anti-obesity agent combination can be used in conjunction with glucocorticosteroids under conditions where glucocorticosteroid use is beneficial, in order to counteract the adverse effect of the glucocorticosteroid.

As discussed herein, a Peptide of the Invention can be administered separately or together with one or more other agents in order to obtain additional benefits or to enhance the effect of either the Peptide of the Invention or the other agent. For example, an anti-obesity Peptide of the Invention can be administered with an anti-obesity agent or a cardioprotective or anti-hypertension agent, depending on the risk factors pertinent to the subject in need of treatment and desired treatment outcome. Exemplary anti-obesity agents for administration (either separately or mixed; either prior to, concomitantly or after) with a Peptide of the Invention include serotonin (5HT) transport inhibitors, including, but not limited to, paroxetine, fluoxetine, fenfluramine, fluvoxamine, sertraline, and imipramine. Anti-obesity agents also include selective serotonin reuptake inhibitors, including, but not limited to dexfenfluramine, fluoxetine, sibutramine and combinations thereof and those described in U.S. Pat. No. 6,365,633 and PCT Patent Application Publication Nos. WO 01/27060 and WO 01/162341, which are hereby incorporated by reference in their entirety. Such 5HT transport inhibitors and serotonin reuptake inhibitors, analogs, derivatives, preparations, formulations, pharmaceutical compositions, doses, and administration routes have previously been described.

Anti-obesity agents also include selective serotonin agonists and selective 5-HT2C receptor agonists, including, but not limited to, U.S. Pat. No. 3,914,250; and PCT Application Publication Nos. WO 02/36596, WO 02/48124, WO 02/10169, WO 01/66548, WO 02/44152; WO 02/51844, WO 02/40456, and WO 02/40457, which are hereby incorporated by reference in their entirety. Such selective serotonin agonists and 5-HT2C receptor agonists, compositions containing such agonists, and administration routes appropriate for use in the methods provided are known in the art. See, for example, Halford et al. (2005) Curr. Drug Targets 6:201-213 and Weintraub et al. (1984) Arch. Intern. Med. 144:1143-1148.

Anti-obesity agents also include antagonists/inverse agonists of the central cannabinoid receptors (the CB-1 receptors), including, but not limited to, rimonabant (Sanofi Synthelabo), and SR-147778 (Sanofi Synthelabo). CB-1 antagonists/inverse agonists, derivatives, preparations, formulations, pharmaceutical compositions, doses, and administration routes have previously been described, for example, in U.S. Pat. Nos. 6,344,474, 6,028,084, 5,747,524, 5,596,106, 5,532,237, 4,973,587, 5,013,837, 5,081,122, 5,112,820, 5,292,736, 5,624,941; European Patent Application Nos. EP-656 354 and EP-658546; and PCT Application Publication Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, and WO 02/076949, which are hereby incorporated by reference in their entirety.

Anti-obesity agents also include melanocortins and melanocortin agonists. The receptor MC4R appears to play a role in energy balance and obesity. See, for example, Anderson et al., Expert Opin. Ther. Patents 11:1583-1592 (2001), Speake et al., Expert Opin. Ther. Patents 12:1631-1638 (2002), Bednarek et al., Expert Opin. Ther. Patents 14:327-336 (2004). Melanocortin agonists, including, but not limited to, MC4R agonists, and composition containing such agonist appropriate for use in the methods provided are known in the art. MCR agonists, MC4R agonists, derivatives, preparations, formulation, pharmaceutical compositions, doses, and administration routes have previously been described, for example, in the following PCT patent applications, which are hereby incorporated by reference in their entirety: WO 03/007949, WO 02/068388, WO 02/068387, WO 02/067869, WO 03/040117, WO 03/066587, WO 03/068738, WO 03/094918, and WO 03/031410.

Anti-obesity agents also include metabotropic glutamate subtype 5 receptor (mGluR5) antagonists, including, but are not limited to, compounds such as 2-methyl-6-(phenylethynyl)-pyridine (MPEP) and (3-[(2-methyl-1,3-thiazol-4-yl) ethynyl]pyridine) (MTEP) and those compounds described in Anderson et al. J. Eur. J. Pharmacol. 473:35-40 (2003); Cosford et al. Bioorg. Med. Chem. Lett. 13 (3): 351-4 (2003); and Anderson et al. J. Pharmacol. Exp. Ther. 303: 1044-1051 (2002).

Anti-obesity agents also include topiramate, phentermine or combinations thereof indicated as an anti-convulsant and an anti-convulsant, but also shown to increase weight loss.

Anti-obesity agents also include neuropeptide Y1 (NPY1) antagonists and NPY5 antagonists. NPY1 and NPY5 antagonists are known in the art. See, for example Duhault et al. (2000) Can. J. Physiol. Pharm. 78:173-185, and U.S. Pat. Nos. 6,124,331, 6,214,853, and 6,340,683. NPY1 and NPY5 antagonists, derivatives, preparations, formulation, pharmaceutical compositions, doses, and administration routes have previously been described. NPY1 antagonists useful in the compositions and methods provided include U.S. Pat. No. 6,001,836; and PCT Application Publication Nos. WO 96/14307, WO 01/23387, WO 99/51600, WO 01/85690, WO 01/85098, WO 01/85173, and WO 01/89528, which are hereby incorporated by reference in their entirety. NPY5 antagonists useful in compositions and methods of use provided herein, include, but are not limited to, the compounds described in: U.S. Pat. Nos. 6,140,354, 6,191,160, 6,258,837, 6,313,298, 6,337,332, 6,329,395, 6,340,683, 6,326,375, and 6,335,345; European Patent Nos. EP-01010691, and EP-01044970; and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, WO 02/49648, and WO 01/14376.

Anti-obesity agents also include melanin-concentrating hormone (MCH) antagonists including melanin-concentrating hormone 1 receptor (MCHIR) antagonists, such as T-226296 (Takeda) and melanin-concentrating hormone 2 receptor (MCH2R) antagonists. MCH receptor antagonists, derivatives, preparations, formulation, pharmaceutical compositions, doses, and administration routes have previously been described, for example, in U.S. Patent Application Publication Nos. 2005/0009815, 2005/0026915, 2004/0152742, 2004/0209865; PCT Patent Application Publication Nos. WO 01/82925, WO 01/87834, WO 02/06245, WO 02/04433, and WO 02/51809; and Japanese Patent Application No. JP 13226269, which are hereby incorporated by reference in their entirety.

Anti-obesity agents also include opioid antagonists, including, but not limited to those described in PCT Application No. WO 00/21509. Specific opioid antagonists useful in compositions and methods of use provided herein include, but are not limited to, nalmefene (REVEX®), 3-methoxynaltrexone naloxone, naltrexone, bupropion, naloxonazine, beta-funaltrexamine, deltal ([D-Ala2,Leu5,Cys6]-enkephalin (DALCE), naltrindole isothiocyanate, and nor —binaltorphamine or combinations thereof.

Anti-obesity agents also include orexin antagonists, including, but not limited to, those described in PCT Patent Application Nos. WO 01/96302, WO 01/68609, WO 02/51232, and WO 02/51838. Specific orexin antagonists useful in compositions and methods of use provided include, but are not limited to, SB-334867-A.

Anti-obesity agents also include neuropeptide Y2 (NPY2) agonists, including, but not limited to, compounds such as PYY3-36 (e.g., Batterham et al. (2003) Nature 418:650-654), NPY3-36 and other Y2 agonists such as N acetyl [Leu (28,31)] NPY 24-36 (White-Smith et al. (1999) Neuropeptides 33:526-533, TASP-V (Malis et al. (1999) Br. J. Pharmacol. 126:989-996), cyclo-(28/32)-Ac-[Lys28-Glu32]-(25-36)-pNPY (Cabrele et al. (2000) J. Pept. Sci. 6:97-122), which can be either administered concurrently with a Peptide of the Invention or administered separately. Anti-obesity agents provided also include neuropeptide Y4 (NPY4) agonists including, but not limited to, compounds such as pancreatic peptide (PP) (e.g., Batterham et al. (2003) J. Clin. Endocrinol. Metab. 88:3989-3992) and other Y4 agonists such as 1229U91 (Raposinho et al. (2000) Neuroendocrinology 71:2-7). NPY2 agonists and NPY4 agonists, derivatives, preparations, formulations, pharmaceutical compositions, doses, and administration routes have previously been described, for example, in U.S. Pat. Publication No. 2002/0141985 and PCT Application Publication No. WO 2005/077094.

Anti-obesity agents also include histamine 3 (H3) antagonist/inverse agonists including but not limited to, those described in PCT Application No. WO 02/15905, O-[3-(1H-imidazol-4-yl) propanol] carbamates (Kiec-Kononowicz et al. (2000) Pharmazie 55:349-355), piperidine-containing histamine H3-receptor antagonists (Lazewska et al. (2001) Pharmazie 56:927-932), benzophenone derivatives and related compounds (Sasse et al. (2001) Arch. Pharm. (Weinheim) 334:45-52), substituted N-phenylcarbamates (Reidemeister et al. (2000) Pharmazie 55:83-86), and proxifan derivatives (Sasse et al. (2000) J. Med. Chem. 43:3335-3343). Specific H3 antagonists/inverse agonists useful in compositions and methods of use provided include, but are not limited to, thioperamide, 3-(1H-imidazol-4-yl) propyl N-(4-pentenyl) carbamate, clobenpropit, iodophenpropit, imoproxifan, and GT2394 (Gliatech).

Anti-obesity agents also include cholecystokinin (CCK) and CCK agonists. Cholecystokinin-A (CCK-A) agonists of use include, but are not limited to, those described in U.S. Pat. No. 5,739,106. Specific CCK-A agonists include, but are not limited to, AR-R 15849, GI 181771, JMV-180, A-71378, A-71623 and SR146131.

Anti-obesity agents also include ghrelin antagonists such as those described in PCT Application Publication Nos. WO 01/87335 and WO 02/08250. Ghrelin antagonists are also known as GHS (growth hormone secretagogue receptor) antagonists. The compositions and methods provided therefore contemplate the use GHS antagonists in place of ghrelin antagonists.

Anti-obesity agents include obestatin and obestatin analogs and agonists. Obestatin is a peptide derived from the same precursor from which ghrelin is derived, preproghrelin. See, for example, Zhang et al. (2005) Science 310:996-999; Nogueiras et al. (2005) Science 310:985-986; Pan et al. (2006) Peptides 27:911-916. In contrast to the activity of ghrelin, obestatin appears to act as an anorexic hormone by decreasing food intake, gastric emptying activities, jejunal motility, and body weight gain. Obestatin peptides of use include, but are not limited to those described in Zhang et al. (2005) Science 310:996-999.

And the amylinomimetics (e.g., a amylin-calcitonin receptor co-agonists such as davalintide), GLP-1-GIP receptor co-agonist such as incretins (e.g., exendin-4, leptin, and PYY analogs) are anti-obesity agents that also can be administered as an anti-obesity agents with a GIP comprising Peptide of the Invention.

Thus, in certain embodiments, the Peptide of the Invention are useful for treating or preventing conditions or disorders which can be alleviated by reducing nutrient availability comprising administering to said subject a therapeutically or prophylactically effective amount of a compound of the invention. Such conditions and disorders include, but are not limited to, control of food intake, weight loss, energy metabolism, plasma glucose levels, insulin levels, and/or insulin secretion, positive inotropic effects, reduction of catabolic effects, slowing of gastric emptying, obesity, diabetes and diabetes-related conditions, liver fat-associated inflammation and injury. Such conditions and disorders include, but are not limited to, hypertension, dyslipidemia, cardiovascular disease, eating disorders and rare genetic disorders of obesity such as Prader Willi Syndrome, critical care, insulin-resistance and disorders thereof such as polycystic ovary syndrome, obesity, diabetes mellitus of any kind, including type 1, type 2, and gestational diabetes, and CNS disorders such as preventing neurodegeneration, Alzheimer's disease and Parkinson's disease, and nonalcoholic steatohepatitis (NASH), as well as complications from diabetes (e.g. neuropathy (treating with a Peptide of the Invention including a GIP peptide containing an exendin family component for example), neuropathic pain (treating with a Peptide of the Invention including a GIP Peptide of the Invention comprising an amylin family hormone module for example), retinopathy, nephropathy, conditions of insufficient pancreatic beta cell mass (based on, e.g., islet neogenesis actions of exendin-4 and GLP-1), Metabolic Syndrome, Dumping Syndrome, polycystic ovary syndrome, hypertension, dyslipidemia, cardiovascular disease, hyperlipidemia, sleep apnea, cancer, pulmonary hypertension, cholecystitis, and osteoarthritis Non-limiting examples of a cardiovascular condition or disease are hypertension, myocardial ischemia, and myocardial reperfusion. Compounds of the invention may also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, Am. Fam. Phys. 63:2185, 2001). In other embodiments, Peptides of the Invention may be used to alter body composition for aesthetic reasons, to enhance one's physical capabilities, or to produce a leaner meat source. Peptides of the Invention are useful to change body composition by decreasing fat without significant decrease in muscle mass, thus producing a desirable loss of body fat while preserving lean body mass. In one embodiment such Peptides of the Invention contain an exendin, GLP1, amylin and/or sCT portion.

In another aspect of the invention, methods for treating or preventing obesity are provided, wherein the method comprises administering a therapeutically or prophylactically effective amount of a Peptide of the Invention to a subject in need thereof. In an exemplary embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from these Peptide of the Inventions. In one embodiment such Peptide of the Invention contains GIP, a amylin calcitonin receptor agonist such as davalintide, GLP-1-GIP receptor co-agonist such a an exendin, GLP1, amylin and/or sCT portion.

In other aspects of the invention, methods of reducing food intake, reducing nutrient availability, causing weight loss, affecting body composition, and altering body energy content or increasing energy expenditure, treating diabetes mellitus, and improving lipid profile (including reducing LDL cholesterol and triglyceride levels and/or changing HDL cholesterol levels) are provided, wherein the methods comprise administering to a subject an effective amount of a Peptide of the Invention. In an exemplary embodiment, the methods of the invention are used to treat or prevent conditions or disorders which can be alleviated by reducing nutrient availability in a subject in need thereof, comprising administering to said subject a therapeutically or prophylactically effective amount of a Peptide of the Invention. Such conditions and disorders include, but are not limited to, hypertension, dyslipidemia, cardiovascular disease, eating disorders, insulin-resistance, obesity, and diabetes mellitus of any kind. In one embodiment such Peptides of the Invention contain GIP, an exendin, GLP1, amylin and/or sCT portion.

Additional assays useful to the invention include those that can determine the effect of Peptides of the Invention, particularly those containing GIP, an exendin, GLP1, amylin and/or sCT portion, on body composition. An exemplary assay can be one that involves utilization of a diet-induced obese (DIO) mouse model for metabolic disease. Prior to the treatment period, male $C_{57}$BL/6J mice can be fed a high-fat diet (#D12331, 58% of calories from fat; Research Diets, Inc.,) for 6 weeks beginning at 4 weeks of age. During the study, the mice can continue to eat their high-fat diet. Water can be provided ad libitum throughout the study. One group of similarly-aged non-obese mice can be fed a low-fat diet (#D12329, 11% of calories from fat) for purposes of comparing metabolic parameters to DIO groups.

DIO mice can be implanted with subcutaneous (SC) intrascapular osmotic pumps to deliver either vehicle (50% dimethylsulfoxide (DMSO) in water) or a Peptide of the Invention. The pumps of the latter group can be set to deliver any amount, e.g., 1000 μg/kg/d of a Peptide of the Invention for 7-28 days. Body weights and food intake can be measured over regular intervals throughout the study periods. Respiratory quotient (RQ, defined as $CO_2$ production+O2 consumption) and metabolic rate can be determined using whole-animal indirect calorimetry (Oxymax, Columbus Instruments, Columbus, Ohio). The mice can be euthanized by isoflurane overdose, and an index of adiposity (bilateral epididymal fat pad weight) measured. Moreover, prior to determination of epididymal weight, body composition (lean mass, fat mass) for each mouse can be analyzed using a Dual Energy X-ray Absorptiometry (DEXA) instrument per manufacturer's instructions (Lunar Piximus, GE Imaging System). In the methods of the invention, Peptide of the Invention, particularly those comprising GIP, an exendin, PPF, PYY, GLP1, amylin and/or sCT portion having a potency in one of the assays described herein (preferably food intake, gastric emptying, pancreatic secretion, weight reduction or body composition assays) which is greater than the potency of a component peptide hormone in that same assay, can be identified.

In addition to the amelioration of hypertension in subjects in need thereof as a result of reduced food intake, weight loss, or treating obesity, Peptides of the Invention may be used to treat hypotension.

In another general aspect, Peptides of the Invention may be used to inhibit the secretion of ghrelin. Accordingly, Peptides of the Invention may utilize this mechanism to treat or prevent ghrelin related disorders such as Prader-Willi syndrome, diabetes of all types and its complications, obesity, hyperphagia, hyperlipidemia, or other disorders associated with hypernutrition.

Peptides of the Invention may also be useful for potentiating, inducing, enhancing or restoring glucose responsivity in pancreatic islets or cells. These actions may be useful for treating or preventing conditions associated with metabolic disorders such as those described above and in U.S. patent application no. US2004/0228846. Assays for determining such activity are known in the art. For example, in published U.S. patent application no. US2004/0228846 (incorporated by reference in its entirety), assays are described for islet isolation and culture as well as determining fetal islet maturation. In the examples of patent application US2004/0228846, intestine-derived hormone peptides including secretin, glucagon-like peptide-1 (GLP-1) and bombesin were purchased from Sigma. Collagenase type XI was obtained from Sigma. RPMI 1640 culture medium and fetal bovine serum were obtained from Gibco. A radioimmunoassay kit containing anti-insulin antibody ([125I]-RIA kit) was purchased from Linco, St Louis.

Peptides of the Invention are useful for prevention and treatment of nephropathy, including hypertensive and diabetic nephropathy, and nephropathy associated with insulin resistance and metabolic syndrome. Peptides of the Invention achieve these ends by, among other things, improving or preventing worsening of hypertension, endothelial function, renal function, and glomerulosclerosis. In one embodiment, the invention provides a method for preventing or treating nephropathy, including hypertensive and diabetic nephropathy, or that related to insulin resistance, comprising administering a compound of the invention. Peptides of the Invention find further use for improving endothelial function in a patient having reduced vasodilatory capacity, or having glomerulosclerosis or any other reduction in glomerular flow. Such improvement in endothelial function serves both to reduce hypertension and to improve the function of the capillaries of the glomeruli. In additional embodiments, the molecules of the invention are useful to prevent progression of nephropathy to ESRD, to prevent, slow the progression of, treat or ameliorate proteinuria and/or glomerulosclerosis.

Peptides of the Invention are useful for reducing the risk of suffering from, preventing, or treating cardiac arrhythmias. Peptides of the Invention can provide anti-arrhythmic effects in patients with cardiac ischemia, cardiac ischemia-reperfusion, and congestive heart failure. For example, incretin GLP-1 has been found to reduce cardiac injury and enhance recovery in patients with these disorders. Incretins, including GLP-1, are glucose-dependent insulinotropic hormones. GLP-1 and exendin effectively enhance peripheral glucose uptake without inducing dangerous hypoglycemia. They also strongly suppress glucagon secretion, independent of its insulinotropic action, and thereby powerfully reduce plasma free fatty acid (FFA) levels substantially more than can be accomplished with insulin. High FFA levels have been implicated as a major toxic mechanism during myocardial ischemia. In another embodiment Peptides of the Invention are useful for preventing and treating cardiac arrhythmias that reliably reduce injury associated with reperfusion and ischemia, and enhance patient recovery. In yet a further embodiment treatment after acute stroke or hemorrhage, preferably intravenous administration, provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects. In one embodiment such Peptides of the Invention contain GIP, a GLP1 or exendin portion.

In yet a further embodiment, Peptides of the Invention that are capable of lowering insulin resistance or increasing insulin sensitivity are useful to treat polycystic ovary syndrome (PCOS). Administering Peptides of the Invention can reduce or prevent insulin resistance in a subject suffering from PCOS. In yet another embodiment Peptides of the Invention prevent the onset of type-2 diabetes in a subject suffering from PCOS. Further Peptides of the Invention can restore regular menses, ovulation, or fertility in a subject suffering from PCOS. In one embodiment such GIP containing Peptides of the Invention also contain a GLP1 or an exendin portion for binding and activating a GLP1 receptor.

By selection of a Peptide of the Invention can exhibit a broad range of biological activities, some related to their antisecretory and antimotility properties. The Peptides of the Invention may suppress gastrointestinal secretions by direct interaction with epithelial cells or, perhaps, by inhibiting secretion of hormones or neurotransmitters which stimulate intestinal secretion. Anti-secretory properties include inhibition of gastric and/or pancreatic secretions and can be useful in the treatment or prevention of diseases and disorders including gastritis, pancreatitis, Barrett's esophagus, and Gastroesophageal Reflux Disease, as well as conditions associated therewith including heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), Barrett's esophageal adenocarcinoma, and pulmonary aspiration. In another embodiment GIP Peptide of the Invention containing amylin and/or sCT portions can be useful for treating or preventing these diseases and conditions, such as Barrett's esophagus, Gastroesophageal Reflux Disease (GERD) and conditions associated therewith as disclosed herein. Such Peptides of the Invention have particularly effective anti-secretory properties, such as inhibition of gastric acids, inhibition of bile acids, and inhibition of pancreatic enzymes. Moreover, such Peptides of the Invention can have a gastroprotective effect, which renders them particularly useful in the treatment or prevention of intestinal diseases and conditions and of Barrett's esophagus, and/or GERD and related or associated conditions as described herein.

In another general aspect, Peptides of the Invention are useful for decreasing bone resorption, decreasing plasma calcium, and/or inducing an analgesic effect, particularly to treat bone disorders such as osteopenia and osteoporosis. In yet other embodiments, Peptides of the Invention are useful to treat pain and painful neuropathy. In one embodiment such Peptides of the Invention contain an exendin, GLP1, amylin and/or sCT portion. For example, a GIP-sCT or GIP-amylin/sCT Peptides of the Invention can have a selectable property of a salmon calcitonin or amylin/sCT/Amylin chimera, such as decreasing bone loss and bone resorption or reducing cartilage turnover (chondroprotection), and a property of a GIP, such as plasma glucose lowering (concomitant with an anti-catabolic aspect as described herein) and/or inhibiting bone resorption and maintaining or increasing bone density. Peptides of the Invention with such selectable properties can enhance treatment of osteoporosis or conditions of high cartilage turnover, particularly in those who can also benefit from glycemic control, such as subjects with diabetes or undergoing critical care.

Pharmaceutical Compositions

In particular embodiments, the Peptides of the Invention, or the pharmaceutical composition comprising a Peptide of the Invention, is suspended in a sustained-release matrix. A sustained-release matrix, as used herein, is a matrix made of materials, usually polymers, which are degradable by enzymatic or acid-base hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. One embodiment of a biodegradable matrix is a matrix of one of either polylactide, polyglycolide, or polylactide co-glycolide (co-polymers of lactic acid and glycolic acid).

In certain embodiments, the present invention includes pharmaceutical compositions comprising one or more Peptides of the Invention and a pharmaceutically acceptable carrier, diluent or excipient. A pharmaceutically acceptable carrier, diluent or excipient refers to a non-toxic solid, semi-solid or liquid filler, diluent, encapsulating material or Formulation auxiliary of any type. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

In certain embodiments, the compositions are administered orally, parenterally, intracisternally, intravaginally, intraperitoneally, intrarectally, topically (as by powders, ointments, drops, suppository, or transdermal patch), by inhalation (such as intranasal spray), ocularly (such as intraocularly) or buccally. The term "parenteral" as used herein refers to modes of administration which include intravenous, intramuscular, intraperitoneal, intrasternal, subcutaneous, intradermal and intraarticular injection and infusion. Accordingly, in certain embodiments, the compositions are Formulated for delivery by any of these routes of administration.

In certain embodiments, pharmaceutical compositions for parenteral injection comprise pharmaceutically acceptable sterile aqueous or nonaqueous solutions, dispersions, suspensions or emulsions, or sterile powders, for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, β-cyclodextrin, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants. These compositions may also contain adjuvants such as preservative, wetting agents, emulsifying agents, and dispersing agents. Prolonged absorption of an injectable pharmaceutical form may be brought about by the inclusion of agents which delay absorption, such as aluminum monostearate and gelatin.

Injectable depot forms include those made by forming microencapsule matrices of the Peptides of the Invention in one or more biodegradable polymers such as polylactide-polyglycolide, poly(orthoesters), poly(anhydrides), and (poly)glycols, such as PEG. Depending upon the ratio of peptide to polymer and the nature of the particular polymer employed, the rate of release of the peptide can be controlled. Depot injectable Formulations are also prepared by entrapping the peptide in liposomes or microemulsions compatible with body tissues.

The injectable Formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Topical administration includes administration to the skin or mucosa, including surfaces of the lung and eye. Compositions for topical lung administration, including those for inhalation and intranasal, may involve solutions and suspensions in aqueous and non-aqueous Formulations and can be prepared as a dry powder which may be pressurized or non-pressurized. In non-pressurized powder compositions, the active ingredient may be finely divided form may be used in admixture with a larger-sized pharmaceutically acceptable inert carrier comprising particles having a size, for example, of up to 100 micrometers in diameter. Suitable inert carriers include sugars such as lactose.

Alternatively, the composition may be pressurized and contain a compressed gas, such as nitrogen or a liquefied gas propellant. The liquefied propellant medium and indeed the total composition may bey such that the active ingredient does not dissolve therein to any substantial extent. The pressurized composition may also contain a surface-active agent, such as a liquid or solid non-ionic surface-active agent or may be a solid anionic surface-active agent. It is preferred to use the solid anionic surface-active agent in the form of a sodium salt.

A further form of topical administration is to the eye. A Peptide of the Invention may be delivered in a pharmaceutically acceptable ophthalmic vehicle, such that the peptide is maintained in contact with the ocular surface for a sufficient time period to allow the peptide to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the Peptide of the Invention may be injected directly into the vitreous and aqueous humour.

Compositions for rectal or vaginal administration include suppositories which may be prepared by mixing the Peptides of the Invention with suitable non-irritating excipients or carriers such as cocoa butter, polyethylene glycol or a suppository wax, which are solid at room temperature but liquid at body temperature and, therefore, melt in the rectum or vaginal cavity and release the active compound.

Peptides of the Invention may also be administered in liposomes or other lipid-based carriers. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a Peptide of the Invention, stabilizers, preservatives, excipients, and the like. In certain embodiments, the lipids comprise phospholipids, including the phosphatidyl cholines (lecithins) and serines, both natural and synthetic. Methods to form liposomes are known in the art.

Peptides of the Invention may also be administered using FluidCrystal® technologies as described by Camurus. These formulations are based on special combinations of endogenous polar lipids that spontaneously form liquid crystal nanostructures in aqueous environments; at tissue surfaces or in the body. Such an FluidCrystal® injection depot is designed to provide treatment efficacy over extended periods (from days to months) with a single injection, and has the potential to reduce the burden of daily medication while increasing adherence to therapy.

The FluidCrystal® injection depot comprises a lipid-based liquid with a dissolved Peptide of the Invention that can easily be injected subcutaneously using a conventional syringe with a thin needle. Upon contact with fluids in the tissue, the lipid solution transforms into a liquid crystalline gel, which effectively encapsulates the peptide. The drug compound is slowly released as the liquid crystalline matrix gradually degrade in the tissue and the release can be controlled from several days to weeks or months depending on the composition.

Pharmaceutical compositions to be used in the invention suitable for parenteral administration may comprise sterile aqueous solutions and/or suspensions of the peptide inhibitors made isotonic with the blood of the recipient, generally using sodium chloride, glycerin, glucose, mannitol, sorbitol, and the like.

In some embodiments, the invention provides a pharmaceutical composition for oral delivery. Compositions and Peptides of the Invention may be prepared for oral administration according to any of the methods, techniques, and/or delivery vehicles described herein. Further, one having skill in the art will appreciate that the Peptides of the Invention may be modified or integrated into a system or delivery vehicle that is not disclosed herein, yet is well known in the art and compatible for use in oral delivery of peptides.

In certain embodiments, formulations for oral administration may comprise adjuvants (e.g. resorcinols and/or nonionic surfactants such as polyoxyethylene oleyl ether and n-hexadecylpolyethylene ether) to artificially increase the permeability of the intestinal walls, and/or enzymatic inhibitors (e.g. pancreatic trypsin inhibitors, diisopropylfluorophosphate (DFF) or trasylol) to inhibit enzymatic degradation. In certain embodiments, the Peptides of the Invention of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

In particular embodiments, oral dosage forms or unit doses compatible for use with the Peptides of the Invention may include a mixture of peptide and nondrug components or excipients, as well as other non-reusable materials that may be considered either as an ingredient or packaging. Oral compositions may include at least one of a liquid, a solid, and a semi-solid dosage forms. In some embodiments, an oral dosage form is provided comprising an effective amount of a Peptide of the Invention, wherein the dosage form comprises at least one of a pill, a tablet, a capsule, a gel, a paste, a drink, a syrup, ointment, and suppository. In some instances, an oral dosage form is provided that is designed and configured to achieve delayed release of the peptide in the subject's small intestine and/or colon.

In certain embodiments, an oral pharmaceutical composition comprising a Peptide of the Invention comprises an enteric coating that is designed to delay release of the Peptides of the Invention in the small intestine. In at least some embodiments, a pharmaceutical composition is provided which comprises a Peptide of the Invention and a protease inhibitor, such as aprotinin, in a delayed release pharmaceutical Formulation. In some instances, pharmaceutical compositions of the instant invention comprise an enteric coat that is soluble in gastric juice at a pH of about 5.0 or higher. In at least one embodiment, a pharmaceutical composition is provided comprising an enteric coating comprising a polymer having dissociable carboxylic groups, such as derivatives of cellulose, including hydroxypropylmethyl cellulose phthalate, cellulose acetate phthalate and cellulose acetate trimellitate and similar derivatives of cellulose and other carbohydrate polymers.

In certain embodiments, a pharmaceutical composition comprising a Peptide of the Invention is provided in an enteric coating, the enteric coating being designed to protect and release the pharmaceutical composition in a controlled manner within the subject's lower gastrointestinal system, and to avoid systemic side effects. In addition to enteric coatings, the Peptides of the Invention may be encapsulated, coated, engaged or otherwise associated within any compatible oral drug delivery system or component. For example, in some embodiments a Peptide of the Invention is provided in a lipid carrier system comprising at least one of polymeric hydrogels, nanoparticles, microspheres, micelles, and other lipid systems.

To overcome peptide degradation in the small intestine, some embodiments of the present invention comprise a hydrogel polymer carrier system in which a Peptide of the Invention is contained, whereby the hydrogel polymer protects the peptide from proteolysis in the small intestine and/or colon. The Peptides of the Invention may further be formulated for compatible use with a carrier system that is designed to increase the dissolution kinetics and enhance intestinal absorption of the peptide. These methods include the use of liposomes, micelles and nanoparticles to increase GI tract permeation of peptides.

Various bioresponsive systems may also be combined with one or more Peptides of the Invention to provide a pharmaceutical agent for oral delivery. In some embodiments, a Peptide of the Invention is used in combination with a bioresponsive system, such as hydrogels and mucoadhesive polymers with hydrogen bonding groups (e.g., PEG, poly(methacrylic) acid [PMAA], cellulose, Eudragit®, chitosan and alginate) to provide a therapeutic agent for oral administration. Other embodiments include a method for optimizing or prolonging drug residence time for a Peptide of the Invention disclosed herein, wherein the surface of the peptide surface is modified to comprise mucoadhesive properties through hydrogen bonds, polymers with linked mucins or/and hydrophobic interactions. These modified peptide molecules may demonstrate increase drug residence time within the subject, in accordance with a desired feature of the invention. Moreover, targeted mucoadhesive systems may specifically bind to receptors at the enterocytes and M-cell surfaces, thereby further increasing the uptake of particles containing the peptide.

Other embodiments comprise a method for oral delivery of a Peptide of the Invention, wherein the peptide is provided to a subject in combination with permeation enhancers that promote the transport of the peptides across the intestinal mucosa by increasing paracellular or transcellular permeation. Various permeation enhancers and methods for the oral delivery of therapeutic agents is described in Brayden, D.J., Mrsny, R. J., 2011. Oral peptide delivery: prioritizing the leading technologies. Ther. Delivery 2 (12), 1567-1573.

In certain embodiments, pharmaceutical compositions and formulations of the present invention comprises a Peptide of the Invention and one or more permeation enhancer. Examples of absorption enhancers may include Bile salts, fatty acids, surfactants (anionic, cationic, and nonanionic) chelators, Zonular OT, esters, cyclodextrin, dextran sulfate, azone, crown ethers, EDTA, sucrose esters, and phosphotidyl choline, for example. Although absorption enhancers are not typically carriers by themselves, they are also widely associated with other carriers to improve oral bioavailability by transporting of peptides and proteins across the intestinal mucosa. Such substances can be added to the Formulation as excipients or incorporated to form non-specific interactions with the intended Peptide of the Invention.

Dietary components and/or other naturally occurring substances affirmed as enhancing tight junction permeation and as Generally Recognized As Safe (GRAS) include, e.g., acylglycerides, acylcamitines, bile salts, and medium chain fatty acids. Sodium salts of medium chain fatty acids (MCFAS) were also suggested to be permeation enhancers. The most extensively studied MCFAS is sodium caprate, a salt of capric acid, which comprises 2-3% of the fatty acids in the milk fat fraction. To date, sodium caprate is mainly used as an excipient in a suppository Formulation (Doktacillin™) for improving rectal ampicillin absorption. The permeation properties of another dietary MCFAS, sodium caprylate (8-carbon), were shown in vitro to be lower when compared to sodium caprate. Sodium caprylate and a peptidic drug were Formulated in an admixture with other excipients in oil to generate an oily suspension (OS) that enhanced permeability (Tuvia, S. et al., Pharmaceutical Research, Vol. 31, No. 8, pp. 2010-2021 (2014).

For example, in certain embodiments, a permeation enhancer is combined with a Peptide of the Invention wherein the permeation enhancer comprises at least one of a medium-chain fatty acid, a long-chain fatty acid, a bile salt, an amphiphilic surfactant, and a chelating agent. In certain embodiments, medium-chain fatty acid salts promote absorption by increasing paracellular permeability of the intestinal epithelium. In certain embodiments, a permeation enhancer comprising sodium N-[hydroxybenzoyl)amino] caprylate is used to form a weak noncovalent association with the Peptides of the Invention, wherein the permeation enhancer favors membrane transport and further dissociation once reaching the blood circulation. In certain embodiments, a Peptide of the Invention is conjugated to oligoarginine, thereby increasing cellular penetration of the peptide into various cell types. Further, in at least one embodiment a noncovalent bond is provided between a Peptide of the Invention and a permeation enhancer selected from the group consisting of a cyclodextrin (CD) and a dendrimers, wherein the permeation enhancer reduces peptide aggregation and increasing stability and solubility for the Peptides of the Invention.

In certain embodiments, a pharmaceutical composition or formulation comprises a Peptide of the Invention and a transient permeability enhancers (TPEs). Permeation enhancers and TPEs may be used to increase orally bioavailability or the peptide. One example of a TPE that may be used is an oily suspension Formulation that disperses a powder containing sodium caprylate and a therapeutic agent (Tuvia, S. et al., Pharmaceutical Research, Vol. 31, No. 8, pp. 2010-2021 (2014).

In certain embodiments, pharmaceutical composition and formulations may include a Peptide of the Invention and one or more absorption enhancers, enzyme inhibitors, or mucosa adhesive polymers.

In particular embodiments, a Peptide of the Invention is formulated in a formulation vehicle, such as, e.g., emulsions, liposomes, microsphere or nanoparticles.

Other embodiments of the invention provide a method for treating a subject with a Peptide of the Invention having an increased half-life. In one aspect, the present invention provides a peptide having a half-life of at least several hours to one day in vitro or in vivo (e.g., when administered to a human subject) sufficient for daily (q.d.) or twice daily (b.i.d.) dosing of a therapeutically effective amount. In certain embodiments, the Peptides of the Invention has a half-life of three days or longer sufficient for weekly (q.w.) dosing of a therapeutically effective amount. In certain embodiments, the Peptide of the Invention has a half-life of eight days or longer sufficient for bi-weekly (b.i.w.) or monthly dosing of a therapeutically effective amount. In certain embodiments, the Peptide of the Invention is derivatized or modified such that is has a longer half-life as compared to the underivatized or unmodified peptide. In certain embodiments, the peptide contains one or more chemical modifications to increase serum half-life.

When used in at least one of the treatments or delivery systems described herein, a Peptide of the Invention may be employed in pure form or, where such forms exist, in pharmaceutically acceptable salt form.

The total daily usage of the Peptides of the Invention and compositions of the present invention can be decided by the attending physician within the scope of sound medical judgment. The specific therapeutically effective dose level for any particular subject will depend upon a variety of factors including: a) the disorder being treated and the severity of the disorder; b) activity of the specific compound employed; c) the specific composition employed, the age, body weight, general health, sex and diet of the patient; d) the time of administration, route of administration, and rate of excretion of the specific Peptide of the Invention employed; e) the duration of the treatment; f) drugs used in combination or coincidental with the specific Peptide of the Invention employed, and like factors well known in the medical arts.

In particular embodiments, the total daily dose of the Peptides of the Invention to be administered to a human or other mammal host in single or divided doses may be in amounts, for example, from 0.0001 to 300 mg/kg body weight daily or 1 to 300 mg/kg body weight daily.

EXAMPLES OF THE INVENTION

Example 1: Peptide Synthesis

Peptides were synthesized on Gyros Protein Technologies Symphony X synthesizers via solid phase peptide chemistry (SPPS)/Fmoc chemistry using polystyrene or PEG based resins. Fmoc chemistry employs Fmoc (fluorenylmethyloxycarbonyl) protecting group at the N-terminus of each amino acids, which is removed by a base (usually 20% piperidine in DMF) before the next coupling cycle. As an example, (Peptide No. 12) was made using TentaGel RAM resin (with a loading of 0.18 mmol/g) and sequential coupling and deprotection of Fmoc-protected amino acid derivatives. A lipidated extended Lysine residue was introduced as a single, preformed Fmoc derivative at position 20 of the sequence.

Upon completion of SPPS, TFA mediated cleavage from the resin along with concomitant protecting group removal was performed, followed by isolation via precipitation and filtration with diethyl ether to yield 285 mg of crude material. Disulphide bond formation was effected using hydrogen peroxide in a aqueous solution at pH 8.6.

Preparative reverse-phase HPLC was performed on a Teledyne Isco ACCQ Prep HP150 System with a variable wavelength UV absorbance detector, and the material was lyophilized to provide 91 mg of purified peptide. Purity of 80.2% was determined by analytical reverse-phase HPLC performed on an Dionex UltiMate 3000system and mass identity was confirmed on a Kratos Axima CFR Plus MALDI-MS. The measured mass of 7537.39 agreed with the calculated mass of 7537.46, and the product was further characterized by its amino acid content of 93.1%. Table 9 illustrates analytical characteristics of exemplary peptides of the invention.

TABLE 9

| Peptide Name | Theoretical MW | Experimental MW | Purity | Peptide Content |
|---|---|---|---|---|
| SEQ ID NO: 10 acetate salt | 7862.82 | 7862.42 | 98.7% | 86.0% |
| SEQ ID NO: 12 acetate salt | 7537.46 | 7537.39 | 80.2% | 93.1% |
| SEQ ID NO: 14 acetate salt | 7509.40 | 7509.67 | 90.0% | 97.7% |
| SEQ ID NO: 15 acetate salt | 7550.46 | 7550.15 | 83.6% | 97.0% |
| SEQ ID NO: 16 acetate salt | 6926.63 | 6926.94 | 92.7% | 89.0% |
| SEQ ID NO: 17 acetate salt | 7550.46 | 7550.83 | 88.5% | 86.9% |
| SEQ ID NO: 18 acetate salt | 7509.40 | 7509.41 | 95.0% | 87.5% |
| SEQ ID NO: 19 acetate salt | 7607.51 | 7607.82 | 89.9% | 78.0% |
| SEQ ID NO: 20 acetate salt | 7597.47 | 7597.93 | 88.1% | 92.4% |
| SEQ ID NO: 21 acetate salt | 7510.39 | 7509.99 | 82.8% | 80.8% |
| SEQ ID NO: 22 acetate salt | 7835.75 | 7835.48 | 91.7% | 86.8% |

Example 2: Biological activity of peptides in cell-based Cyclic AMP activity Assay Peptides were tested in cAMP cell-based assays to determine their potency against calcitonin, AMY3, GLP-1 and GIP human receptors. Peptide activation of these various receptors results in downstream production of cAMP second messenger which can be measured in a functional activity assay.

The potency ($EC_{50}$) of peptides for the different human receptors were evaluated using stably transfected CHO-K1 cells overexpressing non-tagged human calcitonin, AMY3, GLP-1 and GIP receptors was determined in GPCR cell-based CAMP assays, including CT Human Calcitonin GPCR Cell Based Agonist CAMP Assay (catalog 86-0007P-2245AG), AMY3 (CT/RAMP3) Human Calcitonin GPCR Cell Based Agonist cAMP Assay (catalog 86-0007P-2276AG), GIP Human Glucagon GPCR Cell Based Agonist cAMP Assay, (catalog 86-0007P-2308AG), GLP-1 Human Glucagon GPCR Cell Based Agonist cAMP Assay, (catalog 86-0007P-2309AG), all from Eurofins (Fremont, CA).

Experimental protocol: Cells were seeded in a total volume of 20 μL into white walled, 384-well microplates and incubated at 37° C. overnight prior to testing. Prior to testing, cell plating media was exchanged with 10 μL of Assay buffer (HBSS+10 mM HEPES). All compounds were run in assay buffer containing 0.1% casein. Briefly, intermediate dilution of sample stocks was performed to generate 4× sample in assay buffer. 5 μL of 4× sample was added to cells and incubated at 37° C. for 30 minutes. Final assay vehicle concentration was 1%. After appropriate compound incubation, assay signal was generated through incubation with 5 μl of Antibody and 20 μl cAMP XS+ED/CL lysis cocktail for one hour followed by incubation with 20 μl cAMP XS+EA reagent for 2 hours at room temperature.

Microplates were read following signal generation with PerkinElmer Envision instrument for chemiluminescent signal detection. Data was normalized to the maximal and minimal response observed in the presence of control ligand and vehicle.

The results are expressed as a percent efficacy relative to the maximum response of the control ligand.

Compounds exhibited activity against the different human receptors tested as demonstrated in the cyclic AMP assay. Summary of the in vitro results, $EC_{50}$ for control peptides and exemplary peptides of the invention are illustrated in Table 10.

TABLE 10

Potency Of Peptides For Different Human Receptors

| Peptide | Human Calci-toninR $EC_{50}$ (nM) | Human Calc/RAMP3R $EC_{50}$ (nM) | Human GIPR $EC_{50}$ (nM) | Human GLP-1R $EC_{50}$ (nM) |
|---|---|---|---|---|
| Calcitonin | 0.098 | | | |
| Adrenomodulin | | 37 | | |
| GIP | | | 0.017 | |
| Exendin-4 | | | | 0.007 |
| SEQ ID NO: 10 | 12.4 | 7 | 0.05 | 3.87 |
| SEQ ID NO: 12 | 0.046 | 0.444 | 0.072 | 8.22 |
| SEQ ID NO: 14 | 0.031 | 0.39 | 0.67 | 23 |
| SEQ ID NO: 15 | 0.071 | 1.1 | 0.13 | 5.2 |
| SEQ ID NO: 16 | 0.005 | 0.069 | 0.14 | 0.24 |
| SEQ ID NO: 17 | 0.1 | 1.3 | 0.81 | 5.7 |
| SEQ ID NO: 18 | 0.034 | 0.44 | 1.8 | 31.7 |
| SEQ ID NO: 19 | 0.1 | 1.03 | 4.6 | 8.23 |
| SEQ ID NO: 20 | 0.036 | 0.39 | 2 | 10 |
| SEQ ID NO: 21 | 0.11 | 1.6 | 20 | 43 |
| SEQ ID NO: 22 | 5.78 | 15 | 16 | 42 |

Example 3: Acute Food Intake Studies in Lean Mice

Lean C57BL/6j male mice were used to assess the acute food intake effects of the peptides. C57BL/6j male mice at 6 weeks of age were purchased from Charles River (Spain) and housed individually. Mice were kept in 12 h light/dark cycles (lights on at 8 am) in temperature-(22° C.) and humidity (45-55%)-controlled rooms. Mice were fed ad libitum a standard rodent chow diet (CHD) (A04, U8220G1OR, SAFE). At eight weeks of age, the mice were acclimatized to reverse light/dark cycles for at least 7 days prior to peptide administration.

Peptides Peptide No. 12, Peptide No. 14, Peptide No. 15, and Peptide No. 17 were reconstituted in vehicle 20 mM Tris-HCl, 7.5 mg/mL mannitol, pH 7.0 and Peptide No. 16 was reconstituted in vehicle 5 mM NaAc, 2.5 mg/mL mannitol, pH 5.0 at 1 mg/ml. All peptide solutions were aliquoted and stored at −20° C. until use. Dilutions for injection were done in saline buffer.

Mice were randomized in the experimental groups according to body weight. For Peptide No. 12, Peptide No. 14, Peptide No. 15 and Peptide No. 17, 12-h fasted mice received a single subcutaneous (s.c.) injection 2 h before turning lights off at the doses indicated in each experiment (n=6 per group). As control, mice received a single injection of equivalent volume of the corresponding vehicle. For Peptide No. 16, 12-h fasted mice received a single s.c. injection 10 min before lights were turned off. As control, mice received a single injection of equivalent volume of its corresponding vehicle (n=5 per group). Food was replaced immediately after lights were turned off. Food intake was measured at different time-intervals post-injection up to 72 h using a precision balance. Cumulative food intake was calculated for the indicated time-periods.

All data shown are the mean±standard error (SEM). Statistical evaluation of the data was carried out using one-way ANOVA, followed by Bonferroni post-hoc test to determine any statistically significant differences between vehicle and peptide-treated groups. Differences were considered statistically significant at $p<0.05$. Data analysis was carried out with GraphPad software (GraphPad Prism).

Results are shown in Table 11. Exemplary peptides induced food intake reduction in lean mice after single administration.

TABLE 11

Acute Food Intake In Lean Mice After A Single Administration of Peptides

| Peptide (dose) | Cumulative Food Intake Reduction Relative to Vehicle (%) | | | |
|---|---|---|---|---|
| SEQ ID NO: 12 (50 nmoles/kg) | 48.5 ± 2.45 | 12.4 ± 2.93 | 3.5 ± 2.10 | 3.1 ± 1.93 |
| SEQ ID NO: 14 (50 nmoles/kg) | 31.5 ± 4.2 | 4.1 ± 4.59 | 2.4 ± 3.81 | 3.3 ± 4.05 |
| SEQ ID NO: 15 (50 nmoles/kg) | 10.6 ± 3.34 | 8.8 ± 3.52 | 9.9 ± 3.69 | 8.7 ± 3.97 |
| SEQ ID NO: 16 (50 nmoles/kg) | 62.5 ± 2.06 | 58.3 ± 1.15 | 39.8 ± 2.03 | 23.6 ± 2.03 |
| SEQ ID NO: 17 (50 nmoles/kg) | 20.5 ± 0.86 | 25.3 ± 1.93 | 12.2 ± 4.03 | 2.6 ± 5.68 |

Example 4: Effect on Blood Glucose after single administration of peptides

Glucose-lowering action of the peptides was used to demonstrate that the incretin portion of the molecule has an effect in vivo. Non-fasted mice (n=5 per group) received a single s.c. injection of peptides, all at 50 nmol/kg or the equivalent volume of the respective vehicle. Blood samples were collected from tail clips at 0, 30 and 120 minutes after injection for glucose measurements. Glucose using a glucometer (Accu-chek Aviva, Roche Diagnostics). Calculations of glucose lowering at 30 and 120 min was done vs Time 0.

All data shown are the mean±standard error (SEM). Statistical evaluation of the data was carried out using one-way ANOVA, followed by Bonferroni post-hoc test to determine any statistically significant differences between vehicle and peptide-treated groups. Differences were considered statistically significant at $p<0.05$. Data analysis was carried out with GraphPad software (GraphPad Prism).

Figure 1B:
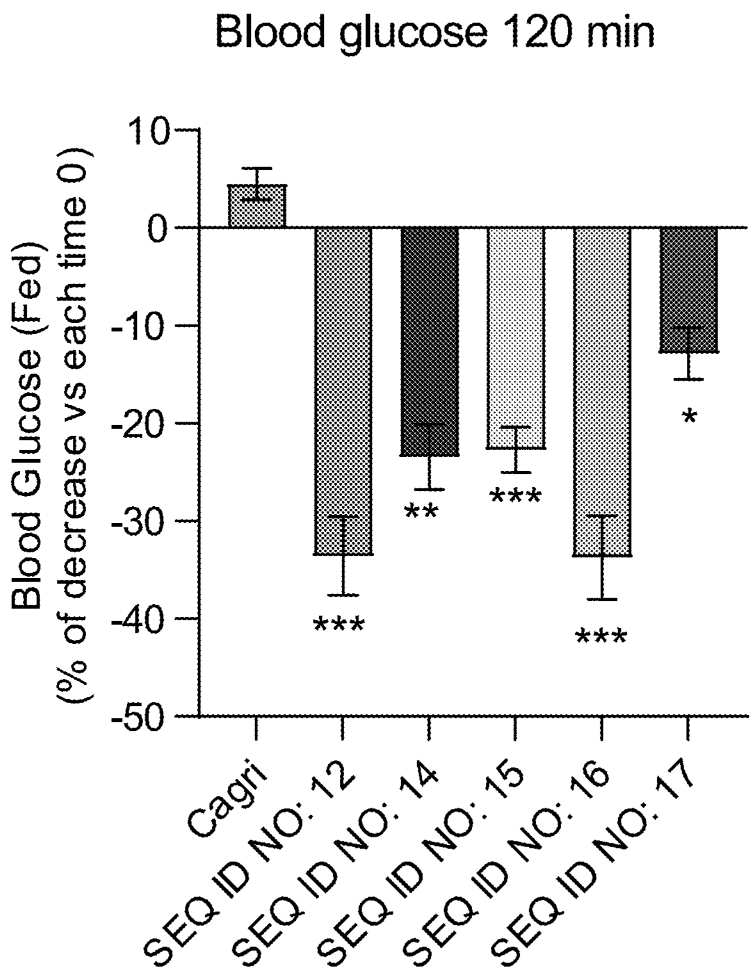

Peptides of the Invention but not Cagrilitide (a dual calcitonin/amylin agonist) significantly reduced blood glucose at 30 and 120 min compared to time 0 as shown in Table 12 and FIGS. 1A and 1B.

TABLE 12

Effect of peptides on blood glucose after single administration. Blood glucose (mg/dL)

| Peptide | Time 0 (mg/dL) | 30 min (mg/dL) | 120 min (mg/dL) |
|---|---|---|---|
| SEQ ID NO: 12 (50 nmoles/Kg) | 166.2 ± 8.08 | 134.6 ± 5.66 | 109.0 ± 5.22 |
| SEQ ID NO: 14 (50 nmoles/Kg) | 166.0 ± 5.24 | 148.8 ± 4.21 | 126.4 ± 3.96 |
| SEQ ID NO: 15 (50 nmoles/Kg) | 170.8 ± 3.53 | 142.0 ± 8.15 | 132.0 ± 5.28 |
| SEQ ID NO: 16 (50 nmoles/Kg) | 155.6 ± 2.38 | 111.6 ± 3.28 | 102.8 ± 7.30 |
| SEQ ID NO: 17 (50 nmoles/Kg) | 159.6 ± 5.78 | 140.4 ± 8.41 | 138.4 ± 1.63 |
| Cagrilintide (50 nmoles/Kg) | 150.2 ± 1.36 | 163.2 ± 3.62 | 157.0 ± 3.85 |

Example 5: Acute Food Intake And Body Weight Reduction In Lean Rats

Sprague Dawley male rats (5 weeks of age) were purchased from Charles River (Spain) and single housed for individual registration of food consumption. The rats were acclimatized to reverse light cycle (12 h light and 12 h dark) and single housing at least 5 days prior to testing at controlled temperature conditions (22° C.) and humidity (45-55%)-controlled rooms. Rats were fed ad libitum a standard rodent chow diet (CHD) (A04, U8220G1OR, SAFE).

Sprague Dawley rats (200-250 g), randomized in the different experimental groups by body weight, were fasted 8 h prior to lights off (at 8 µm). Two hours prior the onset of the dark cycle, the rats were injected (s.c.) with peptides (Peptide No. 12, Peptide No. 14, and Peptide No. 17) or the corresponding vehicle at the indicated doses for each experiment (n=5 per group). For Peptide No. 16 and its corresponding vehicle control (n=5 per group), 8-h fasted rats received a single s.c. injection 10 min prior the onset of the dark cycle. For all experimental groups, food was replaced immediately after lights were turned off.

Food intake was measured at different time-intervals post-injection up to 72 h using a precision balance. Cumulative food intake was calculated for the indicated time-periods. Body weight was measured at the indicated time-periods. Mean accumulated food intake in each dose group was compared to vehicle and reported as a percentage of mean food intake in the vehicle group, which was defined as 100%.

All data shown are the mean±standard error (SEM). Results are shown in tables 13, 14, and 15. Peptides induce a reduction in food intake and body weight in lean rats after single administration.

TABLE 13

| Food Intake Reduction by Intervals vs. Vehicle (%) | | | | |
|---|---|---|---|---|
| Peptide | 0-12 hr. | 12-24 hr. | 24-48 hr. | 48-72 hr. |
| SEQ ID NO: 12 (50 nmoles/kg) | 62.3 +/- 3.18 | 50.7 +/- 3.32 | 12.5 +/- 3.32 | 6.3 +/- 3.54 |
| SEQ ID NO: 14 (50 nmoles/kg) | 56.7 +/- 3.47 | 59.7 +/- 5.02 | 7.9 +/- 5.02 | -0.2 +/- 2.25 |
| SEQ ID NO: 17 (50 nmoles/kg) | 21.8 +/- 2.62 | 89.1 +/- 3.69 | 32.8 +/- 3.69 | 19.4 +/- 2.31 |
| SEQ ID NO: 16 (50 nmoles/kg) | 57.0 +/- 5.92 | 14.3 +/- 4.22 | 4.3 +/- 4.22 | -6.4 +/- 10.96 |

TABLE 14

| Cumulative Food Intake Reduction vs. Vehicle (%) | | | | |
|---|---|---|---|---|
| Peptide | 12 hr. | 24 hr. | 48 hr. | 72 hr. |
| SEQ ID NO: 12 (50 nmoles/kg) | 62.3 +/- 3.18 | 59.9 +/- 3.19 | 38.4 +/- 1.89 | 23.3 +/- 1.62 |
| SEQ ID NO: 14 (50 nmoles/kg) | 56.7 +/- 3.47 | 57.4 +/- 3.69 | 34.9 +/- 2.82 | 18.4 +/- 0.67 |
| SEQ ID NO: 17 (50 nmoles/kg) | 21.8 +/- 2.62 | 31.8 +/- 2.10 | 32.3 +/- 1.66 | 28.7 +/- 1.69 |
| SEQ ID NO: 16 (50 nmoles/kg) | 57.0 +/- 5.92 | 47.5 +/- 4.73 | 26.0 +/- 2.91 | 16.2 +/- 4.61 |

TABLE 15

| Body Weight Reduction (G) In Lean Rats After Single Administration of Peptides | | | |
|---|---|---|---|
| Peptide | 24 h (g) | 48 h (g) | 72 h (g) |
| SEQ ID NO: 12 | −11.8 ± 1.07 | −11.7 ± 1.07 | −7.2 ± 1.17 |
| SEQ ID NO: 14 | −8.8 ± 1.83 | −7.2 ± 1.34 | −4.2 ± 1.11 |
| SEQ ID NO: 16 | −12.0 ± 1.54 | −14.4 ± 1.43 | −14.2 ± 2.46 |
| SEQ ID NO: 17 | −9.0 ± 1.01 | −13.0 ± 0.84 | −14.8 ± 1.30 |

All of the above U.S. patents, U.S. patent application publications, U.S. patent applications, foreign patents, foreign patent applications and non-patent publications referred to in this specification are incorporated herein by reference in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

```
Sequence total quantity: 29
SEQ ID NO: 1             moltype = AA  length = 69
FEATURE                  Location/Qualifiers
source                   1..69
                         mol_type = protein
                         organism = synthetic construct
SITE                     2
                         note = D-Alanine
SEQUENCE: 1
YAEGTFISDY SIALDKIHQQ DFVNWLLAQK GSGCNTATCA TQRLANFLVH SSNNFGPILP  60
PTNVGSNTY                                                          69

SEQ ID NO: 2             moltype = AA  length = 69
FEATURE                  Location/Qualifiers
source                   1..69
                         mol_type = protein
                         organism = synthetic construct
SITE                     2
                         note = D-Alanine
SITE                     32
                         note = Lysine-gamma-glutamyl-gamma-glutamyl-C=O(CH2)n-R;
                          where R is -CO2H, -CO2CH3, -CO2NH2, -CO2NHCH3,
                          -CO2N(CH3)2, -CH3, or -NH2, and n is an integer from 12-20
SEQUENCE: 2
YAEGTFISDY SIALDKIHQQ DFVNWLLAQK GXGCNTATCA TQRLANFLVH SSNNFGPILP  60
PTNVGSNTY                                                          69

SEQ ID NO: 3             moltype = AA  length = 69
FEATURE                  Location/Qualifiers
source                   1..69
                         mol_type = protein
                         organism = synthetic construct
SITE                     2
                         note = D-Alanine
SITE                     58
                         note = Lysine-gamma-glutamyl-gamma-glutamyl-C=O(CH2)n-R;
                          where R is -CO2H, -CO2CH3, -CO2NH2, -CO2NHCH3,
                          -CO2N(CH3)2, -CH3, or -NH2, and n is an integer from 12-20
SEQUENCE: 3
YAEGTFISDY SIALDKIHQQ DFVNWLLAQK GSGCNTATCA TQRLANFLVH SSNNFGPXLP  60
PTNVGSNTY                                                          69

SEQ ID NO: 4             moltype = AA  length = 69
FEATURE                  Location/Qualifiers
```

-continued

```
source                  1..69
                        mol_type = protein
                        organism = synthetic construct
SITE                    2
                        note = D-Alanine
SITE                    66
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 4
YAEGTFISDY SIALDKIHQQ DFVNWLLAQK GSGCNTATCA TQRLANFLVH SSNNFGPILP  60
PTNVGXNTY                                                          69

SEQ ID NO: 5            moltype = AA  length = 69
FEATURE                 Location/Qualifiers
source                  1..69
                        mol_type = protein
                        organism = synthetic construct
SITE                    2
                        note = D-Alanine
SEQUENCE: 5
YAEGTFISDY SIALDKIHQQ DFVNWLLAGG PSSCNTATCA TQRLANFLVH SSNNFGPILP  60
PTNVGSNTY                                                          69

SEQ ID NO: 6            moltype = AA  length = 64
FEATURE                 Location/Qualifiers
source                  1..64
                        mol_type = protein
                        organism = synthetic construct
SITE                    2
                        note = D-Alanine
SEQUENCE: 6
YAEGTFISDY SIALDKIHQQ DFVNWLLAQK GSGCNTATCV LGRLSQELHR LQTYPRTNTG  60
SNTY                                                               64

SEQ ID NO: 7            moltype = AA  length = 64
FEATURE                 Location/Qualifiers
source                  1..64
                        mol_type = protein
                        organism = synthetic construct
SITE                    2
                        note = D-Alanine
SITE                    32
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 7
YAEGTFISDY SIALDKIHQQ DFVNWLLAQK GXGCNTATCV LGRLSQELHR LQTYPRTNTG  60
SNTY                                                               64

SEQ ID NO: 8            moltype = AA  length = 64
FEATURE                 Location/Qualifiers
source                  1..64
                        mol_type = protein
                        organism = synthetic construct
SITE                    2
                        note = D-Alanine
SITE                    61
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 8
YAEGTFISDY SIALDKIHQQ DFVNWLLAQK GSGCNTATCV LGRLSQELHR LQTYPRTNTG  60
XNTY                                                               64

SEQ ID NO: 9            moltype = AA  length = 68
FEATURE                 Location/Qualifiers
source                  1..68
                        mol_type = protein
                        organism = synthetic construct
SITE                    2
                        note = 2-aminoisobutyric acid
SITE                    13
                        note = 2-aminoisobutyric acid
SEQUENCE: 9
YXEGTFTSDY SIXLDKIAQQ AFVQWLLAGG PSCNTATCAT QRLANFLVHS SNNFGPILPP  60
TNVGSNTY                                                           68

SEQ ID NO: 10           moltype = AA  length = 68
```

-continued

```
FEATURE               Location/Qualifiers
source                1..68
                      mol_type = protein
                      organism = synthetic construct
SITE                  2
                      note = 2-aminoisobutyric acid
SITE                  13
                      note = 2-aminoisobutyric acid
SITE                  20
                      note = Lysine-gamma-glutamyl-gamma-glutamyl-C=O(CH2)n-R;
                       where R is -CO2H, -CO2CH3, -CO2NH2, -CO2NHCH3,
                       -CO2N(CH3)2, -CH3, or -NH2, and n is an integer from 12-20
SEQUENCE: 10
YXEGTFTSDY SIXLDKIAQX AFVQWLLAGG PSCNTATCAT QRLANFLVHS SNNFGPILPP  60
TNVGSNTY                                                           68

SEQ ID NO: 11         moltype = AA  length = 63
FEATURE               Location/Qualifiers
source                1..63
                      mol_type = protein
                      organism = synthetic construct
SITE                  2
                      note = 2-aminoisobutyric acid
SITE                  13
                      note = 2-aminoisobutyric acid
SEQUENCE: 11
YXEGTFTSDY SIXLDKIAQQ AFVQWLLAGG PSCNTATCVL GRLSQELHRL QTYPRTNTGS  60
NTY                                                                63

SEQ ID NO: 12         moltype = AA  length = 63
FEATURE               Location/Qualifiers
source                1..63
                      mol_type = protein
                      organism = synthetic construct
SITE                  2
                      note = 2-aminoisobutyric acid
SITE                  13
                      note = 2-aminoisobutyric acid
SITE                  20
                      note = Lysine-gamma-glutamyl-gamma-glutamyl-C=O(CH2)n-R;
                       where R is -CO2H, -CO2CH3, -CO2NH2, -CO2NHCH3,
                       -CO2N(CH3)2, -CH3, or -NH2, and n is an integer from 12-20
SEQUENCE: 12
YXEGTFTSDY SIXLDKIAQX AFVQWLLAGG PSCNTATCVL GRLSQELHRL QTYPRTNTGS  60
NTY                                                                63

SEQ ID NO: 13         moltype = AA  length = 63
FEATURE               Location/Qualifiers
source                1..63
                      mol_type = protein
                      organism = synthetic construct
SITE                  2
                      note = D-Alanine
SEQUENCE: 13
YAEGTFTSDY SIALDKIAQQ AFVQWLLAGG PSCNTATCVL GRLSQELHRL QTYPRTNTGS  60
NTY                                                                63

SEQ ID NO: 14         moltype = AA  length = 63
FEATURE               Location/Qualifiers
source                1..63
                      mol_type = protein
                      organism = synthetic construct
SITE                  2
                      note = D-Alanine
SITE                  20
                      note = Lysine-gamma-glutamyl-gamma-glutamyl-C=O(CH2)n-R;
                       where R is -CO2H, -CO2CH3, -CO2NH2, -CO2NHCH3,
                       -CO2N(CH3)2, -CH3, or -NH2, and n is an integer from 12-20
SEQUENCE: 14
YAEGTFTSDY SIALDKIAQX AFVQWLLAGG PSCNTATCVL GRLSQELHRL QTYPRTNTGS  60
NTY                                                                63

SEQ ID NO: 15         moltype = AA  length = 63
FEATURE               Location/Qualifiers
source                1..63
                      mol_type = protein
                      organism = synthetic construct
SITE                  2
                      note = D-Alanine
```

-continued

```
SITE                    60
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 15
YAEGTFTSDY SIALDKIAQQ AFVQWLLAGG PSCNTATCVL GRLSQELHRL QTYPRTNTGX  60
NTY                                                                63

SEQ ID NO: 16           moltype = AA  length = 63
FEATURE                 Location/Qualifiers
source                  1..63
                        mol_type = protein
                        organism = synthetic construct
SITE                    1
                        note = D-Tyrosine
SEQUENCE: 16
YAEGTFTSDY SIALDKIAQQ AFVQWLLAGG PSCNTATCVL GRLSQELHRL QTYPRTNTGS  60
NTY                                                                63

SEQ ID NO: 17           moltype = AA  length = 63
FEATURE                 Location/Qualifiers
source                  1..63
                        mol_type = protein
                        organism = synthetic construct
SITE                    1
                        note = D-Tyrosine
SITE                    60
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 17
YAEGTFTSDY SIALDKIAQQ AFVQWLLAGG PSCNTATCVL GRLSQELHRL QTYPRTNTGX  60
NTY                                                                63

SEQ ID NO: 18           moltype = AA  length = 63
FEATURE                 Location/Qualifiers
source                  1..63
                        mol_type = protein
                        organism = synthetic construct
SITE                    1
                        note = D-Tyrosine
SITE                    20
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 18
YAEGTFTSDY SIALDKIAQX AFVQWLLAGG PSCNTATCVL GRLSQELHRL QTYPRTNTGS  60
NTY                                                                63

SEQ ID NO: 19           moltype = AA  length = 63
FEATURE                 Location/Qualifiers
source                  1..63
                        mol_type = protein
                        organism = synthetic construct
SITE                    1
                        note = D-Tyrosine
SITE                    60
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 19
YAEGTFTSDY SIQLDKIAQQ AFVQWLLAGG PSCNTATCVL GRLSQELHRL QTYPRTNTGX  60
NTY                                                                63

SEQ ID NO: 20           moltype = AA  length = 63
FEATURE                 Location/Qualifiers
source                  1..63
                        mol_type = protein
                        organism = synthetic construct
SITE                    1
                        note = D-Tyrosine
SITE                    30
                        note = Lysine-gamma-glutamyl-gamma-glutamyl-C=O(CH2)n-R;
                         where R is -CO2H, -CO2CH3, -CO2NH2, -CO2NHCH3,
                         -CO2N(CH3)2, -CH3, or -NH2, and n is an integer from 12-20
SEQUENCE: 20
YAEGTFTSDY SIQLDKIAQQ AFVQWLLAGX GSCNTATCVL GRLSQELHRL QTYPRTNTGS  60
NTY                                                                63
```

-continued

```
SEQ ID NO: 21          moltype = AA  length = 62
FEATURE                Location/Qualifiers
source                 1..62
                       mol_type = protein
                       organism = synthetic construct
SITE                   1
                       note = D-Tyrosine
SITE                   59
                       note = Lysine-gamma-glutamyl-gamma-glutamyl-C=O(CH2)n-R;
                        where R is -CO2H, -CO2CH3, -CO2NH2, -CO2NHCH3,
                        -CO2N(CH3)2, -CH3, or -NH2, and n is an integer from 12-20
SEQUENCE: 21
YAEGTFTSDY SIQLDKIAQQ AFVQWLLAGS GCNTATCVLG RLSQELHRLQ TYPRTNTGXN  60
TY                                                                 62

SEQ ID NO: 22          moltype = AA  length = 67
FEATURE                Location/Qualifiers
source                 1..67
                       mol_type = protein
                       organism = synthetic construct
SITE                   1
                       note = D-Tyrosine
SITE                   64
                       note = Lysine-gamma-glutamyl-gamma-glutamyl-C=O(CH2)n-R;
                        where R is -CO2H, -CO2CH3, -CO2NH2, -CO2NHCH3,
                        -CO2N(CH3)2, -CH3, or -NH2, and n is an integer from 12-20
SEQUENCE: 22
YAEGTFTSDY SIQLDKIAQQ AFVQWLLAGS GCNTATCATQ RLANFLVHSS NNFGPILPPT  60
NVGXNTY                                                            67

SEQ ID NO: 23          moltype = AA  length = 69
FEATURE                Location/Qualifiers
VARIANT                1
                       note = X is Y or D-Tyrosine
VARIANT                2
                       note = X is A, D-Alanine or Aib
VARIANT                7
                       note = X is I or T
VARIANT                13
                       note = X is A, Aib or Q
VARIANT                14
                       note = X is M, L or V
VARIANT                18
                       note = X is A or H
VARIANT                20
                       note = X is Q, K or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                21
                       note = X is A or D
VARIANT                24
                       note = X is N or Q
VARIANT                27
                       note = X is L, V or I
VARIANT                28
                       note = X is A or V
VARIANT                29
                       note = X is G or Q
VARIANT                30
                       note = X is G, K, R, S, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                31
                       note = X is is P, G, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                32
                       note = X is S, G, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                33
                       note = X is absent or is G or S
VARIANT                40
                       note = X is A, M or V
VARIANT                41
```

-continued

```
                          note = X is T or L
VARIANT                   42
                          note = X is Q or G
VARIANT                   43
                          note = X is R, K, Q, or
                           Lys-gamma-glutamyl-gamma-glutamyl-C=O(CH2)nR3, wherein R3
                           is -CO2H, -CO2CH3, -CO2NH2, -CO2NHCH3, -CO2N(CH3)2, -CH3,
                           or -NH2, and n is an integer from 12-20
VARIANT                   45
                          note = X is A or S
VARIANT                   46
                          note = X is N or Q
VARIANT                   47
                          note = X is F or E
VARIANT                   49
                          note = X is H or V
VARIANT                   50
                          note = X is H or R
VARIANT                   51
                          note = X is S or L
VARIANT                   52
                          note = X is S or Q
VARIANT                   53
                          note = X is N or T
VARIANT                   54
                          note = X is absent or is N or Q
VARIANT                   55
                          note = X is absent or is F
VARIANT                   56
                          note = X is absent or is G
VARIANT                   57
                          note = X is absent or is P
VARIANT                   58
                          note = X is absent or is I, K, or
                           Lys-gamma-glutamyl-gamma-glutamyl-C=O(CH2)nR3, wherein R3
                           is -CO2H, -CO2CH3, -CO2NH2, -CO2NHCH3, -CO2N(CH3)2, -CH3,
                           or -NH2, and n is an integer from 12-20
VARIANT                   59
                          note = X is L or Y
VARIANT                   61
                          note = X is P, K, R, or
                           Lys-gamma-glutamyl-gamma-glutamyl-C=O(CH2)nR3, wherein R3
                           is -CO2H, -CO2CH3, -CO2NH2, -CO2NHCH3, -CO2N(CH3)2, -CH3,
                           or -NH2, and n is an integer from 12-20
VARIANT                   64
                          note = X is V or T
VARIANT                   66
                          note = X is S, K, or
                           Lys-gamma-glutamyl-gamma-glutamyl-C=O(CH2)nR3, wherein R3
                           is -CO2H, -CO2CH3, -CO2NH2, -CO2NHCH3, -CO2N(CH3)2, -CH3,
                           or -NH2, and n is an integer from 12-20
SITE                      69
                          note = C-terminus is modified with -NH or -NC1-5 alkyl
source                    1..69
                          mol_type = protein
                          organism = synthetic construct
SEQUENCE: 23
XXEGTFXSDY SIXXDKIXQX XFVXWLXXXX XXXCNTATCX XXXLXXXLXX XXXXXXXXXP  60
XTNXGXNTY                                                          69

SEQ ID NO: 24             moltype = AA  length = 69
FEATURE                   Location/Qualifiers
VARIANT                   1
                          note = X is Y or D-Tyrosine
VARIANT                   2
                          note = X is A, D-Alanine or Aib
VARIANT                   7
                          note = X is T or I
VARIANT                   14
                          note = X is M, L or V
VARIANT                   18
                          note = X is H or A
VARIANT                   20
                          note = X is Q, K, or
                           Lys-gamma-glutamyl-gamma-glutamyl-C=O(CH2)nR3, wherein R3
                           is -CO2H, -CO2CH3, -CO2NH2, -CO2NHCH3, -CO2N(CH3)2, -CH3,
                           or -NH2, and n is an integer from 12-20
VARIANT                   21
                          note = X is D or A
```

-continued

```
VARIANT                24
                       note = X is N or Q
VARIANT                30
                       note = X is Q, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                31..33
                       note = X is any naturally occurring amino acid
VARIANT                58
                       note = X is I, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                66
                       note = X is S, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
SITE                   69
                       note = C-terminus is modified with -NH or -NC1-5 alkyl
source                 1..69
                       mol_type = protein
                       organism = synthetic construct
SEQUENCE: 24
XXEGTFXSDY SIAXDKIXQX XFVXWLLAQX XXXCNTATCA TQRLANFLVH SSNNFGPXLP  60
PTNVGXNTY                                                          69

SEQ ID NO: 25          moltype = AA  length = 63
FEATURE                Location/Qualifiers
VARIANT                1
                       note = X is Y or D-Tyrosine
VARIANT                2
                       note = X is A, D-Alanine or Aib
VARIANT                7
                       note = X is I or T
VARIANT                13
                       note = X is A or Aib
VARIANT                20
                       note = X is Q, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
VARIANT                27
                       note = X is L or I
VARIANT                60
                       note = X is S, K, or
                        Lys-gamma-glutamyl-gamma-glutamyl-C=O(CH2)nR3, wherein R3
                        is -CO2H, -CO2CH3, -CO2NH2, -CO2NHCH3, -CO2N(CH3)2, -CH3,
                        or -NH2, and n is an integer from 12-20
SITE                   63
                       note = C-terminus is modified with -NH or -NC1-5 alkyl
source                 1..63
                       mol_type = protein
                       organism = synthetic construct
SEQUENCE: 25
XXEGTFXSDY SIXLDKIAQX AFVQWLXAGG PSCNTATCVL GRLSQELHRL QTYPRTNTGX  60
NTY                                                                63

SEQ ID NO: 26          moltype = AA  length = 4
FEATURE                Location/Qualifiers
source                 1..4
                       mol_type = protein
                       organism = synthetic construct
SEQUENCE: 26
GGPS                                                               4

SEQ ID NO: 27          moltype = AA  length = 15
FEATURE                Location/Qualifiers
source                 1..15
                       mol_type = protein
                       organism = Homo sapiens
SEQUENCE: 27
YAEGTFISDY SIAMD                                                   15

SEQ ID NO: 28          moltype = AA  length = 12
FEATURE                Location/Qualifiers
source                 1..12
                       mol_type = protein
```

-continued

```
                          organism = Homo sapiens
SEQUENCE: 28
GTFISDYSIA MD                                                         12

SEQ ID NO: 29             moltype = AA  length = 69
FEATURE                   Location/Qualifiers
SITE                      14
                          note = Lys-gamma-glutamyl-gamma-glutamyl-C=O(CH2)nR3,
                           wherein R3 is -CO2H, -CO2CH3, -CO2NH2, -CO2NHCH3,
                           -CO2N(CH3)2, -CH3, or -NH2, and n is an integer from 12-20
VARIANT                   21
                          note = X is any naturally occurring amino acid
SITE                      69
                          note = C-terminus is modified with -NH or -NC1-5 alkyl
source                    1..69
                          mol_type = protein
                          organism = synthetic construct
VARIANT                   24
                          note = X is any naturally occurring amino acid
VARIANT                   30
                          note = X is any naturally occurring amino acid
VARIANT                   33
                          note = X is any naturally occurring amino acid
VARIANT                   58
                          note = X is any naturally occurring amino acid
VARIANT                   66
                          note = X is any naturally occurring amino acid
SEQUENCE: 29
YAEGTFLSDY SIAXDKINQQ XFVXWLLAQX ISXCNTATCA TQRLANFLVH SSNNFGPXLP  60
PTNVGXNTY                                                          69
```

What is claimed is:

1. A peptide or pharmaceutically acceptable salt thereof having any one of the following sequences:

| | |
|---|---|
| (SEQ ID NO: 1) | Y-(d)A-E-G-T-F-I-S-D-Y-S-I-A-L-D-K-I-H-Q-Q-D-F-V-N-W-L-L-A-Q-K-G-S-G-C-N-T-A-T-C-A-T-Q-R-L-A-N-F-L-V-H-S-S-N-N-F-G-P-I-L-P-P-T-N-V-G-S-N-T-Y-$NH_2$ |
| (SEQ ID NO: 2) | Y-(d)A-E-G-T-F-J-S-D-Y-S-I-A-L-D-K-I-H-Q-Q-D-F-V-N-W-L-L-A-Q-K-G-K*-G-C-N-T-A-T-C-A-T-Q-R-L-A-N-F-L-V-H-S-S-N-N-F-G-P-I-L-P-P-T-N-V-G-S-N-T-Y-$NH_2$ |
| (SEQ ID) NO: 3) | Y-(d)A-E-G-T-F-I-S-D-Y-S-I-A-L-D-K-I-H-Q-Q-D-F-V-N-W-L-L-A-Q-K-G-S-G-C-N-T-A-T-C-A-T-Q-R-L-A-N-F-L-V-H-S-S-N-N-F-G-P-K*-L-P-P-T-N-V-G-S-N-T-Y-$NH_2$ |
| (SEQ ID NO: 4) | Y-(d)A-E-G-T-F-I-S-D-Y-S-I-A-L-D-K-I-H-Q-Q-D-F-V-N-W-L-L-A-Q-K-G-S-G-C-N-T-A-T-C-A-T-Q-R-L-A-N-F-L-V-H-S-S-N-N-F-G-P-I-L-P-P-T-N-V-G-K*-N-T-Y-$NH_2$ |
| (SEQ ID NO: 5) | Y-(d)A-E-G-T-F-I-S-D-Y-S-I-A-L-D-K-I-H-Q-Q-D-F-V-N-W-L-L-A-G-G-P-S-S-C-N-T-A-T-C-A-T-Q-R-L-A-N-F-L-V-H-S-S-N-N-F-G-P-I-L-P-P-T-N-V-G-S-N-T-Y-$NH_2$ |
| (SEQ ID NO: 6) | Y-(d)A-E-G-T-F-I-S-D-Y-S-I-A-L-D-K-I-H-Q-Q-D-F-V-N-W-L-L-A-Q-K-G-S-G-C-N-T-A-T-C-V-L-G-R-L-S-Q-E-L-H-R-L-Q-T-Y-P-R-T-N-T-G-S-N-T-Y-$NH_2$ |
| (SEQ ID NO: 7) | Y-(d)A-E-G-T-F-I-S-D-Y-S-I-A-L-D-K-I-H-Q-Q-D-F-V-N-W-L-L-A-Q-K-G-K*-G-C-N-T-A-T-C-V-L-G-R-L-S-Q-E-L-H-R-L-Q-T-Y-P-R-T-N-T-G-S-N-T-Y-$NH_2$ |
| (SEQ ID NO: 8) | Y-(d)A-E-G-T-P-I-S-D-Y-S-I-A-L-D-K-I-H-Q-Q-D-F-V-N-W-L-L-A-Q-K-G-S-G-C-N-T-A-T-C-V-L-G-R-L-S-Q-E-L-H-R-L-Q-T-Y-P-R-T-N-T-G-K*-N-T-Y-$NH_2$ |

-continued

| | |
|---|---|
| (SEQ ID NO: 9) | Y-Aib-E-G-T-F-T-S-D-Y-S-I-Aib-L-D-K-I-A-Q-Q-A-P-V-Q-W-L-L-A-G-G-P-S-C-N-T-A-T-C-A-T-Q-R-L-A-N-F-L-V-H-S-S-N-N-F-G-P-I-L-P-P-T-N-V-G-S-N-T-Y-$NH_2$ |
| (SEQ ID NO: 10) | Y-Aib-E-G-T-F-T-S-D-Y-S-I-Aib-L-D-K-I-A-Q-K*-A-F-V-Q-W-L-L-A-G-G-P-S-C-N-T-A-T-C-A-T-Q-R-L-A-N-F-L-V-H-S-S-N-N-F-G-P-I-L-P-P-T-N-V-G-S-N-T-Y-$NH_2$ |
| (SEQ ID NO: 11) | Y-Aib-E-G-T-F-T-S-D-Y-S-I-Aib-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-Q-S-N-T-Y-$NH_2$ |
| (SEQ ID NO: 12) | Y-Aib-E-G-T-F-T-S-D-Y-S-I-Aib-L-D-K-I-A-Q-K*-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| (SEQ ID NO: 13) | Y-(d)A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| (SEQ ID NO: 14) | Y-(d)A-E-G-T-F-T-S-D-Y-S-I-A-L-D-K*-I-A-Q-K-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| (SEQ ID NO: 15) | Y-(d)A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-K*-N-T-Y-$NH_2$ |
| (SEQ ID NO: 16) | (d)Y-A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-S-N-T-Y-$NH_2$ |
| (SEQ ID NO: 17) | (d)Y-A-E-G-T-F-T-S-D-Y-S-I-A-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-K*-N-T-Y-$NH_2$ |

-continued

| | |
|---|---|
| (SEQ 10 NO: 18) | (d)Y-A-E-G-T-F-T-S-D-Y-S-I-A-L-D-K-I-A-Q-K*-A-F-V-Q-W-L-L-A-G-G-P-S-C-N-T-A-T-C-V-I-G-R-L-S-Q-E-L-H-R-L-Q-T-Y-P-R-T-N-T-G-S-N-T-Y-$NH_2$ |
| (SEQ ID NO: 19) | (d)Y-A-E-G-T-F-T-S-D-Y-S-I-Q-L-D-K-I-A-Q-Q-A-F-V-Q-W-L-L-A-G-G-P-S-C-N-T-A-T-C-V-L-G-R-L-S-Q-E-L-H-R-L-Q-T-Y-P-R-T-N-T-G-K*-N-T-Y-$NH_2$ |
| (SEQ ID NO: 20) | (d)Y-A-E-G-T-F-T-S-D-Y-S-I-Q-L-D-K-I-A-Q-Q-A-F-V-Q-W-L-L-A-G-K*-G-S-C-N-T-A-T-C-V-L-G-R-L-S-Q-E-L-H-R-L-Q-T-Y-P-R-T-N-T-G-S-N-T-Y-$NH_2$ |
| (SEQ ID NO: 21) | (d)Y-A-E-G-T-F-T-S-D-Y-S-I-Q-L-D-K-I-A-Q-Q-A-F-V-Q-W-L-L-A-G-S-G-C-N-T-A-T-C-V-L-G-R-L-S-Q-E-L-H-R-L-Q-T-Y-P-R-T-N-T-G-K*-N-T-Y-$NH_2$ |
| (SEQ ID NO: 22) | (d)Y-A-E-G-T-F-T-S-D-Y-S-I-Q-L-D-K-I-A-Q-Q-A-F-V-Q-W-L-L-A-G-S-G-C-N-T-A-T-C-A-T-Q-R-L-A-N-F-L-V-H-S-S-N-N-F-G-P-I-L-P-P-T-N-V-G-K*-N-T-Y-$NH_2$ |

wherein K* in the above-identified sequences is Lys-γ-Glu-γ-Glu-C═O$(CH_2)_nR^3$, wherein n is an integer from 12-20, and $R^3$ is $CO_2H$, —$CO_2CH_3$, —$CO_2NH_2$, —$CO_2NHCH_3$, —$CO_2N(CH_3)_2$, —$CH_3$, or —$NH_2$.

2. The peptide or pharmaceutically acceptable salt thereof of claim 1, wherein K* is Lys-γ-Glu-γ-Glu-C═O$(CH_2)_{18}CO_2H$ or Lys-γ-Glu-γ-Glu-C═O$(CH_2)_{18}CH_3$.

3. A pharmaceutical composition comprising the peptide or pharmaceutically acceptable salt thereof of claim 1, and a pharmaceutically acceptable carrier, excipient, or diluent.

4. A method for treating obesity, a metabolic disorder, or a liver disorder in a subject in need thereof comprising administering to the subject an effective amount of the pharmaceutical composition of claim 3.

5. The method of claim 4, wherein the peptide or pharmaceutically acceptable salt thereof is provided to the subject by an oral, parenteral, intravenous, peritoneal, intradermal, subcutaneous, intramuscular, intrathecal, inhalation, vaporization, nebulization, sublingual, buccal, parenteral, rectal, intraocular, inhalation, topically, vaginal, or topical route of administration.

6. The method of claim 4 for treating obesity.

7. A method for treating diabetes in a subject in need thereof comprising administering to the subject an effective amount of the pharmaceutical composition of claim 3.

8. The method of claim 4, wherein the effective amount of the peptide or pharmaceutically acceptable salt thereof or the pharmaceutical composition is from about 0.0001 to about 300 mg/kg body weight daily.

* * * * *